(12) United States Patent
Vitalis et al.

(10) Patent No.: US 11,124,781 B2
(45) Date of Patent: *Sep. 21, 2021

(54) P97-IDS FUSION PROTEINS

(71) Applicant: Bioasis Technologies Inc., Guilford, CT (US)

(72) Inventors: Timothy Z. Vitalis, Vancouver (CA); Reinhard Gabathuler, Montreal (CA)

(73) Assignee: Bioasis Technologies, Inc., BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/449,359

(22) Filed: Jun. 22, 2019

(65) Prior Publication Data

US 2020/0270590 A1 Aug. 27, 2020

Related U.S. Application Data

(63) Continuation of application No. 15/119,293, filed as application No. PCT/US2015/015662 on Feb. 12, 2015, now Pat. No. 10,392,605.

(60) Provisional application No. 61/941,896, filed on Feb. 19, 2014.

(51) Int. Cl.
| | |
|---|---|
| A61K 38/00 | (2006.01) |
| C12N 9/14 | (2006.01) |
| C12N 9/16 | (2006.01) |
| A61K 38/40 | (2006.01) |
| A61K 38/46 | (2006.01) |
| C07K 14/705 | (2006.01) |
| A61K 9/00 | (2006.01) |

(52) U.S. Cl.
CPC ............... *C12N 9/14* (2013.01); *A61K 38/40* (2013.01); *A61K 38/465* (2013.01); *C07K 14/70596* (2013.01); *C12N 9/16* (2013.01); *C12Y 301/06013* (2013.01); *C12Y 306/04006* (2013.01); *A61K 9/0019* (2013.01); *A61K 38/00* (2013.01); *C07K 2319/00* (2013.01); *C07K 2319/21* (2013.01); *C07K 2319/43* (2013.01); *C07K 2319/50* (2013.01)

(58) Field of Classification Search
CPC .. C12Y 301/06013; A61K 38/00; C12N 9/16; C12N 9/14; C12N 11/00; C07K 2517/00; C07K 14/79; C07K 2319/00
See application file for complete search history.

(56) References Cited

U.S. PATENT DOCUMENTS

| | | | |
|---|---|---|---|
| 4,391,904 A | 7/1983 | Litman et al. | |
| 4,394,448 A | 7/1983 | Szoka, Jr. et al. | |
| 4,399,216 A | 8/1983 | Axel et al. | |
| 4,683,195 A | 7/1987 | Mullis et al. | |
| 4,683,202 A | 7/1987 | Mullis | |
| 4,704,362 A | 11/1987 | Itakura et al. | |
| 4,766,075 A | 8/1988 | Goeddel et al. | |
| 4,784,950 A | 11/1988 | Hagen et al. | |
| 4,800,159 A | 1/1989 | Mullis et al. | |
| 4,801,542 A | 1/1989 | Murray et al. | |
| 4,866,042 A | 9/1989 | Neuwelt | |
| 4,935,349 A | 6/1990 | McKnight et al. | |
| 4,946,778 A | 8/1990 | Ladner et al. | |
| 5,091,513 A | 2/1992 | Huston et al. | |
| 5,132,405 A | 7/1992 | Huston et al. | |
| 5,186,941 A | 2/1993 | Callahan et al. | |
| 5,672,683 A | 9/1997 | Friden et al. | |
| 5,677,171 A | 10/1997 | Hudziak et al. | |
| 5,720,937 A | 2/1998 | Hudziak et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,798,239 A | 8/1998 | Wilson et al. | |
| 5,844,093 A | 12/1998 | Kettleborough et al. | |
| 5,932,211 A | 8/1999 | Wilson et al. | |
| 5,962,012 A | 10/1999 | Lin et al. | |
| 5,981,194 A | 11/1999 | Jefferies et al. | |
| 6,015,557 A | 1/2000 | Tobinick et al. | |
| 6,165,464 A | 12/2000 | Hudziak et al. | |
| 6,177,077 B1 | 1/2001 | Tobinick | |
| 6,261,595 B1 | 7/2001 | Stanley et al. | |
| 6,387,371 B1 | 5/2002 | Hudziak et al. | |
| 6,399,063 B1 | 6/2002 | Hudziak et al. | |

(Continued)

FOREIGN PATENT DOCUMENTS

| | | |
|---|---|---|
| GB | 2188637 A | 10/1987 |
| WO | 89/04663 A1 | 6/1989 |

(Continued)

OTHER PUBLICATIONS

Jolly, R. D. et al., "Lysosomal storage diseases of animals: an essay in comparative pathology," Veterinary Pathology Online, 34:527-548 (1997).

Kakkis, E. et al., "Successful induction of immune tolerance to enzyme replacement therapy in canine mucopolysaccharidosis I," Proceedings of the National Academy of Sciences, 101(3):829-834 (20041).

Kakkis, P. E. P., "Overexpression of the human lysosomal enzyme alpha-L-iduronidase in CHO cells," Protein Expression and Purification, 5(3):225-232 (1994).

(Continued)

*Primary Examiner* — Karen Cochrane Carlson
(74) *Attorney, Agent, or Firm* — Locke Lord LLP; Nicholas J. DiCeglie, Jr.; Scott D. Wofsy

(57) ABSTRACT

Provided are fusion proteins between p97 (melanotransferrin) and iduronate-2-sulfatase (IDS), and related compositions and methods of use thereof, for instance, to facilitate delivery of IDS across the blood-brain barrier (BBB) and/or improve its tissue penetration in CNS and/or peripheral tissues, and thereby treat and/or diagnose Hunter Syndrome (Mucopolysaccharidosis type II; MPS II) and related lysosomal storage disorders, including those having a central nervous system (CNS) component.

12 Claims, 5 Drawing Sheets

Specification includes a Sequence Listing.

(56) References Cited

U.S. PATENT DOCUMENTS

| | | |
|---|---|---|
| 6,419,934 B1 | 7/2002 | Tobinick |
| 6,419,944 B2 | 7/2002 | Tobinick |
| 6,455,494 B1 | 9/2002 | Jefferies et al. |
| 6,537,549 B2 | 3/2003 | Tobinick |
| 6,537,785 B1 | 3/2003 | Canfield |
| 6,596,541 B2 | 7/2003 | Murphy et al. |
| 6,765,087 B1 | 7/2004 | Casterman et al. |
| 6,838,254 B1 | 1/2005 | Hamers et al. |
| 6,982,089 B2 | 1/2006 | Tobinick |
| 7,132,511 B2 | 11/2006 | Carr et al. |
| 7,138,371 B2 | 11/2006 | DeFrees et al. |
| 7,179,617 B2 | 2/2007 | DeFrees et al. |
| 7,214,658 B2 | 5/2007 | Tobinick |
| 7,244,592 B2 | 7/2007 | Hoogenboom et al. |
| 7,247,301 B2 | 7/2007 | van de Winkel et al. |
| 7,462,697 B2 | 12/2008 | Couto et al. |
| 7,595,378 B2 | 9/2009 | van de Winkel et al. |
| 7,700,554 B2 | 4/2010 | Beliveau et al. |
| 7,723,484 B2 | 5/2010 | Beidler et al. |
| 7,939,072 B2 | 5/2011 | Yarden et al. |
| 7,960,516 B2 | 6/2011 | Matheus et al. |
| 8,546,319 B2 * | 10/2013 | Starr ............... A61K 47/64 514/1 |
| 8,722,019 B2 * | 5/2014 | Jefferies ............ C07K 16/18 424/9.34 |
| 9,150,846 B2 | 10/2015 | Jefferies et al. |
| 9,161,992 B2 | 10/2015 | Jefferies et al. |
| 9,364,567 B2 * | 6/2016 | Vitalis ............ C12Y 306/04006 |
| 9,850,472 B2 | 12/2017 | Vitalis et al. |
| 9,932,565 B2 | 4/2018 | Vitalis et al. |
| 9,993,530 B2 | 6/2018 | Vitalis et al. |
| 10,058,610 B2 | 8/2018 | Lantto et al. |
| 10,392,605 B2 * | 8/2019 | Vitalis ..................... C12N 9/14 |
| 10,772,939 B2 * | 9/2020 | Vitalis ..................... A61P 31/12 |
| 2002/0059032 A1 | 5/2002 | Ferrer et al. |
| 2002/0119095 A1 | 8/2002 | Gabathuler et al. |
| 2003/0072761 A1 | 4/2003 | LeBowitz |
| 2003/0129186 A1 | 7/2003 | Beliveau et al. |
| 2004/0055022 A1 | 3/2004 | Cheng |
| 2004/0137557 A1 | 7/2004 | DeFrees et al. |
| 2005/0026823 A1 | 2/2005 | Zankel et al. |
| 2005/0158296 A1 | 7/2005 | Starr et al. |
| 2007/0167365 A1 | 7/2007 | Beliveau et al. |
| 2008/0014188 A1 | 1/2008 | Zankel et al. |
| 2008/0152645 A1 | 6/2008 | Pardridge et al. |
| 2009/0226421 A1 | 9/2009 | Parren et al. |
| 2010/0129359 A1 | 5/2010 | Tobinick |
| 2010/0183581 A1 | 7/2010 | Beliveau et al. |
| 2010/0297120 A1 | 11/2010 | Beliveau et al. |
| 2010/0303797 A1 | 12/2010 | Starr |
| 2011/0093962 A1 | 4/2011 | Heidbrink et al. |
| 2011/0142763 A1 | 6/2011 | Zankel et al. |
| 2011/0318323 A1 | 12/2011 | Zhu et al. |
| 2012/0003202 A1 | 1/2012 | Calias et al. |
| 2012/0107302 A1 | 5/2012 | Berry et al. |
| 2013/0108548 A1 | 5/2013 | Vlieghe et al. |
| 2013/0183368 A1 | 7/2013 | Hutchison et al. |
| 2013/0236442 A1 | 9/2013 | Lee et al. |
| 2014/0004097 A1 * | 1/2014 | Zhang ...................... A61P 3/00 424/94.6 |
| 2014/0105880 A1 | 4/2014 | Starr et al. |
| 2014/0178350 A1 | 6/2014 | Vitalis et al. |
| 2014/0322132 A1 | 10/2014 | Vitalis et al. |
| 2015/0056218 A1 | 2/2015 | Jeffries et al. |
| 2015/0093399 A1 | 4/2015 | Jefferies |
| 2016/0053237 A1 | 2/2016 | Jefferies et al. |
| 2016/0324937 A1 | 11/2016 | Vitalis et al. |
| 2016/0347821 A1 | 12/2016 | Vitalis et al. |
| 2017/0204386 A1 | 7/2017 | Vitalis et al. |
| 2018/0021445 A1 | 1/2018 | Starr et al. |
| 2019/0002852 A1 | 1/2019 | Vitalis et al. |
| 2019/0008929 A1 | 1/2019 | Vitalis et al. |
| 2019/0022244 A1 | 1/2019 | Jefferies et al. |

FOREIGN PATENT DOCUMENTS

| | | |
|---|---|---|
| WO | 93/11161 A1 | 6/1993 |
| WO | 94/01463 A1 | 1/1994 |
| WO | 94/13804 | 6/1994 |
| WO | 98/23646 A2 | 6/1998 |
| WO | 2000/050636 A1 | 8/2000 |
| WO | 2001/059459 A2 | 8/2001 |
| WO | 2001/083722 A2 | 11/2001 |
| WO | 2002/013843 A2 | 2/2002 |
| WO | 2002/013873 A2 | 2/2002 |
| WO | 2003/009815 A2 | 2/2003 |
| WO | 2003/057179 A2 | 7/2003 |
| WO | 03057179 * | 7/2003 |
| WO | 2004/078215 A2 | 9/2004 |
| WO | 2005/034979 A2 | 4/2005 |
| WO | 2006/079372 A1 | 8/2006 |
| WO | 2008/022349 A2 | 2/2008 |
| WO | 2008/118013 A2 | 10/2008 |
| WO | 2009/019314 A1 | 2/2009 |
| WO | 2011/044542 A1 | 4/2011 |
| WO | 2011/131693 A2 | 10/2011 |
| WO | 2011/163649 A2 | 12/2011 |
| WO | 2013/006706 A1 | 1/2013 |
| WO | 2013022738 * | 2/2013 |
| WO | 2014/022515 A1 | 2/2014 |
| WO | 2014/022738 A1 | 2/2014 |
| WO | 2014/064258 A1 | 5/2014 |
| WO | 2015/031673 A2 | 3/2015 |
| WO | 2015/117121 A1 | 8/2015 |
| WO | 2015/126729 A1 | 8/2015 |
| WO | 2015/168521 A2 | 11/2015 |
| WO | 2017/123928 A1 | 7/2017 |

OTHER PUBLICATIONS

Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition 23 (11.55-59 (19951).

Kang, Y. S. et al., "Stability of the disulfide bond in an avidin-biotin linked chimeric peptide during in vivo transcytosis through brain endothelial cells," Journal of Drug Targeting, 8(6):425-434 (2000).

Kang, Y. S. et al., "Use of neutral avidin improves pharmacokinetics and brain delivery of biotin bound to an avidin-monoclonal antibody conjugate," Journal of Pharmacology & Experimental Therapeutics. 269(11:344-350 (19941).

Karkan, D. et al., "A unique carrier for delivery of therapeutic compounds beyond the blood-brain barrier," PLOS One, 3(6):E2469. 1-E2469.14 (2008).

King, T. P. et al., "Preparation of protein conjugates via intermolecular hydrazone linkage," Biochem, 25 (19):5774-5779 (1986).

Kurihara, A. et al., "A111-40 Peptide radiopharmaceuticals for brain amyloid imaing: III-Inchelation, conjugation to poly(ethylene glycol)-biotin linkers, and autoradiography with Alzheimer's disease brain sections " Rioconiunate Chem 11.380-386 (20001).

Mahapatro, A. et al., "Biodegradable nanoparticles are excellent vehicle for site directed in-vivo delivery of drugs and vaccines," Journal of Nanobiotechnology, 9(1):55 (2011).

Maccallum et al. (J. Mol. Biol. Oct. 11, 1996; 262 (5): 732-745).

Millat, G. et al., "IDS transfer from overexpressing cells to IDS-deficient cells," Experimental Cell Research, 230 (2):362-367 (Feb. 1997).

Moos, T. et al., "Restricted transport of anti-transferrin receptor antibody (0X26) through the blood-brain barrier in the rat," Journal of Neurochemistry, 79(1):119-129 (2001).

Muraszoko, K. et al., "Pharmacokinetics and toxicology of immunotoxins administered into the subarachnoid space in nonhuman primates and rodents," Cancer Research, 53(16):3752-3757 (1993).

Muruganandam, A. et al., "Selection of phage-displayed llama single-domain antibodies that transmigrate across human blood-brain barrier endothelium," FASEB Journal, 16(2):240-242 (2001).

(56) References Cited

OTHER PUBLICATIONS

Pardridge, W. M., "Drug transport across the blood-brain barrier," Journal of Cerebral Blood Flow & Metabolism, 32 (11):1959-1972 (2012).
Pardridge, W. M. et al., "Transport of human recombinant brain-derived neurotrophic factor (BDNF) through the rat blood-brain barrier in vivo using vector-mediated peptide drug delivery," Pharmaceutical Research. 11(50:738-746 (19941).
Parenti, G., "Treating lysosomal storage diseases with pharmacological chaperones: from concept to clinics," EMBO Ml. Med., 1:268-279 (2009).
Qian, Z. M. et al., "Targeted drug delivery via the transferrin receptor-mediated endocytosis pathway," Pharmacol. Rev., 54(4):561-587 (2002).
Queen, C. et al., "A humanized antibody that binds to the interleukin 2 receptor," Proc. Natl. Acad. Sci. USA, 86:10029-10033 (1988).
Richardson, D. R. et al., "The uptake of iron and transferrin by the human malignant melanoma cell," Biochimica et Biophysica Acta, 1053:1-12 (1990).
Rudikoff et al. (Proc. Natl. Acad. Sci. USA. 1982; 79: 1979-1983).
Robinson, L. J. et al., "NSF is required for transport from early to late endosomes," Journal of Cell Science, 110:2079-2087 (1997).
Rose, T. M. et al., "Primary Structure of the Human Melanoma-Associated Antigen P97 (Melanotransferrin) Deduced from the MRNA Sequence," Proc. Natl. Acad. Sci. USA, 83(5):12611265 (19861).
Saito, Y. et al., "Vector-mediated delivery of 1251-labeled beta-amyloid peptide A131-40 through the blood-brain barrier and binding to Alzheimer's disease amytoid of the 41-40/vector complex," Proc. NMI.
Sala, R. et al., "The Human Melanoma Associated Protein Melanotransferrin Promotes Endothelial Cell Migration and Angiogenesis in vivo," European Journal of Cell Biology, 81(11):599-607 (2002).
Sands, M. S., "Biodistribution, kinetics, and efficacy of highly phosphorylated and non-phosphorylated beta-glucuronidase in the murine model of mucopolysaccharidosis VII," Journal of Biological Chemistry. 276 (461:43160-43165 (20011).
Sato, K. et al., "Reshaping a human antibody to inhibit the interleukin 6-dependent tumor cell growth," Cancer Res., 53:851-856 (1993).
Shao, W. et al., "Inhibition of human tumor xenograft growth in nude mice by a conjugate of monoclonal antibody LA22 to epidermal growth factor receptor with anti-tumor antibiotics mitomycin C" Biochemical and Rionhysical Research Communications 2006 349:816-824.
Shi, N. et al., "Noninvasive gene targeting to the brain," Proc. Natl. Acad. Sci. USA, 97(13):75677572 (2000).
Skarlatos, S. et al., "Transport of [125]transferrin through the rat blood-brain barrier," Brain Research, 683 (2):164-171 (1995).
Song, B. W. et al., "Enhanced neuroprotective effects of basic fibroblast growth factor in regional brain ischemia after conjugation to a blood-brain barrier delivery vector," Journal of Pharmacology and Fxnerimental Theraneutics 301 (21.605-610 (20021).
Srinivasachar, K. et al., "New protein cross-linking reagents that are cleaved by mild acid," Biochem. 28:2501-2509 (1989).
Stefano, J. E. et al., "In vitro and in vivo evaluation of a non-carbohydrate targeting platform for lysosomal proteins," Journal of Controlled Release, 135:113-118 (2009).
Thom, G. et al., "A peptide derived from melanotransferrin delivers a protein-based interleukin I receptor antagonist across the BBB and ameliorates neuropathic pain in a preclinical model", Journal of Cerebral Rood Flow and Metabolism 0(00) 1-15 (2018).
Thomas, F. C. et al., "Uptake of ANG1005, a novel paclitaxel derivative, through the blood-brain barrier into brain and experimental brain metastases of breast cancer," Pharmaceutical Research, 26(111:2486-2494 (20091).
Vajdos et al. (J. Mol. Biol. Jul. 5, 2002; 320 (2): 415-428).
Winkler et al. (J. Immunol. Oct. 15, 2000; 165 (8): 4505-4514).

Woodbury, R. G. et al., "Identification of a cell surface protein, p. 97, in human melanomas and certain other neoplasms," Proc. Natl. Acad. Sci. USA, 77(4):2183-2187 (1980).
Wu, D. et al., "Pharmacokinetics and brain uptake of biotinylated basic fibroblast growth factor conjugated to a blood-brain barrier drug delivery system," Journal of Drug Targeting, 10(3):239-245 (20021).
International Search Report issued in corresponding PCT Patent Applicaton No. PCT/US2015/015662, dated Feb. 19, 2014.
Altenhofer, S. et al., "The NOX toolbox: validating the role of NADPH oxidases in physiology and disease," Cellular and Molecular Life Sciences, 69(14)2327-2343 (Jul. 2012).
Aktas, Y. et al., "Development and brain delivery of chitosan-PEG nanoparticles functionalized with the monoclonal antibody 0X26," Bioconjugate Chem,16(6):1503-1511 (2005).
Asano, N. et al., "In vitro inhibition and intracellular enhancement of lysosomal a-galactosidase A activity in Fabry lymphoblasts by 1-deoxygalactonojirimycin and its derivatives," Eur. J. Biochem., 2R7(1:11.417q-41RR onnn).
Begley, D. J. et al., "Lysosomal storage diseases and the blood-brain barrier," Current Pharmaceutical Design, 14 (16):1566-1580 (2008).
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cvtochemistry 42 (111'1493-1497 (19941).
Bickel, U. et al., "In vivo cleavability of a disulfide-based chimeric opioid peptide in rat brain," Bioconjugate Chem, 6 (2)211-218 (1995).
Bickel, U. et al., "Delivery of peptides and proteins through the blood-brain barrier," Advanced Drug Delivery Review, 16(1-3):247-279 (2001).
Bielicki, J. et al., "Human liver iduronate-2-sulfatase purification characterization and catalytic properties," Biochemical Journal, 271(1):75-86 (Oct. 1990).
Bielicki, J. et al., "Recombinant human iduronate-2-sulphatase: correction of mucopolysaccharidosis-type II fibroblasts and characterization of the purified enzyme," Biochemical Journal. 289(Pt. 11:241-246 (19931).
Blattler, W. A. et al., "New heterobifunctional protein cross-linking reagent that forms an acid-labile link," Biochem., 24:1517-1524 (1985).
Boado, R. J. et al., "Cloning and expression in Pichia pastoris of a genetically engineered single chain antibody against the rat transferrin receptor," Journal of Drug Targeting, 8(6):403-412 (2000).
Braulke et al., "Sorting of lysosomal proteins," Biochimica et Biophysica Acta, 1793:605-614 (2009).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin recentor" Fxnerimental Netirolonv.
Caldas et al. (Mol. Immunol. May 2003; 39 (15): 941-952).
Carter, P. et al., "Humanization of an anti-p185HER2 antibody for human cancer therapy," Proc. Natl. Acad. Sci. USA, 89:4285-4289 (1992).
Casset et al. (Biochem. Biophys. Res. Commun. Jul. 18, 2003; 307 (1): 198-205).
Chang et al. (Structure. Jan. 7, 2014; 22 (1): 9-21).
Chien et al. (Proc. Natl. Acad. Sci. USA. Jul. 1989; 86 (14): 5532-5536).
Cerletti, A. et al., "Endocytosis and transcytosis of an immunoliposome-based brain drug delivery system," Journal of Drug Targeting, 8(6):435-446 (2000).
Chen, Q. et al., "Efficient Synthesis of Doxorubicin Melanotransferrin p97 Conjugates Through SMCC Linker," Synthetic Communications, 34(13):2407-2414 (2004).
Chen, C.-H. B. et al., "Aptamer-based endocytosis of a lysosomal enzyme," Proceedings of the National Academy of Sciences, 105(41):15908-15913 (2008).

(56) References Cited

OTHER PUBLICATIONS

Co, M. S. et al., "Humanized antibodies for antiviral therapy," Proc. Natl. Acad. Sci. USA, 88(7):28692873 (1991).
Co, M. S. et al. "Chimeric and humanized antibodies with specificity for the CD33 antigen," J. Immunol., 148 (4):1149-1154 (1992).
Costantino, L. et al., "Is there a clinical future for polymeric nanoparticles as brain-targeting drug delivery agents?", Drug Discovery Today, 17(7-8):367-378 (Apr. 2012). Epub Nov. 7, 2011.
Daniele A. et al., "Uptake of recombinant iduronate-2-sulfatase into neuronal and glial cells in vitro," Biochimica et Thophysica Acta., 1588(3):203-209 (2002).
Deguchi, Y. et al., "Retention of biologic activity of human epidermal growth factor following conjugation to a blood-brain barrier drug delivery vector via an extended poly (ethylene glycol) linker," Bioconivaate Chem.. 10(11:32-37 (19991).
Delabarre, B. et al., "Central Pore Residues Mediate the p97/VCP activity required for ERAD," Molecular Cell, 22 (4):451-462 (2006).
Demeule, M. et al., "High transcytosis of melanotransferrin (P97) across the blood-brain barrier," Journal of Neurochemistry, 83:924-933 (2002).
Demeule, M. et al., "Regulation of plasminogen activation: A role for melantransferrin (p97) in cell migration," Blood, 102(5):1723-1731 (2003).
Di Natale, P. et al., "Iduronate sulfatase from human placenta," Biochimica et Biophysica Acta, 839(3):258-261 (May 1985).
De Pascalis et al. (J. Immunol. 2002; 169 (6): 3076-3084).
Dorr, R. T. et al., "In vitro rat myocyte cardiotoxicity model for antitumor antibiotics using adenosine triphosphate/protein ratios," Cancer Research, 48:5222-5227 (1988).
Friden, P. M., "Anti-transferrin receptor antibody and antibody-drug conjugates cross the blood-brain barrier," Proc. Natl. Acad. Sci. USA, 88(11):4771-4775 (1991).
Froissart, R. et al., "Processing of iduronate 2-sulphatase in human fibroblasts," Biochem. J., 309:425-430 (1995).
Gabathuler, Reinhard; "A natural solution to deliver medicine to brain"; Poster presented at the Drug Delivery & Formulation Summit; Apr. 2015; retrieved from http://www.ddfsummit.com/wp-content/uploads/2015/04/Reinhard-Gabathuler.pdf on Mar. 15, 2018.
Gabathuler, R. et al., "Incorporation of transcend (melanotransferrin or MTf) in a therapeutic antibody allows its transport across the blood-brain barrier for the treatment of brain disorders," Society for Neuroscience Abstract Viewer and Itinerary Planner, vol. 42 (2012), XP8173954, & 42nd Annual Meeting of the Society for Neuroscience, New Orleans, LA, USA, Oct. 13-17, 2012.
Gabathuler, R. et al., "BT2111, a new anticancer agent composed of trastuzumab and transcend a vector for brain delivery for the treatment of metastatic Her2+ breast cancer," [Abstract].7t-14 0. 4 of 4 4.
Geuze, H. J. et al., "Possible Pathways for Lysosomal Enzyme Delivery," Journal of Cell Biology, 101:2253-2262 (1985).
Gosk, S. et al., "Targeting anti-transferrin receptor antibody (0X26) and 0X26-conjugated liposomes to brain capillary endothelial cells using in situ perfusion," Journal of Cerebral Blood Flow & Metabolism. 24(111:1193-1204 (20041).
Grubb, J. H. et al., "Chemically modified 13-glucuronidase crosses blood-brain barrier and clears neuronal storage in murine mucopolysaccharidosis VII," Proceedings of the National Academy of SniAnr. AR 1115(71.2R1R-2R21 onnm.
Giusti et al. (Proc. Natl. Acad. Sci. USA. May 1987; 84 (9): 2926-2930).
Holliger, P. et al., "'Diabodies': Small bivalent and bispecific antibody fragments," Proc. Natl. Acad. Sci., 90:6444-6448 (1993).
Holm et al. (Mol. Immunol. Feb. 2007; 44 (6): 1075-1084).
Hu, S. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res., 56:3055-3061 (19961).
Huston, J. S. et al., "Protein engineering of antibody binding sites: recovery of specific activity in an anti-digoxin single-chain Fv analogue produced in *Escherichia coil*," Proc. Natl. Acad. Sci. USA, 85(161:5879-5883 (19881).
Huwyler, J. et al., "Receptor mediated delivery of daunomycin using immunoliposomes: pharmacokinetics and tissue distribution in the rat," Journal of Phamacology & Experimental Therapeutics. 282(31:1541-1546 (19971).
Inoue, T. et al., "Predictive in vitro cardiotoxicity and hepatotoxicity screening system using neonatal rat heart cells and rat hepatocytes," AATEX 14, Special Issue, Proc. 6th World Congress on Alternatives & Animal Use in the life Sciences nn 457-462 (Aug. 21-25, 20071).
Jefferies, W. A. et al., "Transferrin receptor on endothelium of brain capillaries," Nature, 312:162163 (1984).
Jefferies, W. A. et al., "Analysis of lymphopoletic stem cells with a monoclonal antibody to the rat transferrin receptor," Immunology, 54(2):333-341 (1985).

\* cited by examiner

FIG. 1A
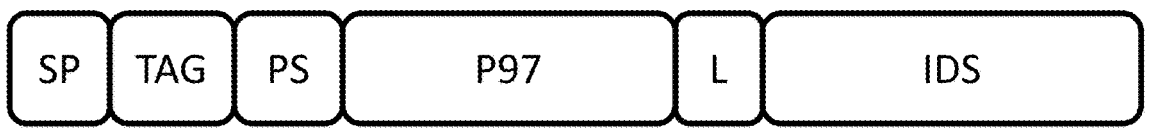
FIG. 1B
*FIG. 1*

P97-IDS FUSION PROTEINS

CROSS-REFERENCE TO RELATED APPLICATIONS

This application is a continuation of U.S. application Ser. No. 15/119,293 filed Aug. 16, 2016, which is a national stage application under 35 U.S.C. 371 of international application no. PCT/US2015/015662, filed Feb. 15, 2015, which claims priority under 35 U.S.C. § 119(e) to U.S. Provisional Application No. 61/941,896, filed Feb. 19, 2015, each of which are incorporated by reference in their its entirety.

SEQUENCE LISTING

The Sequence Listing associated with this application is provided in text format in lieu of a paper copy, and is hereby incorporated by reference into the specification. The name of the text file containing the Sequence Listing is BIOA_009_01WO_ST25.txt. The text file is about 153 KB, was created on Feb. 9, 2015, and was submitted electronically via EFS-Web in the file of application Ser. No. 15/119,293 filed Aug. 16, 2016.

BACKGROUND

Technical Field

The present invention relates to fusion proteins between p97 (melanotransferrin) and iduronate-2-sulfatase (IDS), and related compositions and methods of use thereof, for instance, to facilitate delivery of IDS across the blood-brain barrier (BBB) and/or improve its tissue penetration in CNS and/or peripheral tissues, and thereby treat and/or diagnose Hunter Syndrome (Mucopolysaccharidosis type II; MPS II) and related lysosomal storage disorders, including those having a central nervous system (CNS) component.

Description of the Related Art

Lysosomal storage diseases (LSDs) result from the absence or reduced activity of specific enzymes or proteins within the lysosomes of a cell. Within cells, the effect of the missing enzyme activity can be seen as an accumulation of un-degraded "storage material" within the intracellular lysosome. This build-up causes lysosomes to swell and malfunction, resulting in cellular and tissue damage. As lysosomal storage diseases typically have a genetic etiology, many tissues will lack the enzyme in question. However, different tissues suffer the absence of the same enzyme activity differently. How adversely a tissue will be affected is determined, to some extent, by the degree to which that tissue generates the substrate of the missing enzyme. The types of tissue most burdened by storage, in turn, dictate how the drug should be administered to the patient.

A large number of lysosomal storage disease enzymes have been identified and correlated with their respective diseases. Once the missing or deficient enzyme has been identified, treatment can focus on the problem of effectively delivering the replacement enzyme to a patient's affected tissues. Hunter Syndrome or Mucopolysaccharidosis type II (MPS II) is a lysosomal storage disorders (LSD) caused by a deficiency in iduronate-2-sulfatase (I2S or IDS). I2S is a lysosomal enzyme responsible for the metabolism of mucopolysaccharides. Deficiency in the enzyme activity leads a variety of pathologies ultimately and premature death. Enzyme replacement therapy (ERT) with recombinant I2S (Elaprase®) can treat peripheral symptoms but patients suffer eventually from dementia because the enzyme cannot cross the blood brain barrier (BBB).

Intravenous enzyme replacement therapy (ERT) can be beneficial for LSDs such as MPSII. However, means for enhancing the delivery of the therapeutic enzyme to the lysosome in such diseases would be advantageous in terms of reduced cost and increased therapeutic efficacy.

As one problem, the blood-brain barrier (BBB) blocks the free transfer of many agents from blood to brain. For this reason, LSDs that present with significant neurological aspect are not expected to be as responsive to intravenous ERT. For such diseases, methods of improving the delivery of the enzyme across the BBB and into the lysosomes of the affected cells would be highly desirable.

BRIEF SUMMARY

Embodiments of the present invention include p97 (melanotransferrin or MTf) fusion proteins, comprising an iduronate-2-sulfatase (IDS or I2S) polypeptide fused to a p97 polypeptide and an optional peptide linker (L) in between.

In some embodiments, the IDS polypeptide is fused to the N-terminus of the p97 polypeptide. In certain embodiments, the IDS polypeptide is fused to the C-terminus of the p97 polypeptide.

Certain fusion proteins comprise the peptide linker in between. In certain embodiments, the peptide linker is selected from one or more of a rigid linker, a flexible linker, and an enzymatically-cleavable linker. In certain embodiments, the peptide linker is a rigid linker, optionally comprising the sequence (EAAAK)$_{1-3}$ (SEQ ID NOS:36-38), such as EAAAKEAAAKEAAAK (SEQ ID NO:38). In some embodiments, the peptide linker is a flexible linker. In certain embodiments, the peptide linker is an enzymatically-cleavable linker.

In certain embodiments, the fusion protein comprises an N-terminal signal peptide (SP) sequence, optionally selected from Table 4. In some embodiments, the fusion protein comprises the structure: (a) SP-IDS-L-p97 or (b) SP-p97-L-IDS.

In particular embodiments, the SP comprises the sequence MEWSWVFLFFLSVTTGVHS (SEQ ID NO:149) and the p97 fusion protein comprises the structure: (a) SP-p97-IDS or (b) SP-p97-L-IDS.

In certain embodiments, the SP comprises the human p97 SP sequence MRGPSGALWLLLALRTVLG (SEQ ID NO:39) and the p97 fusion protein comprises the structure: (a) SP-p97-IDS or (b) SP-p97-L-IDS.

In certain embodiments, the SP comprises the human IDS SP sequence MPPPRTGRGLLWLGLVLSSVCVALG (SEQ ID NO:40) and the p97 fusion protein comprises the structure: (a) SP-IDS-p97 or (b) SP-IDS-L-p97.

In some embodiments, the fusion protein comprises a purification tag (TAG), optionally selected from Table 5. In certain embodiments, the fusion protein comprises the structure: (a) SP-TAG-IDS-L-p97 or (b) SP-TAG-p97-L-IDS. In certain embodiments, the tag comprises a poly-histidine tag, optionally a 10× poly-histidine tag. In some embodiments, the tag comprises a FLAG tag DYKDDDDK (SEQ ID NO:122). In specific embodiments, the tag comprises a poly-histidine tag, for example, a 10× poly-histidine tag, and a FLAG tag.

In certain embodiments, the fusion protein comprises a protease site (PS), optionally selected from Table 6. In particular embodiments, the fusion protein comprises the structure: (a) SP-TAG-PS-IDS-L-p97 or (b) SP-TAG-PSp97-linker-IDS. In specific embodiments, the PS site comprises the TEV protease site ENLYFQG (SEQ ID NO:135).

In certain embodiments, the fusion protein comprises the structure (a) SP (MEWSWVFLFFLSVTTGVHS; SEQ ID NO:149)-HIS TAG-TEV PS-IDS-Rigid L-p97 or (b) SP (MEWSWVFLFFLSVTTGVHS; SEQ ID NO: 149)-HIS TAG-TEV PS-p97-Rigid L-IDS.

In specific embodiments, the fusion protein comprises the structure (a) SP (MEWSWVFLFFLSVTTGVHS; SEQ ID NO: 149)-HIS TAG-TEV PS-IDS-(EAAAK; SEQ ID NO: 36)$_3$-p97 or (b) SP (MEWSWVFLFFLSVTTGVHS; SEQ ID NO: 149)-HIS TAG-TEV PS-p97-(EAAAK; SEQ ID NO: 36)$_3$-IDS.

In certain embodiments, the fusion protein comprises the structure (a) IDS SP-HIS TAG-TEV PS-IDS-Rigid L-p97 or (b) p97 SP-HIS TAG-TEV PS-p97-Rigid L-IDS.

In particular embodiments, the fusion protein comprises the structure (a) IDS SP-10×HIS TAG-TEV PS-IDS-(EAAAK; SEQ ID NO: 36)$_3$-p97 (SEQ ID NO:29) or (b) p97 SP-10×HIS TAG-TEV PS-p97-(EAAAK; SEQ ID NO: 36)$_3$-IDS (SEQ ID NO:30).

In certain embodiments, the IDS polypeptide comprises, consists, or consists essentially of (a) an amino acid sequence set forth in SEQ ID NOs:31-35; (b) an amino acid sequence at least 90% identical to a sequence set forth in SEQ ID NOs:31-35; (c) or an amino acid sequence that differs from SEQ ID NOs:31-35 by addition, substitution, insertion, or deletion of about 1-50 amino acids. In some embodiments, the IDS polypeptide comprises, consists, or consists essentially of the amino acid sequence set forth in SEQ ID NO:32 or 33.

In certain embodiments, the p97 polypeptide comprises, consists, or consists essentially of (a) an amino acid sequence set forth in SEQ ID NOs:1-28; (b) an amino acid sequence at least 90% identical to a sequence set forth in SEQ ID NOs: 1-28; (c) or an amino acid sequence that differs from SEQ ID NOs: 1-28 by addition, substitution, insertion, or deletion of about 1-50 amino acids. In particular embodiments, the p97 polypeptide comprises, consists, or consists essentially of the amino acid sequence set forth in SEQ ID NO:2 (soluble human p97) or SEQ ID NO:14 or 148 (MTfpep).

In certain embodiments, the fusion protein comprises, consists, or consists essentially of (a) an amino acid sequence set forth in SEQ ID NO: 138-142 or 29-30; (b) an amino acid sequence at least 90% identical to a sequence set forth in SEQ ID NO: 138-142 or 29-30; (c) or an amino acid sequence that differs from SEQ ID NO: 138-142 or 29-30 by addition, substitution, insertion, or deletion of about 1-50 amino acids. In specific embodiments, the fusion protein comprises, consists, or consists essentially of an amino acid sequence set forth in SEQ ID NO: 138-142 or 29-30.

Also included are isolated polynucleotides which encodes a p97 fusion protein described herein. In some embodiments, the isolated polynucleotide is codon-optimized for expression in a host cell. In certain embodiments, the host cell is a mammalian cell, an insect cell, a yeast cell, or a bacterial cell. In particular embodiments, the polynucleotide comprises a sequence selected from SEQ ID NOs:143-147.

Some embodiments include recombinant host cells, comprising an isolated polynucleotide described herein, where the isolated polynucleotide is operably linked to one or more regulatory elements.

Also included are vectors, comprising an isolated polynucleotide that encodes a p97 fusion protein described herein, which is operably linked to one or more regulatory elements.

Also included are recombinant host cells, comprising a vector, isolated polynucleotide, and/or p97 fusion protein described herein. In certain embodiments, the host cell is a mammalian cell, an insect cell, a yeast cell, or a bacterial cell. In specific embodiments, the mammalian cell is a Chinese hamster ovary (CHO) cell, a HEK-293 cell, or a HT-1080 human fibrosarcoma cell.

Certain embodiments include pharmaceutical compositions, comprising a pharmaceutically-acceptable carrier and a p97 fusion protein described herein, where the pharmaceutical composition is sterile and non-pyrogenic.

Also included are methods for the treatment of a lysosomal storage disease in a subject in need thereof, comprising administering to the subject a p97 fusion protein or pharmaceutical composition described herein. In certain embodiments, the lysosomal storage disease is Hunter Syndrome (MPS II). In certain embodiments, the lysosomal storage disease has central nervous system (CNS) involvement. In certain embodiments, the subject is at risk for developing CNS involvement of the lysosomal storage disease. In certain embodiments, the subject is a human male. In certain embodiments, the p97 fusion protein or pharmaceutical composition is administered by intravenous (IV) infusion or intraperitoneal (IP) injection.

BRIEF DESCRIPTION OF THE DRAWINGS

FIGS. 1A and 1B illustrate the general structure of exemplary fusion proteins having a signal peptide (SP), purification or affinity tag (TAG), protease site (PS) for removal of the SP and TAG, p97 (melanotransferrin) polypeptide, a linker (L), and an iduronate-2-sulfatase (IDS) polypeptide.

DETAILED DESCRIPTION

Figure 2:
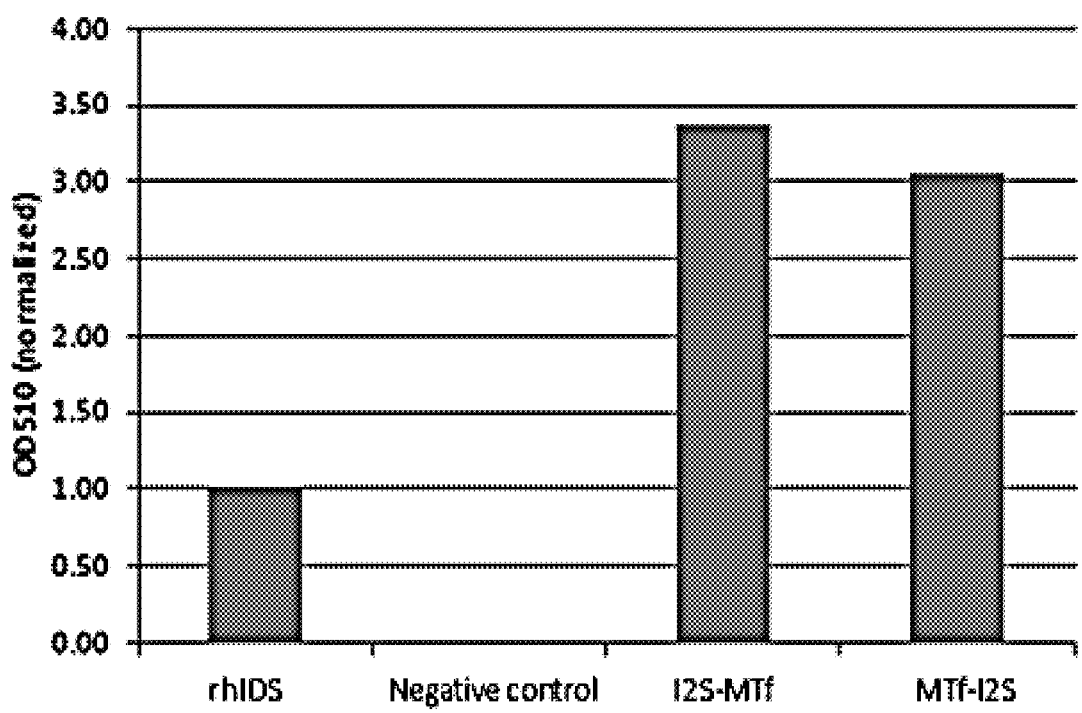
FIG. 2 shows the enzyme activity evaluation of I2S-MTf and MTf-I2S fusion proteins as measured by their ability to hydrolyze the substrate 4-Nitrocatechol Sulfate (PNCS) relative to recombinant human IDS and negative control (TZM-MTf fusion). 1 ug of each sample was used in the enzyme activity assay, and data presented are normalized to rhIDS.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al.,

*Molecular Cloning: A Laboratory Manual* (3rd Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5th Ed. Hoboken N.J., John Wiley & Sons; B. Perbal, *A Practical Guide to Molecular Cloning* (3rd Edition 2010); Farrell, R., *RNA Methodologies: A Laboratory Guide for Isolation and Characterization* (3rd Edition 2005).

All publications, patents, and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, certain exemplary methods and materials are described herein. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent or non-covalent attachment or linkage of an agent or other molecule, e.g., a biologically active molecule, to a p97 polypeptide or p97 sequence. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research*. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "linkage," "linker," "linker moiety," or "L" is used herein to refer to a linker that can be used to separate a p97 polypeptide from an agent of interest, or to separate a first agent from another agent, for instance where two or more agents are linked to form a p97 conjugate or fusion protein. The linker may be physiologically stable or may include a releasable linker such as an enzymatically degradable linker (e.g., proteolytically cleavable linkers). In certain aspects, the linker may be a peptide linker, for instance, as part of a p97 fusion protein. In some aspects, the linker may be a non-peptide linker or non-proteinaceous linker. In some aspects, the linker may be particle, such as a nanoparticle.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of a fusion protein of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the enzymatic activity, the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, of a p97 fusion protein relative to the agent/protein alone. Other examples of comparisons and "statistically significant" amounts are described herein.

In certain embodiments, the "purity" of any given agent (e.g., a p97 conjugate such as a fusion protein) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Hα), as the driving force. For purposes herein, a "releasable linker" is synonymous with a "degradable linker." An "enzymatically degradable linkage" includes a linkage, e.g., amino acid sequence that is subject to degradation by one or more enzymes, e.g., peptidases or proteases. In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99%, or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a protein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a p97 polypeptide fusion protein has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a p97 fusion protein of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

Fusion Proteins

Embodiments of the present invention relate generally to fusion proteins that comprise a human p97 (melanotransferrin; MTf) polypeptide sequence and a iduronate-2-sulfatase (IDS or I2S) polypeptide sequence, polynucleotides encoding the fusion proteins, host cells and methods of producing fusion proteins, and related compositions and methods of use thereof. Exemplary fusion proteins (e.g., Table 1), p97 polypeptide sequences (e.g., Table 2), and IDS polypeptide sequences (e.g., Table 3) are described herein. The terms "p97" and "MTf" are used interchangeably herein, as are the terms "IDS" and "I2S."

Also described are exemplary methods and components for coupling a p97 polypeptide sequence to an IDS sequence. In certain embodiments, the p97 fusion protein comprises one or more signal peptide sequences (SP), purification tags (TAG), protease cleavage sites (PS), and/or peptide linkers (L), including any combination of the foregoing, examples of which are provided herein. Variants and fragments of any of the foregoing are also described herein.

In certain embodiments, the p97 fusion protein comprises, consists, or consists essentially of at least one of the configurations illustrated below (N-terminus>C-terminus):

IDS-p97
p97-IDS
IDS-L-p97
p97-L-IDS
SP-IDS-p97
SP-p97-IDS
SP-IDS-L-p97
SP-P97-L-IDS
SP-PS-IDS-p97
SP-PS-P97-IDS
SP-PS-IDS-L-p97
SP-PS-p97-L-IDS
SP-TAG-PS-IDS-p97
SP-TAG-PS-p97-IDS
SP-TAG-PS-IDS-L-p97
SP-TAG-PS-p97-L-IDS
TAG-IDS-p97
TAG-p97-IDS
TAG-IDS-L-p97
TAG-p97-L-IDS
TAG-PS-IDS-p97
TAG-PS-p97-IDS
TAG-PS-IDS-L-p97
TAG-PS-p97-L-IDS
IDS SP-HIS TAG-TEV PS-IDS-Rigid L-p97
IDS SP-HIS TAG-TEV PS-IDS-(EAAAK)$_3$-p97
p97 SP-HIS TAG-TEV PS-p97-Rigid L-IDS
p97 SP-HIS TAG-TEV PS-p97-(EAAAK)$_3$-IDS Fusion proteins of these and related configurations can be constructed using any of the IDS, p97, L, SP, TAG, or PS sequences described herein, including functional or active variants and fragments thereof.

Specific examples of p97 fusion proteins are illustrated in Table 1 below.

TABLE 1

Exemplary p97 Fusion Proteins

| Description | Sequence | SEQ ID NO: |
|---|---|---|
| IDS SP- 10xHIS TAG- TEV PS-IDS- Rigid L-p97 | MPPPRTGRGLLWLGLVLSSVCVALGHHHHHHHHHHENLYFQSETQANST TDALNVLLIIVDDLRPSLGCYGDKLVRSPNIDQLASHSLLFQNAFAQQA VCAPSRVSFLTGRRPDTTRLYDFNSYWRVHAGNFSTIPQYFKENGYVTM SVGKVFHPGISSNHTDDSPYSWSFPPYHPSSEKYENTKTCRGPDGELHA NLLCPVDVLDVPEGTLPDKQSTEQAIQLLEKMKTSASPFFLAVGYHKPH IPFRYPKEFQKLYPLENITLAPDPEVPDGLPPVAYNPWMDIRQREDVQA LNISVPYGPIPVDFQRKIRQSYFASVSYLDTQVGRLLSALDDLQLANST IIAFTSDHGWALGEHGEWAKYSNFDVATHVPLIFYVPGRTASLPEAGEK LFPYLDPFDSASQLMEPGRQSMDLVELVSLFPTLAGLAGLQVPPRCPVP SFHVELCREGKNLLKHFRFRDLEEDPYLPGNPRELIAYSQYPRPSDIPQ WNSDKPSLKDIKIMGYSIRTIDYRYTVWVGFNPDEFLANFSDIHAGELY FVDSDPLQDHNMYNDSQGGDLFQLLMPEAAAKEAAAKEAAAKGMEVRWC ATSDPEQHKCGNMSEAFREAGIQPSLLCVRGTSADHCVQLIAAQEADAI TLDGGAIYEAGKEHGLKPVVGEVYDQEVGTSYYAVAVVRRSSHVTIDTL KGVKSCHTGINRTVGWNVPVGYLVESGRLSVMGCDVLKAVSDYFGGSCV PGAGETSYSESLCRLCRGDSSGEGVCDKSPLERYYDYSGAFRCLAEGAG DVAFVKHSTVLENTDGKTLPSWGQALLSQDFELLCRDGSRADVTEWRQC HLARVPAHAVVVRADTDGGLIFRLLNEGQRLFSHEGSSFQMFSSEAYGQ KDLLFKDSTSELVPIATQTYEAWLGHEYLHAMKGLLCDPNRLPPYLRWC VLSTPEIQKCGDMAVAFRRQRLKPEIQCVSAKSPQHCMERIQAEQVDAV TLSGEDIYTAGKTYGLVPAAGEHYAPEDSSNSYYVVAVVRRDSSHAFTL DELRGKRSCHAGFGSPAGWDVPVGALIQRGFIRPKDCDVLTAVSEFFNA SCVPVNNPKNYPSSLCALCVGDEQGRNKCVGNSQERYYGYRGAFRCLVE NAGDVAFVRHTTVFDNTNGHNSEPWAAELRSEDYELLCPNGARAEVSQF AACNLAQIPPHAVMVRPDTNIFTVYGLLDKAQDLFGDDHNKNGFKMFDS SNYHGQDLLFKDATVRAVPVGEKTTYRGWLGLDYVAALEGMSSQQCS | 29 |
| P97 SP- 10xHIS TAG- TEV PS-p97- Rigid L-IDS | MRGPSGALWLLLALRTVLGHHHHHHHHHHENLYFQGMEVRWCATSDPEQ HKCGNMSEAFREAGIQPSLLCVRGTSADHCVQLIAAQEADAITLDGGAI YEAGKEHGLKPVVGEVYDQEVGTSYYAVAVVRRSSHVTIDTLKGVKSCH TGINRTVGWNVPVGYLVESGRLSVMGCDVLKAVSDYFGGSCVPGAGETS YSESLCRLCRGDSSGEGVCDKSPLERYYDYSGAFRCLAEGAGDVAFVKH STVLENTDGKTLPSWGQALLSQDFELLCRDGSRADVTEWRQCHLARVPA HAVVVRADTDGGLIFRLLNEGQRLFSHEGSSFQMFSSEAYGQKDLLFKD STSELVPIATQTYEAWLGHEYLHAMKGLLCDPNRLPPYLRWCVLSTPEI QKCGDMAVAFRRQRLKPEIQCVSAKSPQHCMERIQAEQVDAVTLSGEDI YTAGKTYGLVPAAGEHYAPEDSSNSYYVVAVVRRDSSHAFTLDELRGKR SCHAGFGSPAGWDVPVGALIQRGFIRPKDCDVLTAVSEFFNASCVPVNN PKNYPSSLCALCVGDEQGRNKCVGNSQERYYGYRGAFRCLVENAGDVAF VRHTTVFDNTNGHNSEPWAAELRSEDYELLCPNGARAEVSQFAACNLAQ IPPHAVMVRPDTNIFTVYGLLDKAQDLFGDDHNKNGFKMFDSSNYHGQD LLFKDATVRAVPVGEKTTYRGWLGLDYVAALEGMSSQQCSEAAAKEAAA KEAAAKSETQANSTTDALNVLLIIVDDLRPSLGCYGDKLVRSPNIDQLA SHSLLFQNAFAQQAVCAPSRVSFLTGRRPDTTRLYDFNSYWRVHAGNFS TIPQYFKENGYVTMSVGKVFHPGISSNHTDDSPYSWSFPPYHPSSEKYE NTKTCRGPDGELHANLLCPVDVLDVPEGTLPDKQSTEQAIQLLEKMKTS ASPFFLAVGYHKPHIPFRYPKEFQKLYPLENITLAPDPEVPDGLPPVAY NPWMDIRQREDVQALNISVPYGPIPVDFQRKIRQSYFASVSYLDTQVGR LLSALDDLQLANSTIIAFTSDHGWALGEHGEWAKYSNFDVATHVPLIFY VPGRTASLPEAGEKLFPYLDPFDSASQLMEPGRQSMDLVELVSLFPTLA GLAGLQVPPRCPVPSFHVELCREGKNLLKHFRFRDLEEDPYLPGNPREL IAYSQYPRPSDIPQWNSDKPSLKDIKIMGYSIRTIDYRYTVWVGFNPDE FLANFSDIHAGELYFVDSDPLQDHNMYNDSQGGDLFQLLMP | 30 |
| I2S-MTf (SP: Flag TAG and 10xHIS TAG: TEV PS: IDS: Rigid L: Soluble p97) | MEWSWVFLFFLSVTTGVHSDYKDDDDKEQKLISEEDLHHHHHHHHHHGG GGENLYFQGSETQANSTTDALNVLLIIVDDLRPSLGCYGDKLVRSPNID QLASHSLLFQNAFAQQAVCAPSRVSFLTGRRPDTTRLYDFNSYWRVHAG NFSTIPQYFKENGYVTMSVGKVFHPGISSNHTDDSPYSWSFPPYHPSSE KYENTKTCRGPDGELHANLLCPVDVLDVPEGTLPDKQSTEQAIQLLEKM KTSASPFFLAVGYHKPHIPFRYPKEFQKLYPLENITLAPDPEVPDGLPP VAYNPWMDIRQREDVQALNISVPYGPIPVDFQRKIRQSYFASVSYLDTQ VGRLLSALDDLQLANSTIIAFTSDHGWALGEHGEWAKYSNFDVATHVPL IFYVPGRTASLPEAGEKLFPYLDPFDSASQLMEPGRQSMDLVELVSLFP TLAGLAGLQVPPRCPVPSFHVELCREGKNLLKHFRFRDLEEDPYLPGNP RELIAYSQYPRPSDIPQWNSDKPSLKDIKIMGYSIRTIDYRYTVWVGFN PDEFLANFSDIHAGELYFVDSDPLQDHNMYNDSQGGDLFQLLMPEAAAK EAAAKEAAAKGMEVRWCATSDPEQHKCGNMSEAFREAGIQPSLLCVRGT SADHCVQLIAAQEADAITLDGGAIYEAGKEHGLKPVVGEVYDQEVGTSY YAVAVVRRSSHVTIDTLKGVKSCHTGINRTVGWNVPVGYLVESGRLSVM GCDVLKAVSDYFGGSCVPGAGETSYSESLCRLCRGDSSGEGVCDKSPLE RYYDYSGAFRCLAEGAGDVAFVKHSTVLENTDGKTLPSWGQALLSQDFE LLCRDGSRADVTEWRQCHLARVPAHAVVVRADTDGGLIFRLLNEGQRLF SHEGSSFQMFSSEAYGQKDLLFKDSTSELVPIATQTYEAWLGHEYLHAM KGLLCDPNRLPPYLRWCVLSTPEIQKCGDMAVAFRRQRLKPEIQCVSAK SPQHCMERIQAEQVDAVTLSGEDIYTAGKTYGLVPAAGEHYAPEDSSNS | 138 |

TABLE 1-continued

Exemplary p97 Fusion Proteins

| Description | Sequence | SEQ ID NO: |
|---|---|---|
| | YVVVAVVRRDSSHAFTLDELRGKRSCHAGFGSPAGWDVPVGALIQRGFI<br>RPKDCDVLTAVSEFFNASCVPVNNPKNYPSSLCALCVGDEQGRNKCVGN<br>SQERYYGYRGAFRCLVENAGDVAFVRHTTVFDNTNGHNSEPWAAELRSE<br>DYELLCPNGARAEVSQFAACNLAQIPPHAVMVRPDTNIFTVYGLLDKAQ<br>DLFGDDHNKNGFKMFDSSNYHGQDLLFKDATVRAVPVGEKTTYRGWLGL<br>DYVAALEGMSSQQCS | |
| MTf-I2S<br>(SP: Flag<br>TAG and<br>10xHIS TAG:<br>TEV PS:<br>Soluble p97<br>Rigid L:<br>IDS) | MEWSWVFLFFLSVTTGVHSDYKDDDDKEQKLISEEDLHHHHHHHHHHGG<br>GGENLYFQGMEVRWCATSDPEQHKCGNMSEAFREAGIQPSLLCVRGTS<br>ADHCVQLIAAQEADAITLDGGAIYEAGKEHGLKPVVGEVYDQEVGTSYY<br>AVAVVRRSSHVTIDTLKGVKSCHTGINRTVGWNVPVGYLVESGRLSVMG<br>CDVLKAVSDYFGGSCVPGAGETSYSESLCRLCRGDSSGEGVCDKSPLER<br>YYDYSGAFRCLAEGAGDVAFVKHSTVLENTDGKTLPSWGQALLSQDFEL<br>LCRDGSRADVTEWRQCHLARVPAHAVVVRADTDGGLIFRLLNEGQRLFS<br>HEGSSFQMFSSEAYGQKDLLFKDSTSELVPIATQTYEAWLGHEYLHAMK<br>GLLCDPNRLPPYLRWCVLSTPEIQKCGDMAVAFRRQRLKPEIQCVSAKS<br>PQHCMERIQAEQVDAVTLSGEDIYTAGKTYGLVPAAGEHYAPEDSSNSY<br>YVVAVVRRDSSHAFTLDELRGKRSCHAGFGSPAGWDVPVGALIQRGFIR<br>PKDCDVLTAVSEFFNASCVPVNNPKNYPSSLCALCVGDEQGRNKCVGNS<br>QERYYGYRGAFRCLVENAGDVAFVRHTTVFDNTNGHNSEPWAAELRSED<br>YELLCPNGARAEVSQFAACNLAQIPPHAVMVRPDTNIFTVYGLLDKAQD<br>LFGDDHNKNGFKMFDSSNYHGQDLLFKDATVRAVPVGEKTTYRGWLGLD<br>YVAALEGNSSQQCSEAAAKEAAAKEAAAKSETQANSTTDALNVLLIIVD<br>DLRPSLGCYGDKLVRSPNIDQLASHSLLFQNAFAQQAVCAPSRVSFLTG<br>RRPDTTRLYDFNSYWRVHAGNFSTIPQYFKENGYVTMSVGKVFHPGISS<br>NHTDDSPYSWSFPPYHPSSEKYENTKTCRGPDGELHANLLCPVDVLDVP<br>EGTLPDKQSTEQAIQLLEKMKTSASPFFLAVGYHKPHIPFRYPKEFQKL<br>YPLENITLAPDPEVPDGLPPVAYNPWMDIRQREDVQALNISVPYGPIPV<br>DFQRKIRQSYFASVSYLDTQVGRLLSALDDLQLANSTIIAFTSDHGWAL<br>GEHGEWAKYSNFDVATHVPLIFYVPGRTASLPEAGEKLFPYLDPFDSAS<br>QLMEPGRQSMDLVELVSLFPTLAGLAGLQVPPRCPVPSFHVELCREGKN<br>LLKHFRFRDLEEDPYLPGNPRELIAYSQYPRPSDIPQWNSDKPSLKDIK<br>IMGYSIRTIDYRYTVWVGFNPDEFLANFSDIHAGELYFVDSDPLQDHNM<br>YNDSQGGDLFQLLMP | 139 |
| MTfpep-I2S<br>(SP: Flag<br>TAG and<br>10xHIS TAG:<br>TEV PS:<br>MTfpep w/C-<br>terminal Y:<br>Rigid L:<br>I2S) | MEWSWVFLFFLSVTTGVHSDYKDDDDKEQKLISEEDLHHHHHHHHHHGG<br>GGENLYFQGDSSHAFTLDELRYEAAAKEAAAKEAAAKSETQANSTTDAL<br>NVLLIIVDDLRPSLGCYGDKLVRSPNIDQLASHSLLFQNAFAQQAVCAP<br>SRVSFLTGRRPDTTRLYDFNSYWRVHAGNFSTIPQYFKENGYVTMSVGK<br>VFHPGISSNHTDDSPYSWSFPPYHPSSEKYENTKTCRGPDGELHANLLC<br>PVDVLDVPEGTLPDKQSTEQAIQLLEKMKTSASPFFLAVGYHKPHIPFR<br>YPKEFQKLYPLENITLAPDPEVPDGLPPVAYNPWMDIRQREDVQALNIS<br>VPYGPIPVDFQRKIRQSYFASVSYLDTQVGRLLSALDDLQLANSTIIAF<br>TSDHGWALGEHGEWAKYSNFDVATHVPLIFYVPGRTASLPEAGEKLFPY<br>LDPFDSASQLMEPGRQSMDLVELVSLFPTLAGLAGLQVPPRCPVPSFHV<br>ELCREGKNLLKHFRFRDLEEDPYLPGNPRELIAYSQYPRPSDIPQWNSD<br>KPSLKDIKIMGYSIRTIDYRYTVWVGFNPDEFLANFSDIHAGELYFVDS<br>DPLQDHNMYNDSQGGDLFQLLMP | 140 |
| I2S-MTfpep<br>(SP: Flag<br>TAG and<br>10xHIS TAG:<br>TEV PS: I2S:<br>Rigid L:<br>MTfpep w/C-<br>terminal Y) | MEWSWVFLFFLSVTTGVHSDYKDDDDKEQKLISEEDLHHHHHHHHHHGG<br>GGENLYFQGSETQANSTTDALNVLLIIVDDLRPSLGCYGDKLVRSPNID<br>QLASHSLLFQNAFAQQAVCAPSRVSFLTGRRPDTTRLYDFNSYWRVHAG<br>NFSTIPQYFKENGYVTMSVGKVFHPGISSNHTDDSPYSWSFPPYHPSSE<br>KYENTKTCRGPDGELHANLLCPVDVLDVPEGTLPDKQSTEQAIQLLEKM<br>KTSASPFFLAVGYHKPHIPFRYPKEFQKLYPLENITLAPDPEVPDGLPP<br>VAYNPWMDIRQREDVQALNISVPYGPIPVDFQRKIRQSYFASVSYLDTQ<br>VGRLLSALDDLQLANSTIIAFTSDHGWALGEHGEWAKYSNFDVATHVPL<br>IFYVPGRTASLPEAGEKLFPYLDPFDSASQLMEPGRQSMDLVELVSLFP<br>TLAGLAGLQVPPRCPVPSFHVELCREGKNLLKHFRFRDLEEDPYLPGNP<br>RELIAYSQYPRPSDIPQWNSDKPSLKDIKIMGYSIRTIDYRYTVWVGFN<br>PDEFLANFSDIHAGELYFVDSDPLQDHNMYNDSQGGDLFQLLMPEAAAK<br>EAAAKEAAAKDSSHAFTLDELRY | 141 |
| I2S-MTfpep<br>(without<br>propep of<br>I2S<br>SP: Flag<br>TAG and<br>10xHIS TAG:<br>TEV PS: I2S<br>w/o propep:<br>Rigid L: | MEWSWVFLFFLSVTTGVHSDYKDDDDKEQKLISEEDLHHHHHHHHHHGG<br>GGENLYFQGTDALNVLLIIVDDLRPSLGCYGDKLVRSPNIDQLASHSLL<br>FQNAFAQQAVCAPSRVSFLTGRRPDTTRLYDFNSYWRVHAGNFSTIPQY<br>FKENGYVTMSVGKVFHPGISSNHTDDSPYSWSFPPYHPSSEKYENTKTC<br>RGPDGELHANLLCPVDVLDVPEGTLPDKQSTEQAIQLLEKMKTSASPFF<br>LAVGYHKPHIPFRYPKEFQKLYPLENITLAPDPEVPDGLPPVAYNPWMD<br>IRQREDVQALNISVPYGPIPVDFQRKIRQSYFASVSYLDTQVGRLLSAL<br>DDLQLANSTIIAFTSDHGWALGEHGEWAKYSNFDVATHVPLIFYVPGRT<br>ASLPEAGEKLFPYLDPFDSASQLMEPGRQSMDLVELVSLFPTLAGLAGL<br>QVPPRCPVPSFHVELCREGKNLLKHFRFRDLEEDPYLPGNPRELIAYSQ | 142 |

TABLE 1-continued

Exemplary p97 Fusion Proteins

| Description | Sequence | SEQ ID NO: |
|---|---|---|
| MTfpep w/C-terminal Y) | YPRPSDIPQWNSDKPSLKDIKIMGYSIRTIDYRYTVWVGFNPDEFLANF SDIHAGELYFVDSDPLQDHNMYNDSQGGDLFQLLMPEAAAKEAAAKEAA AKDSSHAFTLDELRY | |

Thus, in some embodiments, the fusion protein comprises, consists, or consists essentially of an amino acid sequence from Table 1, or a variant and/or fragment thereof.

p97 Sequences.

In certain embodiments, a p97 polypeptide sequence used in a composition and/or fusion protein of the invention comprises, consists essentially of, or consists of a human p97 reference sequence provided in Table 2 below. Also included are variants and fragments thereof.

TABLE 2

Exemplary p97 Sequences

| Description | Sequence | SEQ ID NO: |
|---|---|---|
| FL Human p97 | <u>MRGPSGALWLLLALRTV</u>LGGMEVRWCATSDPEQHKCGNMSEAFREAGIQ PSLLCVRGTSADHCVQLIAAQEADAITLDGGAIYEAGKEHGLKPVVGEV YDQEVGTSYYAVAVVRRSSHVTIDTLKGVKSCHTGINRTVGWNVPVGYL VESGRLSVMGCDVLKAVSDYFGGSCVPGAGETSYSESLCRLCRGDSSGE GVCDKSPLERYYDYSGAFRCLAEGAGDVAFVKHSTVLENTDGKTLPSWG QALLSQDFELLCRDGSRADVTEWRQCHLARVPAHAVVVRADTDGGLIFR LLNEGQRLFSHEGSSFQMFSSEAYGQKDLLFKDSTSELVPIATQTYEAW LGHEYLHAMKGLLCDPNRLPPYLRWCVLSTPEIQKCGDMAVAFRRQRLK PEIQCVSAKSPQHCMERIQAEQVDAVTLSGEDIYTAGKTYGLVPAAGEH YAPEDSSNSYYVAVVRRDSSHAFTLDELRGKRSCHAGFGSPAGWDVPV GALIQRGFIRPKDCDVLTAVSEFFNASCVPVNNPKNYPSSLCALCVGDE QGRNKCVGNSQERYYGYRGAFRCLVENAGDVAFVRHTTVFDNTNGHNSE PWAAELRSEDYELLCPNGARAEVSQFAACNLAQIPPHAVMVRPDTNIFT VYGLLDKAQDLFGDDHNKNGFKMFDSSNYHGQDLLFKDATVRAVPVGEK TTYRGWLGLDYVAALEGMSSQQCSG<u>AAAPAPGAPLLPLLLPALAARLLP PAL</u> | 1 |
| Soluble Human p97 | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN GFKMFDSSNYHGQDLLFKDATVRAVPVGEKTTYRGWLGLDYVAALEGMS SQQCS | 2 |
| P97 fragment | WCATSDPEQHK | 3 |
| P97 fragment | RSSHVTIDTLK | 4 |
| P97 fragment | SSHVTIDTLKGVK | 5 |
| P97 fragment | LCRGDSSGEGVCDK | 6 |
| P97 fragment | GDSSGEGVCDKSPLER | 7 |
| P97 fragment | YYDYSGAFR | 8 |
| P97 fragment | ADVTEWR | 9 |
| P97 fragment | VPAHAVVVR | 10 |
| P97 fragment | ADTDGGLIFR | 11 |

TABLE 2-continued

Exemplary p97 Sequences

| Description | Sequence | SEQ ID NO: |
|---|---|---|
| P97 fragment | CGDMAVAFR | 12 |
| P97 fragment | LKPEIQCVSAK | 13 |
| P97 fragment | DSSHAFTLDELR | 14 |
| P97 fragment | DSSHAFTDELRY | 148 |
| P97 fragment | SEDYELLCPNGAR | 15 |
| P97 fragment | AQDLFGDDHNKNGFK | 16 |
| P97 fragment | FSSEAYGQKDLLFKDSTSELVPIATQTYEAWLGHEYLHAM | 17 |
| P97 fragment | ERIQAEQVDAVTLSGEDIYTAGKTYGLVPAAGEHYAPEDSSNSYYVVAV VRRDSSHAFTLDELRGKRSCHAGFGSPAGWDVPVGALIQRGFIRPKDCD VLTAVSEFFNASCVPVNNPKNYPSSLCALCVGDEQGRNKCVGNSQERYY GYRGAFRCLVENAGDVAFVRHTTVFDNTNGHNSEPWAAELRSEDYELLC PNGARAEVSQFAACNLAQIPPHAVM | 18 |
| P97 fragment | VRPDTNIFTVYGLLDKAQDLFGDDHNKNGFKM | 19 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTN | 20 |
| P97 fragment | GHNSEPWAAELRSEDYELLCPN | 21 |
| P97 fragment | GARAEVSQFAACNLAQIPPHAVMVRPDTNIFTVYGLLDKAQDLFGDDHN KN | 22 |
| P97 fragment | GFKMFDSSNYHGQDLLFKDATVRAVPVGEKTTYRGWLGLDYVAALEGMS SQQC | 23 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPN | 24 |
| P97 fragment | GMEVRWCATSDPEQHKCGNMSEAFREAGIQPSLLCVRGTSADHCVQLIA AQEADAITLDGGAIYEAGKEHGLKPVVGEVYDQEVGTSYYAVAVVRRSS HVTIDTLKGVKSCHTGINRTVGWNVPVGYLVESGRLSVMGCDVLKAVSD YFGGSCVPGAGETSYSESLCRLCRGDSSGEGVCDKSPLERYYDYSGAFR CLAEGAGDVAFVKHSTVLENTDGKTLPSWGQALLSQDFELLCRDGSRAD VTEWRQCHLARVPAHAVVVRADTDGGLIFRLLNEGQRLFSHEGSSFQMF SSEAYGQKDLLFKDSTSELVPIATQTYEAWLGHEYLHAMKGLLCDPNRL PPYLRWCVLSTPEIQKCGDMAVAFRRQRLKPEIQCVSAKSPQHCMERIQ AEQVDAVTLSGEDIYTAGKTYGLVPAAGEHYAPEDSSNSYYVVAVVRRD SSHAFTLDELRGKRSCHAGFGSPAGWDVPVGALIQRGFIRPKDCDVLTA VSEFFNASCVPVNNPKNYPSSLCALCVGDEQGRNKCVGNSQERYYGYRG AFRCLVENAGDVAFVRHTTVFDNTNGHNSEPWAAELRSEDYELLCPNGA RAEVSQFAACNLAQIPPHAVMVRPDTNIFTVYGLLDKAQDLFGDDHNKN | 25 |
| P97 fragment | GHNSEPWAAELRSEDYELLCPNGARAEVSQFAACNLAQIPPHAVMVRPD TNIFTVYGLLDKAQDLFGDDHNKN | 26 |

TABLE 2-continued

Exemplary p97 Sequences

| Description | Sequence | SEQ ID NO: |
|---|---|---|
| P97 fragment | GHNSEPWAAELRSEDYELLCPNGARAEVSQFAACNLAQIPPHAVMVRPD TNIFTVYGLLDKAQDLFGDDHNKNGFKMFDSSNYHGQDLLFKDATVRAV PVGEKTTYRGWLGLDYVAALEGMSSQQC | 27 |
| P97 fragment | GARAEVSQFAACNLAQIPPHAVMVRPDTNIFTVYGLLDKAQDLFGDDHN KNGFKMFDSSNYHGQDLLFKDATVRAVPVGEKTTYRGWLGLDYVAALEG MSSQQC | 28 |

In some embodiments, a p97 polypeptide sequence comprises a sequence having at least 70%, 75%, 80%, 85%, 90%, 95%, 96%, 97%, 98%, or 99% identity or homology, along its length, to a human p97 sequence in Table 2, or a fragment thereof.

In specific embodiments, the p97 polypeptide sequence comprises, consists, or consists essentially of SEQ ID NO:2 (soluble MTf) or SEQ ID NO:14 (MTfpep). In some embodiments, the MTfpep has a C-terminal tyrosine (Y) residue, as set forth in SEQ ID NO:148.

In particular embodiments, a p97 polypeptide sequence comprises a fragment of a human p97 sequence in Table 2. In certain embodiments, a p97 polypeptide fragment is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 700, 710, 720, 730 or more amino acids in length, including all integers and ranges in between, and which may comprise all or a portion of the sequence of a p97 reference sequence.

In certain embodiments, a p97 polypeptide fragment is about 5-700, 5-600, 5-500, 5-400, 5-300, 5-200, 5-100, 5-50, 5-40, 5-30, 5-25, 5-20, 5-15, 5-10, 10-700, 10-600, 10-500, 10-400, 10-300, 10-200, 10-100, 10-50, 10-40, 10-30, 10-25, 10-20, 10-15, 20-700, 20-600, 20-500, 20-400, 20-300, 20-200, 20-100, 20-50, 20-40, 20-30, 20-25, 30-700, 30-600, 30-500, 30-400, 30-300, 30-200, 30-100, 30-50, 30-40, 40-700, 40-600, 40-500, 40-400, 40-300, 40-200, 40-100, 40-50, 50-700, 50-600, 50-500, 50-400, 50-300, 50-200, 50-100, 60-700, 60-600, 60-500, 60-400, 60-300, 60-200, 60-100, 60-70, 70-700, 70-600, 70-500, 70-400, 70-300, 70-200, 70-100, 70-80, 80-700, 80-600, 80-500, 80-400, 80-300, 80-200, 80-100, 80-90, 90-700, 90-600, 90-500, 90-400, 90-300, 90-200, 90-100, 100-700, 100-600, 100-500, 100-400, 100-300, 100-250, 100-200, 100-150, 200-700, 200-600, 200-500, 200-400, 200-300, or 200-250 amino acids in length, and comprises all or a portion of a p97 reference sequence.

In certain embodiments, p97 polypeptide sequences of interest include p97 amino acid sequences, subsequences, and/or variants of p97 that are effective for transporting an agent of interest across the blood brain barrier and into the central nervous system (CNS). In particular embodiments, the variant or fragment comprises the N-lobe of human p97 (residues 20-361 of SEQ ID NO:1). In specific aspects, the variant or fragment comprises an intact and functional $Fe^{3+}$-binding site.

In some embodiments, a p97 polypeptide sequence is a soluble form of a p97 polypeptide (see Yang et al., *Prot Exp Purif*. 34:28-48, 2004), or a fragment or variant thereof. In some aspects, the soluble p97 polypeptide has a deletion of the all or a portion of the hydrophobic domain (residues 710-738 of SEQ ID NO:1), alone or in combination with a deletion of all or a portion of the signal peptide (residues 1-19 of SEQ ID NO:1). In specific aspects, the soluble p97 polypeptide comprises or consists of SEQ ID NO:2 (residues 20-710 or 20-711 of SEQ ID NO:1), including variants and fragments thereof.

In certain embodiments, for instance, those that employ liposomes, the p97 polypeptide sequence is a lipid soluble form of a p97 polypeptide. For instance, certain of these and related embodiments include a p97 polypeptide that comprises all or a portion of the hydrophobic domain, optionally with or without the signal peptide.

In certain other embodiments, the p97 fragment or variant is capable of specifically binding to a p97 receptor, an LRP1 receptor and/or an LRP1B receptor.

Variants and fragments of reference p97 polypeptides and other reference polypeptides are described in greater detail below.

Iduronate-2-Sulfatase Sequences.

In certain embodiments, an IDS (or I2S) polypeptide sequence used in a fusion protein of the invention comprises, consists essentially of, or consists of one or more human IDS sequences illustrated in Table 3 below.

TABLE 3

Exemplary IDS Sequences

| Name | Sequence | SEQ ID NO: |
|---|---|---|
| Full-length human IDS (signal sequence | MPPPRTGRGLLWLGLVLSSVCVALGSETQANSTTDALNVLLIIVDDLRP SLGCYGDKLVRSPNIDQLASHSLLFQNAFAQQAVCAPSRVSFLTGRRPD TTRLYDFNSYWRVHAGNFSTIPQYFKENGYVTMSVGKVFHPGISSNHTD DSPYSWSFPPYHPSSEKYENTKTCRGPDGELHANLLCPVDVLDVPEGTL | 31 |

TABLE 3-continued

Exemplary IDS Sequences

| Name | Sequence | SEQ ID NO: |
|---|---|---|
| underlined) | PDKQSTEQAIQLLEKMKTSASPFFLAVGYHKPHIPFRYPKEFQKLYPLE NITLAPDPEVPDGLPPVAYNPWMDIRQREDVQALNISVPYGPIPVDFQR KIRQSYFASVSYLDTQVGRLLSALDDLQLANSTIIAFTSDHGWALGEHG EWAKYSNFDVATHVPLIFYVPGRTASLPEAGEKLFPYLDPFDSASQLME PGRQSMDLVELVSLFPTLAGLAGLQVPPRCPVPSFHVELCREGKNLLKH FRFRDLEEDPYLPGNPRELIAYSQYPRPSDIPQWNSDKPSLKDIKIMGY SIRTIDYRYTVWVGFNPDEFLANFSDIHAGELYFVDSDPLQDHNMYNDS QGGDLFQLLMP | |
| Human IDS with propeptide sequence (underlined) but without signal sequence | SETQANSTTDALNVLLIIVDDLRPSLGCYGDKLVRSPNIDQLASHSLLF QNAFAQQAVCAPSRVSFLTGRRPDTTRLYDFNSYWRVHAGNFSTIPQYF KENGYVTMSVGKVFHPGISSNHTDDSPYSWSFPPYHPSSEKYENTKTCR GPDGELHANLLCPVDVLDVPEGTLPDKQSTEQAIQLLEKMKTSASPFFL AVGYHKPHIPFRYPKEFQKLYPLENITLAPDPEVPDGLPPVAYNPWMDI RQREDVQALNISVPYGPIPVDFQRKIRQSYFASVSYLDTQVGRLLSALD DLQLANSTIIAFTSDHGWALGEHGEWAKYSNFDVATHVPLIFYVPGRTA SLPEAGEKLFPYLDPFDSASQLMEPGRQSMDLVELVSLFPTLAGLAGLQ VPPRCPVPSFHVELCREGKNLLKHFRFRDLEEDPYLPGNPRELIAYSQY PRPSDIPQWNSDKPSLKDIKIMGYSIRTIDYRYTVWVGFNPDEFLANFS DIHAGELYFVDSDPLQDHNMYNDSQGGDLFQLLMP | 32 |
| Human IDS without propeptide or signal sequence | TDALNVLLIIVDDLRPSLGCYGDKLVRSPNIDQLASHSLLFQNAFAQQA VCAPSRVSFLTGRRPDTTRLYDFNSYWRVHAGNFSTIPQYFKENGYVTM SVGKVFHPGISSNHTDDSPYSWSFPPYHPSSEKYENTKTCRGPDGELHA NLLCPVDVLDVPEGTLPDKQSTEQAIQLLEKMKTSASPFFLAVGYHKPH IPFRYPKEFQKLYPLENITLAPDPEVPDGLPPVAYNPWMDIRQREDVQA LNISVPYGPIPVDFQRKIRQSYFASVSYLDTQVGRLLSALDDLQLANST IIAFTSDHGWALGEHGEWAKYSNFDVATHVPLIFYVPGRTASLPEAGEK LFPYLDPFDSASQLMEPGRQSMDLVELVSLFPTLAGLAGLQVPPRCPVP SFHVELCREGKNLLKHFRFRDLEEDPYLPGNPRELIAYSQYPRPSDIPQ WNSDKPSLKDIKIMGYSIRTIDYRYTVWVGFNPDEFLANFSDIHAGELY FVDSDPLQDHNMYNDSQGGDLFQLLMP | 33 |
| Human IDS 42 kDa chain | TDALNVLLIIVDDLRPSLGCYGDKLVRSPNIDQLASHSLLFQNAFAQQA VCAPSRVSFLTGRRPDTTRLYDFNSYWRVHAGNFSTIPQYFKENGYVTM SVGKVFHPGISSNHTDDSPYSWSFPPYHPSSEKYENTKTCRGPDGELHA NLLCPVDVLDVPEGTLPDKQSTEQAIQLLEKMKTSASPFFLAVGYHKPH IPFRYPKEFQKLYPLENITLAPDPEVPDGLPPVAYNPWMDIRQREDVQA LNISVPYGPIPVDFQRKIRQSYFASVSYLDTQVGRLLSALDDLQLANST IIAFTSDHGWALGEHGEWAKYSNFDVATHVPLIFYVPGRTASLPEAGEK LFPYLDPFDSASQLMEPGRQSMDLVELVSLFPTLAGLAGLQVPPRCPVP SFHVELCREGKNLLKHFRFRDLEEDPYLPG | 34 |
| Human IDS 14 kDa chain | NPRELIAYSQYPRPSDIPQWNSDKPSLKDIKIMGYSIRTIDYRYTVWVG FNPDEFLANFSDIHAGELYFVDSDPLQDHNMYNDSQGGDLFQLLMP | 35 |

Also included are biologically active variants and fragments of the IDS sequences in Table 3 and the Sequence Listing. In certain aspects, a biologically active IDS polypeptide or variants/fragment thereof hydrolyzes the 2-sulfate groups of the L-iduronate 2-sulfate units of dermatan sulfate, heparan sulfate, and/or heparin, for example, at about 30%, 35%, 40%, 45%, 50%, 55%, 60%, 65%, 70%, 75%, 80%, 85%, 90%, 95%, 100%, 200%, 300%, 400%, 500% or more of the activity of wild-type human IDS (e.g., SEQ ID NO:31).

Linkers.

As noted above, certain fusion proteins may employ one or more linker groups, including peptide linkers. Such linkers can be rigid linkers, flexible linkers, stable linkers, or releasable linkers, such as enzymatically-cleavable linkers. See, e.g., Chen et al., Adv. Drug. Deliv. Ref., 65:1357-69, 2012.

For instance, for polypeptide-polypeptide conjugates, peptide linkers can separate the components by a distance sufficient to ensure that each polypeptide folds into its secondary and tertiary structures. Such a peptide linker sequence may be incorporated into the fusion protein using standard techniques described herein and well-known in the art. Suitable peptide linker sequences may be chosen based on the following factors: (1) their ability to adopt a rigid or flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180.

In certain illustrative embodiments, a peptide linker is between about 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide linker comprises about 1, 5, 10, 15, 20, 25, 30, 35, 40, 45, 50 or more amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA*. 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

In particular embodiments, the linker is a rigid linker. Examples of rigid linkers include, without limitation, $(EAAAK)_x$ (SEQ ID NO:36) and $A(EAAAK)_xALEA$ $(EAAAK)_xA$ (SEQ ID NO:41), and $(Ala-Pro)_x$ where $x$ is 1, 2, 3, 4, 5, 6, 7, 8, 9, 10, 11, 12, 13, 14, 15, 16, 17, 18, 19, or 20 or more. Specific examples of rigid linkers include EAAAK (SEQ ID NO:36), $(EAAAK)_2$ (SEQ ID NO:37), $(EAAAK)_3$ (SEQ ID NO:38), $A(EAAAK)_4ALEA(EAAAK)_4A$ (SEQ ID NO:42), PAPAP (SEQ ID NO:43), and AEAAAKEAAAKA (SEQ ID NO:44).

In specific embodiments, the linker comprises, consists, or consists essentially of $(EAAAK; SEQ ID NO: 36)_3$ or EAAAKEAAAKEAAAK (SEQ ID NO:38)

In some embodiments, the linker is a flexible linker. In particular embodiments, the flexible linker is GGGGS (SEQ ID NO:45), $(GGGGS)_2$ (SEQ ID NO:46), $(GGGGS)_3$ (SEQ ID NO:47), or $Gly_{2-10}$ (SEQ ID NOS:48-54). Additional examples of flexible linkers are provided below.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO:55), $[GGSG]_x$ (SEQ ID NO:56), $[GGGS]_x$ (SEQ ID NO: 57), $[GGGGS]_x$ (SEQ ID NO: 45), $[GN]_x$, $[GGN]_x$, $[GNN]_x$, $[GNGN]_x$ (SEQ ID NO: 58), $[GNNG]_x$ (SEQ ID NO: 59), $[GGGN]_x$ (SEQ ID NO: 60), $[GGGGN]_x$ (SEQ ID NO: 61) linkers, where $x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art. In specific embodiments, the linker comprises or consists of a $[GGGGS]_3$ (SEQ ID NO: 47) sequence, or GGGGSGGGGSGGGGS (SEQ ID NO: 47).

In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS*. 90:2256-2260, 1993; and *PNAS*. 91:11099-11103, 1994) or by phage display methods.

The peptide linkers may be physiologically stable or may include a releasable linker such as a physiologically degradable or enzymatically degradable linker (e.g., proteolytically or enzymatically-cleavable linker). In certain embodiments, one or more releasable linkers can result in a shorter half-life and more rapid clearance of the fusion protein. These and related embodiments can be used, for example, to enhance the solubility and blood circulation lifetime of p97 fusion proteins in the bloodstream, while also delivering an agent into the bloodstream (or across the BBB) that, subsequent to linker degradation, is substantially free of the p97 sequence. These aspects are especially useful in those cases where polypeptides or other agents, when permanently fused to a p97 sequence, demonstrate reduced activity. By using the linkers as provided herein, such polypeptides can maintain their therapeutic activity when in conjugated or fused form. In these and other ways, the properties of the p97 fusion proteins can be more effectively tailored to balance the bioactivity and circulating half-life of the polypeptides over time.

Specific examples of enzymatically-cleavable linkers include, without limitation, a Factor XIa/FVIIa cleavable linker (VSQTSKLTR ▼ AETVFPDV) (SEQ ID NO:62), a matrix metalloprotease-1 cleavable linker (PLG ▼ LWA) (SEQ ID NO:63), an HIV protease cleavable linker (RVL ▼ AEA) (SEQ ID NO:64), a hepatitis C virus NS3 protease cleavable linker (EDVVCC ▼ SMSY) (SEQ ID NO:65), a Factor Xa cleavable linker (GGIEGR/GS) (SEQ ID NO:66), a Furin cleavable linker (TRHRQPRY ▼ GWE or AGNRVRR ▼ SVG or RRRRRRR ▼ R ▼ R) (SEQ ID NOS:67-69), and a Cathepsin B cleavable linker (GFLG) (SEQ ID NO:70).

Enzymatically degradable linkages suitable for use in particular embodiments include, but are not limited to: an amino acid sequence cleaved by a serine protease such as thrombin, chymotrypsin, trypsin, elastase, kallikrein, or subtilisin. Illustrative examples of thrombin-cleavable amino acid sequences include, but are not limited to: -Gly-Arg-Gly-Asp—(SEQ ID NO: 71), -Gly-Gly-Arg-, -Gly-Arg-Gly-Asp-Asn-Pro—(SEQ ID NO:72), -Gly-Arg-Gly-Asp-Ser—(SEQ ID NO: 73), -Gly-Arg-Gly-Asp-Ser-Pro-Lys—(SEQ ID NO: 74), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val—(SEQ ID NO:75), -Ala-Ala-Pro-Leu—(SEQ ID NO: 76), -Ala-Ala-Pro-Phe—(SEQ ID NO: 77), -Ala-Ala-Pro-Ala—(SEQ ID NO: 78), and -Ala-Tyr-Leu-Val—(SEQ ID NO: 79).

Enzymatically degradable linkages suitable for use in particular embodiments also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z—(SEQ ID NO: 80), -Gly-Pro-, Leu-Gly-Pro-Z—(SEQ ID NO: 81), -Gly-Pro-Ile-Gly-Pro-Z—(SEQ ID NO:82), and -Ala-Pro-Gly-Leu-Z—(SEQ ID NO: 83), where Y and Z are amino acids. Illustrative examples of collagenase-cleavable amino acid sequences include, but are not limited to: -Pro-Leu-Gly-Pro-D-Arg-Z—(SEQ ID NO: 84), -Pro-Leu-Gly-Leu-Leu-Gly-Z—(SEQ ID NO: 85), -Pro-Gln-Gly-Ile-Ala-Gly-Trp—(SEQ ID NO: 86), -Pro-Leu-Gly-Cys(Me)-His—(SEQ ID NO: 87), -Pro-Leu-Gly-Leu-Tyr-Ala—(SEQ ID NO:88), -Pro-Leu-Ala-Leu-Trp-Ala-Arg—(SEQ ID NO: 89), and -Pro-Leu-Ala-Tyr-Trp-Ala-Arg—(SEQ ID NO: 90), where Z is an amino acid. An illustrative example of a stromelysin-cleavable amino acid sequence is -Pro-Tyr-Ala-Tyr-Tyr-Met-Arg—(SEQ ID NO: 91); and an example of a gelatinase-cleavable amino acid sequence is -Pro-Leu-Gly-Met-Tyr-Ser-Arg—(SEQ ID NO: 92).

Enzymatically degradable linkages suitable for use in particular embodiments also include amino acid sequences that can be cleaved by an angiotensin converting enzyme, such as, for example, -Asp-Lys-Pro-, -Gly-Asp-Lys-Pro—(SEQ ID NO: 93), and -Gly-Ser-Asp-Lys-Pro—(SEQ ID NO: 94).

Enzymatically degradable linkages suitable for use in particular embodiments also include amino acid sequences that can be degraded by cathepsin B, such as, for example, -Val-Cit-, -Ala-Leu-Ala-Leu—(SEQ ID NO:95), -Gly-Phe-Leu-Gly—(SEQ ID NO:96) and -Phe-Lys-.

In certain embodiments, however, any one or more of the non-peptide or peptide linkers are optional. For instance, linker sequences may not be required in a fusion protein where the first and second polypeptides have non-essential N-terminal and/or C-terminal amino acid regions that can be used to separate the functional domains and prevent steric interference.

Signal Peptide Sequences.

In certain embodiments, a p97 fusion protein comprises one or more signal peptide sequences (SP). In particular embodiments, the signal peptide sequence is an N-terminal signal sequence, i.e., the most N-terminal portion of the fusion protein.

Specific examples of signal sequences are provided in Table 4 below. See also Kober et al., Biotechnology and Bioengineering. 110:1164-73, 2013.

Thus, in some embodiments, the signal peptide comprises, consists, or consists essentially of at least one sequence from Table 4. In some embodiments, the signal peptide comprises SEQ ID NO:149.

In specific embodiments, the signal peptide sequence corresponds to the most N-terminal protein (p97 or IDS) of the fusion protein. That is, in some embodiments the N-terminal signal peptide sequence is the human p97 signal peptide sequence (SEQ ID NO:39) and the p97 fusion protein comprises the general structure: p97 SP-p97-IDS. In other embodiments, the N-terminal signal sequence is the human IDS signal peptide sequence (SEQ ID NO:40) and the p97 fusion protein comprises the general structure: IDS SP-IDS-p97. Optionally, the fusion protein can further comprise one or more purification tags and/or protease sites, for example, between the N-terminal signal sequence and the p97/IDS portions of the fusion protein, as described elsewhere herein. Here, the protease site is typically place at the C-terminus of the signal sequence or purification tag so that treatment with the corresponding protease removes the N-terminal signal sequence, purification tag, and most or the entire protease site from the fusion protein.

TABLE 4

Exemplary Signal Peptide Sequences (SP)

| Protein | Signal Sequence | SEQ ID NO: |
|---|---|---|
| Human p97 | MRGPSGALWLLLALRTVLG | 39 |
| Human IDS | MPPPRTGRGLLWLGLVLSSVCVALG | 40 |
| Ig Heavy Chain | MEWSWVFLFFLSVTTGVHS | 149 |
| Ig kappa light chain precursor | MDMRAPAGIFGFLLVLFPGYRS | 97 |
| Serum albumin preprotein | MKWVTFISLLFLFSSAYS | 98 |
| Ig heavy chain | MDWTWRVFCLLAVTPGAHP | 99 |
| Ig light chain | MAWSPLFLTLITHCAGSWA | 100 |
| Azurocidin preprotein | MTRLTVLALLAGLLASSRA | 101 |
| Cystatin-S precursor | MARPLCTLLLLMATLAGALA | 102 |
| Trypsinogen 2 precursor | MRSLVFVLLIGAAFA | 103 |
| Potassium channel blocker | MSRLFVFILIALFLSAIIDVMS | 104 |
| Alpha conotoxin | MGMRMMFIMFMLVVLATTVVS | 105 |
| Alfa-galactosidase (mutant m3) | MRAFLFLTACISLPGVFG | 106 |
| Cellulase | MKFQSTLLLAAAAGSALA | 107 |
| Aspartic proteinase nepenthesin-1 | MASSLYSFLLALSIVYIFVAPTHS | 108 |
| Acid chitinase | MKTHYSSAILPILTLFVFLSINPSHG | 109 |
| K28 prepro-toxin | MESVSSLFNIFSTIMVNYKSLVLALLSVSNLKYARG | 110 |
| Killer toxin zygocin precursor | MKAAQILTASIVSLLPIYTSA | 111 |
| Cholera toxin | MIKLKFGVFFTVLLSSAYA | 112 |

Purification Tags.

In some embodiments, the fusion protein comprises one or more purification or affinity tags (TAG or TAGs). Non-limiting examples of purification tags include poly-histidine tags (e.g., 6×His tags), avidin, FLAG tags, glutathione S-transferase (GST) tags, maltose-binding protein tags, chitin binding protein (CBP), and others. Also included are epitope tags, which bind to high-affinity antibodies, examples of which include V5-tags, Myc-tags, and HA-tags. In specific examples, the purification tag is a polyhistidine tag ($H_{5-10}$), for example, $H_5$, $H_6$, $H_7$, $H_8$, $H_9$, or $H_{10}$ (SEQ ID NOS:113-118).

Non-limiting examples of purification tags are provided in Table 5 below.

TABLE 5

Exemplary Purification Tags (TAG)

| Name | Sequence | SEQ ID NO: |
|---|---|---|
| 5X-HIS | HHHHH | 113 |
| 6X-HIS | HHHHHH | 114 |
| 7X-HIS | HHHHHHH | 115 |
| 8X-HIS | HHHHHHHH | 116 |
| 9X-HIS | HHHHHHHHH | 117 |
| 10X-HIS | HHHHHHHHHH | 118 |
| AviTag | GLNDIFEAQKIEWHE | 119 |
| Calmodulin-tag | KRRWKKNFIAVSAANRFKKISSSGAL | 120 |
| Polyglutamate tag | EEEEEE | 121 |
| FLAG-tag | DYKDDDDK | 122 |
| HA-tag | YPYDVPDYA | 123 |
| MYC-tag | EQKLISEEDL | 124 |
| S-tag | KETAAAKFERQHMDS | 125 |
| SPB-tag | MDEKTTGWRGGHVVEGLAGELEQLRARLEHHPQGQREP | 126 |
| Softag 1 | SLAELLNAGLGGS | 127 |
| Softag 3 | TQDPSRVG | 128 |
| V5 tag | GKPIPNPLLGLDST | 129 |
| Xpress tag | DLYDDDDK | 130 |

Thus, in certain embodiments, the purification tag comprises, consists, or consists essentially of at least one sequence from Table 5. In specific embodiments, the tag comprises a FLAG tag and a HIS tag, for example, a 10×-HIS tag.

Protease Sites (PS).

In some embodiments, the fusion protein comprises one or more protease sites. Optionally, the one or more protease sites are positioned at the C-terminus of the purification tag and/or signal peptide sequence (if either one or both are present) so that treatment with the corresponding protease removes the N-terminal signal sequence, purification tag, and/or most or all of the protease site from the fusion protein.

In particular embodiments, for instance, where the fusion protein comprises an enzymatically-cleavable linker, the protease site typically differs from that of the enzymatically-cleavable linker, so that treatment with the protease removes any terminal sequences (e.g., signal peptide sequence, purification tag) without cleaving the peptide linker between the p97 and IDS sequences.

Non-limiting examples of protease sites are provided in Table 6 below.

TABLE 6

Exemplary Protease Sites (PS)

| Protease | Sequence | SEQ ID NO: |
|---|---|---|
| Thrombin | LVPR▼GS | 131 |
| Enteropeptidase | DDDDK▼ | 132 |
| Factor Xa | I(E/D)GR▼ | 133 |
| Enterokinase | DDDDK▼ | 134 |
| TEV Protease | ENLYFQ▼G | 135 |
| HRV 3C Protease | LEVLFQ▼GP | 136 |
| SUMO Protease (Ulp1) | GSLQDSEVNQEAKPEVKPEVKPETHINLKVSDGSSEIFFKIKKTTPLRRLMEAFAKRQGKEMDSLTFLYDGIEIQADQTPEDLDMEDNDIIEAHREQIGG | 137 |

▼ Denotes site of cleavage

Thus, in certain embodiments, the protease site comprises, consists, or consists essentially of at least one sequence from Table 6. In specific embodiments, the protease site comprises the TEV protease site (SEQ ID NO:135).

Variant Sequences.

Certain embodiments include variants of the reference polypeptide and polynucleotide sequences described herein, whether described by name or by reference to a sequence identifier, including p97 sequences, IDS sequences, linker sequences, signal peptide sequences, purification tags, and protease sites (see, e.g., Tables 1-6 and the Sequence Listing). The wild-type or most prevalent sequences of these polypeptides are known in the art, and can be used as a comparison for the variants and fragments described herein.

A "variant" sequence, as the term is used herein, refers to a polypeptide or polynucleotide sequence that differs from a reference sequence disclosed herein by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In other specific embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In still other specific embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Polynucleotides, Host Cells, and Methods of Production.

Certain embodiments relate to polynucleotides that encode the fusion proteins described herein, and vectors that comprise such polynucleotides, for example, where the polynucleotides are operably linked to one or more regulatory elements. Also included are recombinant host cells that comprise such polynucleotides, vectors, fusion proteins, and methods of recombinant production of the foregoing.

Fusion proteins may be prepared using standard techniques. Preferably, however, a fusion protein is expressed as a recombinant protein in an expression system, as described herein and known in the art. Fusion proteins can contain one or multiple copies of a p97 sequence and one or multiple copies of an IDS sequence, present in any desired arrangement.

Polynucleotides and fusion polynucleotides can contain one or multiple copies of a nucleic acid encoding a p97 polypeptide sequence, and/or may contain one or multiple copies of a nucleic acid encoding an IDS sequence.

For fusion proteins, DNA sequences encoding the p97 polypeptide sequence, the IDS sequence of interest, and optionally a peptide linker components may be assembled separately, and then ligated into an appropriate expression vector. The 3' end of the DNA sequence encoding one polypeptide component can be ligated, with or without a peptide linker, to the 5' end of a DNA sequence encoding the other polypeptide component(s) so that the reading frames of the sequences are in frame. The ligated DNA sequences are operably linked to suitable transcriptional and/or translational regulatory elements. The regulatory elements responsible for expression of DNA are usually located only 5' to the DNA sequence encoding the first polypeptides. Similarly, stop codons required to end translation and transcription termination signals are only present 3' to the DNA sequence encoding the most C-terminal polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion proteins.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008).

Exemplary polynucleotide sequences are provided in Table 7 below.

TABLE 7

Exemplary polynucleotide sequences

| Name | Polynucleotide Sequence | SEQ ID NO: |
|---|---|---|
| I2S-MTf | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCTCGGAAACTCAGGCCAACTCCACCACAGATGCACTCAACGTG<br>CTGCTGATCATCGTAGATGACCTCCGACCTTCTCTGGGCTGTTACGGCGACAAG<br>CTAGTACGGAGCCCAAACATCGACCAGCTCGCATCGCACTCTCTCCTATTCCAG<br>AACGCATTCGCCCAGCAGGCTGTCTGTGCTCCCTCCCGAGTGTCCTTCCTCACG<br>GGTCGGAGACCCGATACCACGAGGTTATATGACTTCAACTCATACTGGCGCGTG<br>CATGCCGGTAACTTTTCTACTATACCCCAGTATTTTAAAGAAAATGGCTATGTT<br>ACAATGTCCGTTGGCAAGGTATTTCATCCTGGTATTAGCAGCAACCACACAGAT<br>GACTCTCCGTATAGCTGGTCATTCCCACCATACCACCCCTCCAGCGAAAAGTAC<br>GAAAACACAAAGACTTGCCGGGGCCCAGATGGCGAACTGCACGCAAATCTGCTG<br>TGCCCTGTAGATGTCTTGGACGTGCCCGAAGGTACTCTGCCCGACAAACAGTCC<br>ACAGAACAGGCAATCCAACTCCTTGAAAAGATGAAAACGAGCGCGTCCCCCTTC<br>TTCCTCGCCGTGGGCTACCACAAGCCCCACATCCCGTTTAGATACCCCAAGGAA<br>TTTCAGAAACTGTACCCCCTGGAAAACATCACTCTCGCGCCCGACCCCGAAGTG<br>CCAGACGGACTCCCTCCTGTTGCCTACAACCCTTGGATGGACATCAGACAACGT<br>GAAGATGTGCAGGCCCTGAACATCTCAGTGCCTTACGGCCCCATTCCAGTTGAC<br>TTCCAGAGGAAGATTCGGCAGTCCTACTTCGCCTCCGTTAGTTACCTGGACACC<br>CAAGTGGGTAGACTCCTGAGCGCCTTGGACGATCTCCAGCTCGCAAACAGCACC<br>ATCATTGCCTTCACCAGCGACCATGGTTGGGCGCTGGGTGAACATGGAGAATGG<br>GCTAAATATTCAAATTTCGACGTTGCGACCCACGTCCCATTGATCTTCTACGTG<br>CCTGGACGAACAGCCTCCTTGCCTGAAGCCGGGGAAAAGTTGTTTCCATATCTG<br>GACCCTTTCGATTCTGCGAGCCAACTCATGGAACCTGGGCGACAGAGCATGGAC<br>CTGGTGGAACTGGTCAGTTTATTTCCAACCCTGGCAGGCCTTGCAGGCCTCCAA<br>GTTCCACCTCGGTGTCCCGTTCCCTCATTCCACGTCGAACTCTGTCGCGAAGGT<br>AAAAACCTCCTCAAGCATTTTCGTTTTCGGGACCTCGAAGAAGACCCATACCTG<br>CCAGGGAATCCAAGGGAACTGATTGCCTACAGCCAGTACCCTAGACCTAGCGAC<br>ATCCCACAGTGGAACAGCGACAAGCCCTCCCTCAAGGACATTAAAATCATGGGT<br>TATAGTATCCGGACTATTGACTACAGGTATACCGTGTGGGTGGGTTTCAACCCA<br>GACGAATTTCTCGCCAATTTCTCCGACATCCACGCGGGCGAACTGTATTTCGTT<br>GATTCCGATCCACTGCAAGATCATAATATGTACAACGATAGTCAAGGGGGTGAC<br>CTCTTCCAGTTGCTAATGCCAGAAGCCGCCGCGAAAGAAGCCGCCGCAAAAGAA<br>GCCGCTGCCAAAGGCATGGAAGTGCGTTGGTGCGCCACCTCTGACCCCGAGCAG<br>CACAAGTGCGGCAACATGTCCGAGGCCTTCAGAGAGGCCGGCATCCAGCCTTCT<br>CTGCTGTGTGTGCGGGGCACCTCTGCCGACCATTGCGTGCAGCTGATCGCCGCC<br>CAGGAAGCCGACGCTATCACACTGGATGGCGGCGCTATCTACGAGGCTGGCAAA | 143 |

TABLE 7-continued

Exemplary polynucleotide sequences

| Name | Polynucleotide Sequence | SEQ ID NO: |
|---|---|---|
| | GAGCACGGCCTGAAGCCCGTCGTGGGCGAGGTGTACGATCAGGAAGTGGGCACC<br>TCCTACTACGCCGTGGCTGTCGTGCGGAGATCCTCCCACGTGACCATCGACACC<br>CTGAAGGGCGTGAAGTCCTGCCACACCGGCATCAACAGAACCGTGGGCTGGAAC<br>GTGCCCGTGGGCTACCTGGTGGAATCCGGCAGACTGTCCGTGATGGGCTGCGAC<br>GTGCTGAAGGCCGTGTCCGATTACTTCGGCGGCTCTTGTGTGCCTGGCGCTGGC<br>GAGACATCCTACTCCGAGTCCCTGTGCAGACTGTGCAGGGGCGACTCTTCTGGC<br>GAGGGCGTGTGCGACAAGTCCCCTCTGGAACGGTACTACGACTACTCCGGCGCC<br>TTCAGATGCCTGGCTGAAGGTGCTGGCGACGTGGCCTTCGTGAAGCACTCCACC<br>GTGCTGGAAAACACCGACGGCAAGACCCTGCCTTCTTGGGGCCAGGCACTGCTG<br>TCCCAGGACTTCGAGCTGCTGTGCCGGGATGGCTCCAGAGCCGATGTGACAGAG<br>TGGCGGCAGTGCCACCTGGCCAGAGTGCCTGCTCATGCTGTGGTCGTGCGCGCC<br>GATACAGATGGCGGCCTGATCTTCCGGCTGCTGAACGAGGGCCAGCGGCTGTTC<br>TCTCACGAGGGCTCCAGCTTCCAGATGTTCTCCAGCGAGGCCTACGGCCAGAAG<br>GACCTGCTGTTCAAGGACTCCACCTCCGAGCTGGTGCCTATCGCCACCCAGACC<br>TATGAGGCTTGGCTGGGCCACGAGTACCTGCACGCTATGAAGGGACTGCTGTGC<br>GACCCCAACCGGCTGCCTCCTTATCTGAGGTGGTGCGTGCTGTCCACCCCCGAG<br>ATCCAGAAATGCGGCGATATGGCCGTGGCCTTTCGGCGGCAGAGACTGAAGCCT<br>GAGATCCAGTGCGTGTCCGCCAAGAGCCCTCAGCACTGCATGGAACGGATCCAG<br>GCCGAACAGGTGGACGCCGTGACACTGTCCGGCGAGGATATCTACACCGCCGGA<br>AAGACCTACGGCCTGGTGCCAGCTGCTGGCGAGCATTACGCCCCTGAGGACTCC<br>TCCAACAGCTACTACGTGGTGGCAGTCGTGCGCCGGGACTCCTCTCACGCCTTT<br>ACCCTGGATGAGCTGCGGGCAAGAGAAGCTGTCACGCCGGCTTTGGAAGCCCT<br>GCCGGATGGGATGTGCCTGTGGGCGCTCTGATCCAGCGGGGCTTCATCAGACCC<br>AAGGACTGTGATGTGCTGACCGCCGTGTCTGAGTTCTTCAACGCCTCCTGTGTG<br>CCCGTGAACAACCCCAAGAACTACCCCTCCAGCCTGTGCGCCCTGTGTGTGGGA<br>GATGAGCAGGGCCGGAACAAATGCGTGGGCAACTCCCAGGAAAGATATTACGGC<br>TACAGAGGCGCCTTCCGGTGTCTGGTGGAAAACGCCGGGGATGTGGCTTTTGTG<br>CGGCACACCACCGTGTTCGACAACACCAATGGCCACAACTCCGAGCCTTGGGCC<br>GCTGAGCTGAGATCCGAGGATTACGAACTGCTGTGTCCCAACGGCGCCAGGGCT<br>GAGGTGTCCCAGTTTGCCGCCTGTAACCTGGCCCAGATCCCTCCCCACGCTGTG<br>ATGGTGCGACCCGACACCAACATCTTCACCGTGTACGGCCTGCTGGACAAGGCC<br>CAGGATCTGTTCGGCGACGACCACAACAAGAACGGGTTCAAGATGTTCGACTCC<br>AGCAACTACCACGGACAGGATCTGCTGTTTAAAGATGCCACCGTGCGGGCCGTG<br>CCAGTGGGCGAAAAGACCACCTACAGAGGATGGCTGGGACTGGACTACGTGGCC<br>GCCCTGGAAGGCATGTCCTCCCAGCAGTGTTCCTGA | |
| MTf-I2S | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCGGCATGGAAGTGCGTTGGTGCGCCACCTCTGACCCCGAGCAG<br>CACAAGTGCGGCAACATGTCCGAGGCCTTCAGAGAGGCCGGCATCCAGCCTTCT<br>CTGCTGTGTGTGCGGGCACCTCTGCCGACCATTGCGTGCAGCTGATCGCCGCC<br>CAGGAAGCCGACGCTATCACACTGGATGGCGGCGCTATCTACGAGGCTGGCAAA<br>GAGCACGGCCTGAAGCCCGTCGTGGGCGAGGTGTACGATCAGGAAGTGGGCACC<br>TCCTACTACGCCGTGGCTGTCGTGCGGAGATCCTCCCACGTGACCATCGACACC<br>CTGAAGGGCGTGAAGTCCTGCCACACCGGCATCAACAGAACCGTGGGCTGGAAC<br>GTGCCCGTGGGCTACCTGGTGGAATCCGGCAGACTGTCCGTGATGGGCTGCGAC<br>GTGCTGAAGGCCGTGTCCGATTACTTCGGCGGCTCTTGTGTGCCTGGCGCTGGC<br>GAGACATCCTACTCCGAGTCCCTGTGCAGACTGTGCAGGGGCGACTCTTCTGGC<br>GAGGGCGTGTGCGACAAGTCCCCTCTGGAACGGTACTACGACTACTCCGGCGCC<br>TTCAGATGCCTGGCTGAAGGTGCTGGCGACGTGGCCTTCGTGAAGCACTCCACC<br>GTGCTGGAAAACACCGACGGCAAGACCCTGCCTTCTTGGGGCCAGGCACTGCTG<br>TCCCAGGACTTCGAGCTGCTGTGCCGGGATGGCTCCAGAGCCGATGTGACAGAG<br>TGGCGGCAGTGCCACCTGGCCAGAGTGCCTGCTCATGCTGTGGTCGTGCGCGCC<br>GATACAGATGGCGGCCTGATCTTCCGGCTGCTGAACGAGGGCCAGCGGCTGTTC<br>TCTCACGAGGGCTCCAGCTTCCAGATGTTCTCCAGCGAGGCCTACGGCCAGAAG<br>GACCTGCTGTTCAAGGACTCCACCTCCGAGCTGGTGCCTATCGCCACCCAGACC<br>TATGAGGCTTGGCTGGGCCACGAGTACCTGCACGCTATGAAGGGACTGCTGTGC<br>GACCCCAACCGGCTGCCTCCTTATCTGAGGTGGTGCGTGCTGTCCACCCCCGAG<br>ATCCAGAAATGCGGCGATATGGCCGTGGCCTTTCGGCGGCAGAGACTGAAGCCT<br>GAGATCCAGTGCGTGTCCGCCAAGAGCCCTCAGCACTGCATGGAACGGATCCAG<br>GCCGAACAGGTGGACGCCGTGACACTGTCCGGCGAGGATATCTACACCGCCGGA<br>AAGACCTACGGCCTGGTGCCAGCTGCTGGCGAGCATTACGCCCCTGAGGACTCC<br>TCCAACAGCTACTACGTGGTGGCAGTCGTGCGCCGGGACTCCTCTCACGCCTTT<br>ACCCTGGATGAGCTGCGGGCAAGAGAAGCTGTCACGCCGGCTTTGGAAGCCCT<br>GCCGGATGGGATGTGCCTGTGGGCGCTCTGATCCAGCGGGGCTTCATCAGACCC<br>AAGGACTGTGATGTGCTGACCGCCGTGTCTGAGTTCTTCAACGCCTCCTGTGTG<br>CCCGTGAACAACCCCAAGAACTACCCCTCCAGCCTGTGCGCCCTGTGTGTGGGA<br>GATGAGCAGGGCCGGAACAAATGCGTGGGCAACTCCCAGGAAAGATATTACGGC<br>TACAGAGGCGCCTTCCGGTGTCTGGTGGAAAACGCCGGGGATGTGGCTTTTGTG<br>CGGCACACCACCGTGTTCGACAACACCAATGGCCACAACTCCGAGCCTTGGGCC<br>GCTGAGCTGAGATCCGAGGATTACGAACTGCTGTGTCCCAACGGCGCCAGGGCT<br>GAGGTGTCCCAGTTTGCCGCCTGTAACCTGGCCCAGATCCCTCCCCACGCTGTG<br>ATGGTGCGACCCGACACCAACATCTTCACCGTGTACGGCCTGCTGGACAAGGCC<br>CAGGATCTGTTCGGCGACGACCACAACAAGAACGGGTTCAAGATGTTCGACTCC | 144 |

TABLE 7-continued

Exemplary polynucleotide sequences

| Name | Polynucleotide Sequence | SEQ ID NO: |
|---|---|---|
| | AGCAACTACCACGGACAGGATCTGCTGTTTAAAGATGCCACCGTGCGGGCCGTG<br>CCAGTGGGCGAAAAGACCACCTACAGAGGATGGCTGGGACTGGACTACGTGGCC<br>GCCCTGGAAGGCATGTCCTCCCAGCAGTGTTCCGAAGCCGCCGCGAAAGAAGCC<br>GCCGCAAAAGAAGCCGCTGCCAAATCGGAAACTCAGGCCAACTCCACCACAGAT<br>GCACTCAACGTGCTGCTGATCATCGTAGATGACCTCCGACCTTCTCTGGGCTGT<br>TACGGCGACAAGCTAGTACGGAGCCCAAACATCGACCAGCTCGCATCGCACTCT<br>CTCCTATTCCAGAACGCATTCGCCCAGCAGGCTGTCTGTGCTCCCTCCCGAGTG<br>TCCTTCCTCACGGGTCGGAGACCCGATACCACGAGGTTATATGACTTCAACTCA<br>TACTGGCGCGTGCATGCCGGTAACTTTTCTACTATACCCCAGTATTTTAAAGAA<br>AATGGCTATGTTACAATGTCCGTTGGCAAGGTATTTCATCCTGGTATTAGCAGC<br>AACCACACAGATGACTCTCCGTATAGCTGGTCATTCCCACCATACCACCCCTCC<br>AGCGAAAAGTACGAAAACACAAAGACTTGCCGGGGCCCAGATGGCGAACTGCAC<br>GCAAATCTGCTGTGCCCTGTAGATGTCTTGGACGTGCCCGAAGGTACTCTGCCC<br>GACAAACAGTCCACAGAACAGGCAATCCAACTCCTTGAAAAGATGAAAACGAGC<br>GCGTCCCCCTTCTTCCTCGCCGTGGGCTACCACAAGCCCCACATCCCGTTTAGA<br>TACCCCAAGGAATTTCAGAAACTGTACCCCCTGGAAAACATCACTCTCGCGCCC<br>GACCCCGAAGTGCCAGACGGACTCCCTCCTGTTGCCTACAACCCTTGGATGGAC<br>ATCAGACAACGTGAAGATGTGCAGGCCCTGAACATCCAGTGCCTTACGGCCCC<br>ATTCCAGTTGACTTCCAGAGGAAGATTCGGCAGTCCTACTTCGCCTCCGTTAGT<br>TACCTGGACACCCAAGTGGGTAGACTCCTGAGCGCCTTGGACGATCTCCAGCTC<br>GCAAACAGCACCATCATTGCCTTCACCAGCGACCATGGTTGGGCGCTGGGTGAA<br>CATGGAGAATGGGCTAAATATTCAAATTTCGACGTTGCGACCCACGTCCCATTG<br>ATCTTCTACGTGCCTGGACGAACAGCCTCCTTGCCTGAAGCCGGGGAAAAGTTG<br>TTTCCATATCTGGACCCTTTCGATTCTGCGAGCCAACTCATGGAACCTGGGCGA<br>CAGAGCATGGACCTGGTGGAACTGGTCAGTTTATTTCCAACCCTGGCAGGCCTT<br>GCAGGCCTCCAAGTTCCACCTCGGTGTCCCGTTCCCTCATTCCACGTCGAACTC<br>TGTCGCGAAGGTAAAAACCTCCTCAAGCATTTTCGTTTTCGGGACCTCGAAGAA<br>GACCCATACCTGCCAGGGAATCCAAGGGAACTGATTGCCTACAGCCAGTACCCT<br>AGACCTAGCGACATCCCACAGTGGAACAGCGACAAGCCCTCCCTCAAGGACATT<br>AAAATCATGGGTTATAGTATCCGGACTATTGACTACAGGTATACCGTGTGGGTG<br>GGTTTCAACCCAGACGAATTTCTCGCCAATTTCTCCGACATCCACGCGGGCGAA<br>CTGTATTTCGTTGATTCCGATCCACTGCAAGATCATAATATGTACAACGATAGT<br>CAAGGGGGTGACCTCTTCCAGTTGCTAATGCCATGA | |
| MTfpep-<br>I2S | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCGACTCCTCTCACGCCTTCACCCTGGACGAGCTGCGGTACGAA<br>GCCGCCGCGAAAGAAGCCGCCGCAAAAGAAGCCGCTGCCAAATCGGAAACTCAG<br>GCCAACTCCACCACAGATGCACTCAACGTGCTGCTGATCATCGTAGATGACCTC<br>CGACCTTCTCTGGGCTGTTACGGCGACAAGCTAGTACGGAGCCCAAACATCGAC<br>CAGCTCGCATCGCACTCTCTCCTATTCCAGAACGCATTCGCCCAGCAGGCTGTC<br>TGTGCTCCCTCCCGAGTGTCCTTCCTCACGGGTCGGAGACCCGATACCACGAGG<br>TTATATGACTTCAACTCATACTGGCGCGTGCATGCCGGTAACTTTTCTACTATA<br>CCCCAGTATTTTAAAGAAAATGGCTATGTTACAATGTCCGTTGGCAAGGTATTT<br>CATCCTGGTATTAGCAGCAACCACACAGATGACTCTCCGTATAGCTGGTCATTC<br>CCACCATACCACCCCTCCAGCGAAAAGTACGAAAACACAAAGACTTGCCGGGGC<br>CCAGATGGCGAACTGCACGCAAATCTGCTGTGCCCTGTAGATGTCTTGGACGTG<br>CCCGAAGGTACTCTGCCCGACAAACAGTCCACAGAACAGGCAATCCAACTCCTT<br>GAAAAGATGAAAACGAGCGCGTCCCCCTTCTTCCTCGCCGTGGGCTACCACAAG<br>CCCCACATCCCGTTTAGATACCCCAAGGAATTTCAGAAACTGTACCCCCTGGAA<br>AACATCACTCTCGCGCCCGACCCCGAAGTGCCAGACGGACTCCCTCCTGTTGCC<br>TACAACCCTTGGATGGACATCAGACAACGTGAAGATGTGCAGGCCCTGAACATC<br>TCAGTGCCTTACGGCCCCATTCCAGTTGACTTCCAGAGGAAGATTCGGCAGTCC<br>TACTTCGCCTCCGTTAGTTACCTGGACACCCAAGTGGGTAGACTCCTGAGCGCC<br>TTGGACGATCTCCAGCTCGCAAACAGCACCATCATTGCCTTCACCAGCGACCAT<br>GGTTGGGCGCTGGGTGAACATGGAGAATGGGCTAAATATTCAAATTTCGACGTT<br>GCGACCCACGTCCCATTGATCTTCTACGTGCCTGGACGAACAGCCTCCTTGCCT<br>GAAGCCGGGGAAAAGTTGTTTCCATATCTGGACCCTTTCGATTCTGCGAGCCAA<br>CTCATGGAACCTGGGCGACAGAGCATGGACCTGGTGGAACTGGTCAGTTTATTT<br>CCAACCCTGGCAGGCCTTGCAGGCCTCCAAGTTCCACCTCGGTGTCCCGTTCCC<br>TCATTCCACGTCGAACTCTGTCGCGAAGGTAAAAACCTCCTCAAGCATTTTCGT<br>TTTCGGGACCTCGAAGAAGACCCATACCTGCCAGGGAATCCAAGGGAACTGATT<br>GCCTACAGCCAGTACCCTAGACCTAGCGACATCCCACAGTGGAACAGCGACAAG<br>CCCTCCCTCAAGGACATTAAAATCATGGGTTATAGTATCCGGACTATTGACTAC<br>AGGTATACCGTGTGGGTGGGTTTCAACCCAGACGAATTTCTCGCCAATTTCTCC<br>GACATCCACGCGGGCGAACTGTATTTCGTTGATTCCGATCCACTGCAAGATCAT<br>AATATGTACAACGATAGTCAAGGGGGTGACCTCTTCCAGTTGCTAATGCCATGA | 145 |
| I2S-<br>MTfpep | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCTCGGAAACTCAGGCCAACTCCACCACAGATGCACTCAACGTG<br>CTGCTGATCATCGTAGATGACCTCCGACCTTCTCTGGGCTGTTACGGCGACAAG<br>CTAGTACGGAGCCCAAACATCGACCAGCTCGCATCGCACTCTCTCCTATTCCAG | 146 |

TABLE 7-continued

Exemplary polynucleotide sequences

| Name | Polynucleotide Sequence | SEQ ID NO: |
|---|---|---|
| | AACGCATTCGCCCAGCAGGCTGTCTGTGCTCCCTCCCGAGTGTCCTTCCTCACG<br>GGTCGGAGACCCGATACCACGAGGTTATATGACTTCAACTCATACTGGCGCGTG<br>CATGCCGGTAACTTTTCTACTATACCCCAGTATTTTAAAGAAAATGGCTATGTT<br>ACAATGTCCGTTGGCAAGGTATTTCATCCTGGTATTAGCAGCAACCACACAGAT<br>GACTCTCCGTATAGCTGGTCATTCCCACCATACCACCCCTCCAGCGAAAAGTAC<br>GAAAACACAAAGACTTGCCGGGGCCCAGATGGCGAACTGCACGCAAATCTGCTG<br>TGCCCTGTAGATGTCTTGGACGTGCCCGAAGGTACTCTGCCCGACAAACAGTCC<br>ACAGAACAGGCAATCCAACTCCTTGAAAAGATGAAAACGAGCGCGTCCCCCTTC<br>TTCCTCGCCGTGGGCTACCACAAGCCCCACATCCCGTTTAGATACCCCAAGGAA<br>TTTCAGAAACTGTACCCCCTGGAAAACATCACTCTCGCGCCCGACCCCGAAGTG<br>CCAGACGGACTCCCTCCTGTTGCCTACAACCCTTGGATGGACATCAGACAACGT<br>GAAGATGTGCAGGCCCTGAACATCTCAGTGCCTTACGGCCCCATTCCAGTTGAC<br>TTCCAGAGGAAGATTCGGCAGTCCTACTTCGCCTCCGTTAGTTACCTGGACACC<br>CAAGTGGGTAGACTCCTGAGCGCCTTGGACGATCTCCAGCTCGCAAACAGCACC<br>ATCATTGCCTTCACCAGCGACCATGGTTGGGCGCTGGGTGAACATGGAGAATGG<br>GCTAAATATTCAAATTTCGACGTTGCGACCCACGTCCCATTGATCTTCTACGTG<br>CCTGGACGAACAGCCTCCTTGCCTGAAGCCGGGGAAAAGTTGTTTCCATATCTG<br>GACCCTTTCGATTCTGCGAGCCAACTCATGGAACCTGGGCGACAGAGCATGGAC<br>CTGGTGGAACTGGTCAGTTTATTTCCAACCCTGGCAGGCCTTGCAGGCCTCCAA<br>GTTCCACCTCGGTGTCCCGTTCCCTCATTCCACGTCGAACTCTGTCGCGAAGGT<br>AAAAACCTCCTCAAGCATTTTCGTTTTCGGGACCTCGAAGAAGACCCATACCTG<br>CCAGGGAATCCAAGGGAACTGATTGCCTACAGCCAGTACCCTAGACCTAGCGAC<br>ATCCCACAGTGGAACAGCGACAAGCCCTCCCTCAAGGACATTAAAATCATGGGT<br>TATAGTATCCGGACTATTGACTACAGGTATACCGTGTGGGTGGGTTTCAACCCA<br>GACGAATTTCTCGCCAATTTCTCCGACATCCACGCGGGCGAACTGTATTTCGTT<br>GATTCCGATCCACTGCAAGATCATAATATGTACAACGATAGTCAAGGGGTGAC<br>CTCTTCCAGTTGCTAATGCCAGAGGCCGCTGCTAAAGAGGCTGCCGCCAAAGAA<br>GCCGCCGCTAAGGACTCCTCTCACGCCTTCACCCTGGACGAGCTGCGGTACTAA | |
| I2S-<br>MTfpep<br>(without<br>propep of<br>I2S) | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCACAGATGCACTCAACGTGCTGCTGATCATCGTAGATGACCTC<br>CGACCTTCTCTGGGCTGTTACGGCGACAAGCTAGTACGGAGCCCAAACATCGAC<br>CAGCTCGCATCGCACTCTCTCCTATTCCAGAACGCATTCGCCCAGCAGGCTGTC<br>TGTGCTCCCTCCCGAGTGTCCTTCCTCACGGGTCGGAGACCCGATACCACGAGG<br>TTATATGACTTCAACTCATACTGGCGCGTGCATGCCGGTAACTTTTCTACTATA<br>CCCCAGTATTTTAAAGAAAATGGCTATGTTACAATGTCCGTTGGCAAGGTATTT<br>CATCCTGGTATTAGCAGCAACCACACAGATGACTCTCCGTATAGCTGGTCATTC<br>CCACCATACCACCCCTCCAGCGAAAAGTACGAAAACACAAAGACTTGCCGGGGC<br>CCAGATGGCGAACTGCACGCAAATCTGCTGTGCCCTGTAGATGTCTTGGACGTG<br>CCCGAAGGTACTCTGCCCGACAAACAGTCCACAGAACAGGCAATCCAACTCCTT<br>GAAAAGATGAAAACGAGCGCGTCCCCCTTCTTCCTCGCCGTGGGCTACCACAAG<br>CCCCACATCCCGTTTAGATACCCCAAGGAATTTCAGAAACTGTACCCCCTGGAA<br>AACATCACTCTCGCGCCCGACCCCGAAGTGCCAGACGGACTCCCTCCTGTTGCC<br>TACAACCCTTGGATGGACATCAGACAACGTGAAGATGTGCAGGCCCTGAACATC<br>TCAGTGCCTTACGGCCCCATTCCAGTTGACTTCCAGAGGAAGATTCGGCAGTCC<br>TACTTCGCCTCCGTTAGTTACCTGGACACCCAAGTGGGTAGACTCCTGAGCGCC<br>TTGGACGATCTCCAGCTCGCAAACAGCACCATCATTGCCTTCACCAGCGACCAT<br>GGTTGGGCGCTGGGTGAACATGGAGAATGGGCTAAATATTCAAATTTCGACGTT<br>GCGACCCACGTCCCATTGATCTTCTACGTGCCTGGACGAACAGCCTCCTTGCCT<br>GAAGCCGGGGAAAAGTTGTTTCCATATCTGGACCCTTTCGATTCTGCGAGCCAA<br>CTCATGGAACCTGGGCGACAGAGCATGGACCTGGTGGAACTGGTCAGTTTATTT<br>CCAACCCTGGCAGGCCTTGCAGGCCTCCAAGTTCCACCTCGGTGTCCCGTTCCC<br>TCATTCCACGTCGAACTCTGTCGCGAAGGTAAAAACCTCCTCAAGCATTTTCGT<br>TTTCGGGACCTCGAAGAAGACCCATACCTGCCAGGGAATCCAAGGGAACTGATT<br>GCCTACAGCCAGTACCCTAGACCTAGCGACATCCCACAGTGGAACAGCGACAAG<br>CCCTCCCTCAAGGACATTAAAATCATGGGTTATAGTATCCGGACTATTGACTAC<br>AGGTATACCGTGTGGGTGGGTTTCAACCCAGACGAATTTCTCGCCAATTTCTCC<br>GACATCCACGCGGGCGAACTGTATTTCGTTGATTCCGATCCACTGCAAGATCAT<br>AATATGTACAACGATAGTCAAGGGGTGACCTCTTCCAGTTGCTAATGCCAGAG<br>GCCGCTGCTAAAGAGGCTGCCGCCAAAGAAGCCGCCGCTAAGGACTCCTCTCAC<br>GCCTTCACCCTGGACGAGCTGCGGTACTAA | 147 |

Thus, in certain embodiments, a polynucleotide that encodes a fusion protein or antibody fusion described herein, or a portion thereof, comprises one or more polynucleotide sequences from Table 7 (e.g., SEQ ID NOS:143-147), or a fragment/variant thereof.

In some embodiments, a nucleic acids or vectors encoding a subject p97 polypeptide, an IDS polypeptide, and/or a p97-IDS fusion are introduced directly into a host cell, and the cell is incubated under conditions sufficient to induce expression of the encoded polypeptide(s). Therefore, according to certain related embodiments, there is provided a recombinant host cell which comprises a polynucleotide or a fusion polynucleotide that encodes one or more fusion proteins described herein, and which optionally comprises additional exogenous polynucleotides.

Expression of a fusion protein in the host cell may be achieved by culturing the recombinant host cells (containing the polynucleotide(s)) under appropriate conditions. Following production by expression, the polypeptide(s) and/or fusion proteins, may be isolated and/or purified using any suitable technique, and then used as desired. The term "host cell" is used to refer to a cell into which has been introduced, or which is capable of having introduced into it, a nucleic acid sequence encoding one or more of the polypeptides described herein, and which further expresses or is capable of expressing a selected gene of interest, such as a gene encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of aminoacyl tRNA synthetase(s) that can incorporate unnatural amino acids into the polypeptide.

Systems for cloning and expression of a protein in a variety of different host cells are well known. Suitable host cells include mammalian cells, bacteria, yeast, and baculovirus systems. Mammalian cell lines available in the art for expression of a heterologous polypeptide include Chinese hamster ovary (CHO) cells, HeLa cells, baby hamster kidney cells, HEK-293 cells, human fibrosarcoma cell line HT-1080 (see, e.g., Moran, Nat. Biotechnol. 28:1139-40, 2010), NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for polypeptide production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

A common, preferred bacterial host is *E. coli*. The expression of proteins in prokaryotic cells such as *E. coli* is well established in the art. For a review, see for example Pluckthun, *A. Bio/Technology.* 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in Ion and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His•Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the fusion protein of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., fusion proteins. Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the fusion proteins have a purity of at least about 90%, as measured according to routine techniques in the art. In certain embodiments, such as diagnostic compositions or certain therapeutic compositions, the fusion proteins have a purity of at least about 95%. In specific embodiments, such as therapeutic or pharmaceutical compositions, the fusion proteins have a purity of at least about 97% or 98% or 99%. In other embodiments, such as when being used as reference or research reagents, fusion proteins can be of lesser purity, and may have a purity of at least about 50%, 60%, 70%, or 80%. Purity can be measured overall or in relation to selected components, such as other proteins, e.g., purity on a protein basis.

In certain embodiments, as noted above, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the fusion proteins are made from a eukaryotic cell such as a mammalian or human cell in substantially serum free media.

Methods of Use and Pharmaceutical Compositions

Certain embodiments of the present invention relate to methods of using the p97 fusion proteins described herein. Examples of such methods include methods of treatment and methods of diagnosis, including for instance, the use of p97 fusion proteins for medical imaging of certain organs/tissues, such as those of the nervous system. Some embodiments include methods of diagnosing and/or treating disorders or conditions of the central nervous system (CNS), or disorders or conditions having a CNS component. Particular aspects include methods of treating a lysosomal storage disorder (LSD), including those having a CNS component.

Accordingly, certain embodiments include methods of treating a subject in need thereof, comprising administering a p97 fusion protein described herein. Also included are methods of delivering an IDS enzyme to the nervous system (e.g., central nervous system tissues) of a subject, comprising administering a composition that comprises a p97 fusion protein described herein. In certain of these and related embodiments, the methods increase the rate of delivery of the agent to the central nervous system tissues, relative, for example, to delivery by a composition that comprises a non-fusion IDS enzyme.

In some instances, the subject has or is at risk for having a lysosomal storage disease. Certain methods thus relate to the treatment of lysosomal storage diseases in a subject in need thereof, optionally those lysosomal storage diseases associated with the central nervous system, or having CNS involvement. Exemplary lysosomal storage diseases include mucopolysaccharidosis type II (Hunter Syndrome). Hunter Syndrome is an X-linked multisystem disorder characterized by glycosaminoglycans (GAG) accumulation. The vast majority of affected individuals are male; on rare occasion carrier females manifest findings. Age of onset, disease severity, and rate of progression may vary significantly.

In those with severe disease, CNS involvement (manifest primarily by progressive cognitive deterioration), progressive airway disease, and cardiac disease usually result in death in the first or second decade of life. Certain embodiments therefore include the treatment of Hunter Syndrome with CNS involvement.

In those with attenuated disease, the CNS is not (or is minimally) affected, although the effect of GAG accumulation on other organ systems may be just as severe as in those who have progressive cognitive decline. Survival into the early adult years with normal intelligence is common in the attenuated form of the disease. However, subjects with attenuated disease can still benefit from administration of a p97-IDS fusion protein having improved penetration into CNS tissues, for instance, to reduce the risk of progression from attenuated Hunter Syndrome to that with CNS involvement.

Additional findings in both forms of Hunter Syndrome include: short stature; macrocephaly with or without communicating hydrocephalus; macroglossia; hoarse voice; conductive and sensorineural hearing loss; hepatomegaly and/or splenomegaly; dysostosis multiplex and joint contractures including ankylosis of the temporomandibular joint; spinal stenosis; and carpal tunnel syndrome. Subjects undergoing treatment with fusion proteins described herein may thus have one or more of these findings of Hunter Syndrome.

Urine GAGs and skeletal surveys can establish the presence of an MPS condition but are not specific to MPS II. The gold standard for diagnosis of MPS II in a male proband is deficient iduronate sulfatase (IDS) enzyme activity in white cells, fibroblasts or plasma in the presence of normal activity of at least one other sulfatase. Molecular genetic testing of IDS, the only gene in which mutation is known to be associated with Hunter Syndrome, can be used to confirm the diagnosis in a male proband with an unusual phenotype or a phenotype that does not match the results of GAG testing.

Common treatments for Hunter Syndrome include developmental, occupational, and physical therapy; shunting for hydrocephalus; tonsillectomy and adenoidectomy; positive pressure ventilation (CPAP or tracheostomy); carpal tunnel release; cardiac valve replacement; inguinal hernia repair.

Hence, in certain aspects, a subject for treatment by the fusion proteins described herein may be about to undergo, is undergoing, or has undergone one or more of these treatments.

Disease monitoring can depend on organ system involvement and disease severity, and usually includes annual cardiac evaluation and echocardiograms; pulmonary evaluations including pulmonary function testing; audiograms; eye examinations; developmental assessments; and neurologic examinations. Additional studies may include sleep studies for obstructive apnea; nerve conduction velocity (NCV) to assess for carpal tunnel syndrome; evaluations for hydrocephalus; orthopedic evaluations to monitor hip disease. Thus, in some aspects, a subject for treatment by the fusion proteins described herein may be about to undergo, is undergoing, or has undergone one or more of these disease monitoring protocols.

For in vivo use, for instance, for the treatment of human disease, medical imaging, or testing, the p97 fusion proteins described herein are generally incorporated into a pharmaceutical composition prior to administration. A pharmaceutical composition comprises one or more of the p97 fusion proteins described herein in combination with a physiologically acceptable carrier or excipient.

To prepare a pharmaceutical composition, an effective or desired amount of one or more fusion proteins is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of fusion proteins described herein, in pure form or in an appropriate pharmaceutical composition, can be carried out via any of the accepted modes of administration of agents for serving similar utilities. The pharmaceutical compositions can be prepared by combining a fusion protein-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented. Particular embodiments include administration by IV infusion. Some embodiments include administration by intraperitoneal (IP) injection. Also included are combinations thereof.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In certain aspects, a fusion protein is bound to or encapsulated within a particle, e.g., a nanoparticle, bead, lipid formulation, lipid particle, or liposome, e.g., immunoliposome. The fusion proteins may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will typically contain a therapeutically effective amount of a fusion protein described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a fusion protein such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the conjugate or agent and thereby assists in the delivery of the compound. Suitable agents that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the fusion proteins against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the conjugate so as to facilitate dissolution or homogeneous suspension of the conjugate in the aqueous delivery system.

The compositions may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

Compositions described herein may also be administered simultaneously with, prior to, or after administration of one or more other therapeutic agents, as described herein. For instance, in one embodiment, the conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Such combination therapy may include administration of a single pharmaceutical dosage formulation, which contains a compound of the invention (i.e., fusion protein) and one or more additional active agents, as well as administration of compositions comprising conjugates of the invention and each active agent in its own separate pharmaceutical dosage formulation. For example, a fusion protein as described herein and the other active agent can be administered to the patient together in a single oral dosage composition such as a tablet or capsule, or each agent administered in separate oral dosage formulations. Similarly, a fusion protein as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising fusion proteins and one or more additional active agents can be administered at essentially the same time, i.e., concurrently, or at separately staggered times, i.e., sequentially and in any order; combination therapy is understood to include all these regimens.

The various embodiments described herein can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

In Vitro Activity of Fusion Proteins

Fusion proteins of human p97 (melanotransferrin; MTf) and human duronate-2-sulfatase (IDS) were prepared and tested for enzymatic activity in vitro. Table E1 provides the amino acid sequences and Table E2 provides the corresponding polynucleotide coding sequences of the fusion proteins that were prepared and tested.

TABLE E1

Polypeptide Sequences of Fusion Proteins

| Name | Sequence | SEQ ID NO: |
|---|---|---|
| I2S-MTf (SP; TAG: PS; I2S; Linker; Soluble MTf) | MEWSWVFLFFLSVTTGVHSDYKDDDDKEQKLISEEDLHHHHHHHHHGGGGENL YFQGSETQANSTTDALNVLLIIVDDLRPSLGCYGDKLVRSPNIDQLASHSLLFQ NAFAQQAVCAPSRVSFLTGRRPDTTRLYDFNSYWRVHAGNFSTIPQYFKENGYV TMSVGKVFHPGISSNHTDDSPYSWSFPPYHPSSEKYENTKTCRGPDGELHANLL CPVDVLDVPEGTLPDKQSTEQAIQLLEKMKTSASPFFLAVGYHKPHIPFRYPKE FQKLYPLENITLAPDPEVPDGLPPVAYNPWMDIRQREDVQALNISVPYGPIPVD FQRKIRQSYFASVSYLDTQVGRLLSALDDLQLANSTIIAFTSDHGWALGEHGEW AKYSNFDVATHVPLIFYVPGRTASLPEAGEKLFPYLDPFDSASQLMEPGRQSMD LVELVSLFPTLAGLAGLQVPPRCPVPSFHVELCREGKNLLKHFRFRDLEEDPYL PGNPRELIAYSQYPRPSDIPQWNSDKPSLKDIKIMGYSIRTIDYRYTVWVGFNP DEFLANFSDIHAGELYFVDSDPLQDHNMYNDSQGGDLFQLLMPEAAAKEAAAKE AAAKGMEVRWCATSDPEQHKCGNMSEAFREAGIQPSLLCVRGTSADHCVQLIAA QEADAITLDGGAIYEAGKEHGLKPVVGEVYDQEVGTSYYAVAVVRRSSHVTIDT LKGVKSCHTGINRTVGWNVPVGYLVESGRLSVMGCDVLKAVSDYFGGSCVPGAG ETSYSESLCRLCRGDSSGEGVCDKSPLERYYDYSGAFRCLAEGAGDVAFVKHST VLENTDGKTLPSWGQALLSQDFELLCRDGSRADVTEWRQCHLARVPAHAVVRA DTDGGLIFRLLNEGQRLFSHEGSSFQMFSSEAYGQKDLLFKDSTSELVPIATQT YEAWLGHEYLHAMKGLLCDPNRLPPYLRWCVLSTPEIQKCGDMAVAFRRQRLKP EIQCVSAKSPQHCMERIQAEQVDAVTLSGEDIYTAGKTYGLVPAAGEHYAPEDS SNSYYVVAVVRRDSSHAFTLDELRGKRSCHAGFGSPAGWDVPVGALIQRGFIRP KDCDVLTAVSEFFNASCVPVNNPKNYPSSLCALCVGDEQGRNKCVGNSQERYYG | 138 |

TABLE E1-continued

Polypeptide Sequences of Fusion Proteins

| Name | Sequence | SEQ ID NO: |
|---|---|---|
| | YRGAFRCLVENAGDVAFVRHTTVFDNTNGHNSEPWAAELRSEDYELLCPNGARA<br>EVSQFAACNLAQIPPHAVMVRPDTNIFTVYGLLDKAQDLFGDDHNKNGFKMFDS<br>SNYHGQDLLFKDATVRAVPVGEKTTYRGWLGLDYVAALEGMSSQQCS | |
| MTf-I2S<br>(SP: TAG:<br>PS:<br>Soluble<br>MTf:<br>Linker:<br>I2S) | MEWSWVELFELSVTTGVHSDYKDDDDKEQKLISEEDLHHHHHHHHHHGGGGENL<br>YFQGGMEVRWCATSDPEQHKCGNMSEAFREAGIQPSLLCVGTSADHCVQLIAA<br>QEADAITLDGGAIYEAGKEHGLKPVVGEVYDQEVGTSYYAVAVVRRSSHVTIDT<br>LKGVKSCHTGINRTVGWNPVGYLVESGRLSVMGCDVLKAVSDYFGGSCVPGAG<br>ETSYSESLCRLCRGDSSGEGVCDKSPLERYYDYSGAFRCLAEGAGDVAFVKHST<br>VLENTDGKTLPSWGQALLSQDFELLCRDGSRADVTEWRQCHLARVPAHAVVVRA<br>DTDGGLIFRLLNEGQRLFSHEGSSFQMFSSEAYGQKDLLFKDSTSELVPIATQT<br>YEAWLGHEYLHAMKGLLCDPNRLPPYLRWCVLSTPEIQKCGDMAVAFRRQRLKP<br>EIQCVSAKSPQHCMERIQAEQVDAVTLSGEDIYTAGKTYGLVPAAGEHYAPEDS<br>SNSYYVAVVRRDSSHAFTLDELRGKRSCHAGFGSPAGWDVPVGALIQRGFIRP<br>KDCDVLTAVSEFFNASCVPVNNPKNYPSSLCALCVGDEQGRNKCVGNSQERYYG<br>YRGAFRCLVENAGDVAFVRHTTVFDNTNGHNSEPWAAELRSEDYELLCPNGARA<br>EVSQFAACNLAQIPPHAVMVRPDTNIFTVYGLLDKAQDLFGDDHNKNGFKMFDS<br>SNYHGQDLLFKDATVRAVPVGEKTTYRGWLGLDYVAALEGMSSQQCSEAAAKEA<br>AAKEAAAKSETQANSTTDALNVLLIIVDDLRPSLGCYGDKLVRSPNIDQLASHS<br>LLFQNAFAQQAVCAPSRVSFLTGRRPDTTRLYDFNSYWRVHAGNFSTIPQYFKE<br>NGYVTMSVGKVFHPGISSNHTDDSPYSWSFPPYHPSSEKYENTKTCRGPDGELH<br>ANLLCPVDVLDVPEGTLPDKQSTEQAIQLLEKMKTSASPFFLAVGYHKPHIPFR<br>YPKEFQKLYPLENITLAPDPEVPDGLPPVAYNPWMDIRQREDVQALNISVPYGP<br>IPVDFQRKIRQSYFASVSYLDTQVGRLLSALDDLQLANSTIIAFTSDHGWALGE<br>HGEWAKYSNFDVATHVPLIFYVPGRTASLPEAGEKLFPYLDPFDSASQLMEPGR<br>QSMDLVELVSLFPTLAGLAGLQVPPRCPVPSFHVELCREGKNLLKHFRFRDLEE<br>DPYLPGNPRELIAYSQYPRPSDIPQWNSDKPSLKDIKIMGYSIRTIDYRYTVWV<br>GFNPDEFLANFSDIHAGELYFVDSDPLQDHNMYNDSQGGDLFQLLMP | 139 |
| MTfpep-<br>I2S<br>(SP: TAG:<br>PS:<br>MTfpep:<br>Linker:<br>I2S) | MEWSWVFLFFLSVTTGVHSDYKDDDDKEQKLISEEDLHHHHHHHHHHGGGGENL<br>YFQGDSSHAFTLDELRYEAAAKEAAAKEAAAKSETQANSTTDALNVLLIIVDDL<br>RPSLGCYGDKLVRSPNIDQLASHSLLFQNAFAQQAVCAPSRVSFLTGRRPDTTR<br>LYDFNSYWRVHAGNFSTIPQYFKENGYVTMSVGKVFHPGISSNHTDDSPYSWSF<br>PPYHPSSEKYENTKTCRGPDGELHANLLCPVDVLDVPEGTLPDKQSTEQAIQLL<br>EKMKTSASPFFLAVGYHKPHIPFRYPKEFQKLYPLENITLAPDPEVPDGLPPVA<br>YNPWMDIRQREDVQALNISVPYGPIPVDFQRKIRQSYFASVSYLDTQVGRLLSA<br>LDDLQLANSTIIAFTSDHGWALGEHGEWAKYSNFDVATHVPLIFYVPGRTASLP<br>EAGEKLFPYLDPFDSASQLMEPGRQSMDLVELVSLFPTLAGLAGLQVPPRCPVP<br>SFHVELCREGKNLLKHFRFRDLEEDPYLPGNPRELIAYSQYPRPSDIPQWNSDK<br>PSLKDIKIMGYSIRTIDYRYTVWVGFNPDEFLANFSDIHAGELYFVDSDPLQDH<br>NMYNDSQGGDLFQLLMP | 140 |
| I2S-<br>MTfpep<br>(SP: TAG:<br>PS:<br>I2S:<br>Linker:<br>MTfpep) | MEWSWVFLFFLSVTTGVHSDYKDDDDKEQKLISEEDLHHHHHHHHHHGGGGENL<br>YFQGSETQANSTTDALNVLLIIVDDLRPSLGCYGDKLVRSPNIDQLASHSLLFQ<br>NAFAQQAVCAPSRVSFLTGRRPDTTRLYDFNSYWRVHAGNFSTIPQYFKENGYV<br>TMSVGKVFHPGISSNHTDDSPYSWSFPPYHPSSEKYENTKTCRGPDGELHANLL<br>CPVDVLDVPEGTLPDKQSTEQAIQLLEKMKTSASPFFLAVGYHKPHIPFRYPKE<br>FQKLYPLENITLAPDPEVPDGLPPVAYNPWMDIRQREDVQALNISVPYGPIPVD<br>FQRKIRQSYFASVSYLDTQVGRLLSALDDLQLANSTIIAFTSDHGWALGEHGEW<br>AKYSNFDVATHVPLIFYVPGRTASLPEAGEKLFPYLDPFDSASQLMEPGRQSMD<br>LVELVSLFPTLAGLAGLQVPPRCPVPSFHVELCREGKNLLKHFRFRDLEEDPYL<br>PGNPRELIAYSQYPRPSDIPQWNSDKPSLKDIKIMGYSIRTIDYRYTVWVGFNP<br>DEFLANFSDIHAGELYFVDSDPLQDHNMYNDSQGGDLFQLLMPEAAAKEAAAKE<br>AAAKDSSHAFTLDELRY | 141 |
| I2S-<br>MTfpep<br>(without<br>propep of<br>I2S<br>SP: TAG:<br>PS:<br>I2S w/o<br>propep:<br>Linker:<br>MTfpep) | MEWSWVFLFFLSVTTGVHSDYKDDDDKEQKLISEEDLHHHHHHHHHHGGGGENL<br>YFQGTDALNVLLIIVDDLRPSLGCYGDKLVRSPNIDQLASHSLLFQNAFAQQAV<br>CAPSRVSFLTGRRPDTTRLYDFNSYWRVHAGNFSTIPQYFKENGYVTMSVGKVF<br>HPGISSNHTDDSPYSWSFPPYHPSSEKYENTKTCRGPDGELHANLLCPVDVLDV<br>PEGTLPDKQSTEQAIQLLEKMKTSASPFFLAVGYHKPHIPFRYPKEFQKLYPLE<br>NITLAPDPEVPDGLPPVAYNPWMDIRQREDVQALNISVPYGPIPVDFQRKIRQS<br>YFASVSYLDTQVGRLLSALDDLQLANSTIIAFTSDHGWALGEHGEWAKYSNFDV<br>ATHVPLIFYVPGRTASLPEAGEKLFPYLDPFDSASQLMEPGRQSMDLVELVSLF<br>PTLAGLAGLQVPPRCPVPSFHVELCREGKNLLKHFRFRDLEEDPYLPGNPRELI<br>AYSQYPRPSDIPQWNSDKPSLKDIKIMGYSIRTIDYRYTVWVGFNPDEFLANFS<br>DIHAGELYFVDSDPLQDHNMYNDSQGGDLFQLLMPEAAAKEAAAKEAAAKDSSH<br>AFTLDELRY | 142 |

TABLE E2

Polynucleotide Coding Sequences of Fusion Constructs

| Name | Polynucleotide Sequence | SEQ ID NO: |
|---|---|---|
| I2S-MTf | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCTCGGAAACTCAGGCCAACTCCACCACAGATGCACTCAACGTG<br>CTGCTGATCATCGTAGATGACCTCCGACCTTCTCTGGGCTGTTACGGCGACAAG<br>CTAGTACGGAGCCCAAACATCGACCAGCTCGCATCGCACTCTCTCCTATTCCAG<br>AACGCATTCGCCCAGCAGGCTGTCTGTGCTCCCTCCCGAGTGTCCTTCCTCACG<br>GGTCGGAGACCCGATACCACGAGGTTATATGACTTCAACTCATACTGGCGCGTG<br>CATGCCGGTAACTTTTCTACTATACCCCAGTATTTTAAAGAAAATGGCTATGTT<br>ACAATGTCCGTTGGCAAGGTATTTCATCCTGGTATTAGCAGCAACCACACAGAT<br>GACTCTCCGTATAGCTGGTCATTCCCACCATACCACCCCTCCAGCGAAAAGTAC<br>GAAAACACAAAGACTTGCCGGGGCCCAGATGGCGAACTGCACGCAAATCTGCTG<br>TGCCCTGTAGATGTCTTGGACGTGCCCGAAGGTACTCTGCCCGACAAACAGTCC<br>ACAGAACAGGCAATCCAACTCCTTGAAAAGATGAAAACGAGCGCGTCCCCCTTC<br>TTCCTCGCCGTGGGCTACCACAAGCCCCACATCCCGTTTAGATACCCCAAGGAA<br>TTTCAGAAACTGTACCCCCTGGAAAACATCACTCTCGCGCCCGACCCCGAAGTG<br>CCAGACGGACTCCCTCCTGTTGCCTACAACCCTTGGATGGACATCAGACAACGT<br>GAAGATGTGCAGGCCCTGAACATCTCAGTGCCTTACGGCCCCATTCCAGTTGAC<br>TTCCAGAGGAAGATTCGGCAGTCCTACTTCGCCTCCGTTAGTTACCTGGACACC<br>CAAGTGGGTAGACTCCTGAGCGCCTTGGACGATCTCCAGCTCGCAAACAGCACC<br>ATCATTGCCTTCACCAGCGACCATGGTTGGGCGCTGGGTGAACATGGAGAATGG<br>GCTAAATATTCAAATTTCGACGTTGCGACCCACGTCCCATTGATCTTCTACGTG<br>CCTGGACGAACAGCCTCCTTGCCTGAAGCCGGGGAAAAGTTGTTTCCATATCTG<br>GACCCTTTCGATTCTGCGAGCCAACTCATGGAACCTGGGCGACAGAGCATGGAC<br>CTGGTGGAACTGGTCAGTTTATTTCCAACCCTGGCAGGCCTTGCAGGCCTCCAA<br>GTTCCACCTCGGTGTCCCGTTCCCTCATTCCACGTCGAACTCTGTCGCGAAGGT<br>AAAAACCTCCTCAAGCATTTTCGTTTTCGGGACCTCGAAGAAGACCCATACCTG<br>CCAGGGAATCCAAGGGAACTGATTGCCTACAGCCAGTACCCTAGACCTAGCGAC<br>ATCCCACAGTGGAACAGCGACAAGCCCTCCCTCAAGGACATTAAAATCATGGGT<br>TATAGTATCCGGACTATTGACTACAGGTATACCGTGTGGGTGGGTTTCAACCCA<br>GACGAATTTCTCGCCAATTTCTCCGACATCCACGCGGGCGAACTGTATTTCGTT<br>GATTCCGATCCACTGCAAGATCATAATATGTACAACGATAGTCAAGGGGGTGAC<br>CTCTTCCAGTTGCTAATGCCAGAAGCCGCCGCGAAAGAAGCCGCCGCAAAAGAA<br>GCCGCTGCCAAAGGCATGGAAGTGCGTTGGTGCGCCACCTCTGACCCCGAGCAG<br>CACAAGTGCGGCAACATGTCCGAGGCCTTCAGAGAGGCCGGCATCCAGCCTTCT<br>CTGCTGTGTGTGCGGGGCACCTCTGCCGACCATTGCGTGCAGCTGATCGCCGCC<br>CAGGAAGCCGACGCTATCACACTGGATGGCGGCGCTATCTACGAGGCTGGCAAA<br>GAGCACGGCCTGAAGCCCGTCGTGGGCGAGGTGTACGATCAGGAAGTGGGCACC<br>TCCTACTACGCCGTGGCTGTCGTGCGGAGATCCTCCCACGTGACCATCGACACC<br>CTGAAGGGCGTGAAGTCCTGCCACACCGGCATCAACAGAACCGTGGGCTGGAAC<br>GTGCCCGTGGGCTACCTGGTGGAATCCGGCAGACTGTCCGTGATGGGCTGCGAC<br>GTGCTGAAGGCCGTGTCCGATTACTTCGGCGGCTCTTGTGTGCCTGGCGCTGGC<br>GAGACATCCTACTCCGAGTCCCTGTGCAGACTGTGCAGGGGCGACTCTTCTGGC<br>GAGGGCGTGTGCGACAAGTCCCCTCTGGAACGGTACTACGACTACTCCGGCGCC<br>TTCAGATGCCTGGCTGAAGGTGCTGGCGACGTGGCCTTCGTGAAGCACTCCACC<br>GTGCTGGAAAACACCGACGGCAAGACCCTGCCTTCTTGGGGCCAGGCACTGCTG<br>TCCCAGGACTTCGAGCTGCTGTGCCGGGATGGCTCCAGAGCCGATGTGACAGAG<br>TGGCGGCAGTGCCACCTGGCCAGAGTGCCTGCTCATGCTGTGGTCGTGCGCGCC<br>GATACAGATGGCGGCCTGATCTTCCGGCTGCTGAACGAGGGCCAGCGGCTGTTC<br>TCTCACGAGGGCTCCAGCTTCCAGATGTTCTCCAGCGAGGCCTACGGCCAGAAG<br>GACCTGCTGTTCAAGGACTCCACCTCCGAGCTGGTGCCTATCGCCACCCAGACC<br>TATGAGGCTTGGCTGGGCCACGAGTACCTGCACGCTATGAAGGGACTGCTGTGC<br>GACCCCAACCGGCTGCCTCCTTATCTGAGGTGGTGCGTGCTGTCCACCCCCGAG<br>ATCCAGAAATGCGGCGATATGGCCGTGGCCTTTCGGCGGCAGAGACTGAAGCCT<br>GAGATCCAGTCGTGTCCGCCAAGAGCCCTCAGCACTGCATGGAACGGATCCAG<br>GCCGAACAGGTGGACGCCGTGACACTGTCCGGCGAGGATATCTACACCGCCGGA<br>AAGACCTACGGCCTGGTGCCAGCTGCTGGCGAGCATTACGCCCCTGAGGACTCC<br>TCCAACAGCTACTACGTGGTGGCAGTCGTGCGCCGGGACTCCTCTCACGCCTTT<br>ACCCTGGATGAGCTGCGGGGCAAGAGAAGCTGTCACGCCGGCTTTGGAAGCCCT<br>GCCGGATGGGATGTGCCTGTGGGCGCTCTGATCCAGCGGGGCTTCATCAGACCC<br>AAGGACTGTGATGTGCTGACCGCCGTGTCTGAGTTCTTCAACGCCTCCTGTGTG<br>CCCGTGAACAACCCCAAGAACTACCCCTCCAGCCTGTGCGCCCTGTGTGTGGGA<br>GATGAGCAGGGCCGGAACAAATGCGTGGGCAACTCCCAGGAAAGATATTACGGC<br>TACAGAGGCGCCTTCCGGTGTCTGGTGGAAAACGCCGGGGATGTGGCTTTTGTG<br>CGGCACACCACCGTGTTCGACAACACCAATGGCCACAACTCCGAGCCTTGGGCC<br>GCTGAGCTGAGATCCGAGGATTACGAACTGCTGTGTCCCAACGGCGCCAGGGCT<br>GAGGTGTCCCAGTTTGCCGCCTGTAACCTGGCCCAGATCCCTCCCCACGCTGTG<br>ATGGTGCGACCCGACACCAACATCTTCACCGTGTACGGCCTGCTGGACAAGGCC<br>CAGGATCTGTTCGGCGACGACCACAACAAGAACGGGTTCAAGATGTTCGACTCC<br>AGCAACTACCACGGACAGGATCTGCTGTTTAAAGATGCCAACGGCATGCCCGTG<br>CCAGTGGGCGAAAAGACCACCTACAGAGGATGGCTGGGACTGGACTACGTGGCC<br>GCCCTGGAAGGCATGTCCTCCCAGCAGTGTTCCTGA | 143 |
| MTf-I2S | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC | 144 |

TABLE E2-continued

Polynucleotide Coding Sequences of Fusion Constructs

| Name | Polynucleotide Sequence | SEQ ID NO: |
|---|---|---|
| | CTGCACCACCATCATCACCATCACCACCATCACGGAGGCGGTGGAGAGAACCTG<br>TACTTTCAGGGCGGCATGGAAGTGCGTTGGTGCGCCACCTCTGACCCCGAGCAG<br>CACAAGTGCGGCAACATGTCCGAGGCCTTCAGAGAGGCCGGCATCCAGCCTTCT<br>CTGCTGTGTGTGCGGGGCACCTCTGCCGACCATTGCGTGCAGCTGATCGCCGCC<br>CAGGAAGCCGACGCTATCACACTGGATGGCGGCGCTATCTACGAGGCTGGCAAA<br>GAGCACGGCCTGAAGCCCGTCGTGGGCGAGGTGTACGATCAGGAAGTGGGCACC<br>TCCTACTACGCCGTGGCTGTCGTGCGGAGATCCTCCCACGTGACCATCGACACC<br>CTGAAGGGCGTGAAGTCCTGCCACACCGGCATCAACAGAACCGTGGGCTGGAAC<br>GTGCCCGTGGGCTACCTGGTGGAATCCGGCAGACTGTCCGTGATGGGCTGCGAC<br>GTGCTGAAGGCCGTGTCCGATTACTTCGGCGGCTCTTGTGTGCCTGGCGCTGGC<br>GAGACATCCTACTCCGAGTCCCTGTGCAGACTGTGCAGGGGCGACTCTTCTGGC<br>GAGGGCGTGTGCGACAAGTCCCCTCTGGAACGGTACTACGACTACTCCGGCGCC<br>TTCAGATGCCTGGCTGAAGGTGCTGGCGACGTGGCCTTCGTGAAGCACTCCACC<br>GTGCTGGAAAACACCGACGGCAAGACCCTGCCTTCTTGGGGCCAGGCACTGCTG<br>TCCCAGGACTTCGAGCTGCTGTGCCGGGATGGCTCCAGAGCCGATGTGACAGAG<br>TGGCGGCAGTGCCACCTGGCCAGAGTGCCTGCTCATGCTGTGGTCGTGCGCGCC<br>GATACAGATGGCGGCCTGATCTTCCGGCTGCTGAACGAGGGCCAGCGGCTGTTC<br>TCTCACGAGGGCTCCAGCTTCCAGATGTTCTCCAGCGAGGCCTACGCCAGAAG<br>GACCTGCTGTTCAAGGACTCCACCTCCGAGCTGGTGCCTATCGCCACCCAGACC<br>TATGAGGCTTGGCTGGGCCACGAGTACCTGCACGCTATGAAGGGACTGCTGTGC<br>GACCCCAACCGGCTGCCTCCTTATCTGAGGTGGTGCGTGCTGTCCACCCCCGAG<br>ATCCAGAAATGCGGCGATATGGCCGTGGCCTTTCGGCGGCAGAGACTGAAGCCT<br>GAGATCCAGTGCGTGTCCGCCAAGAGCCCTCAGCACTGCATGGAACGGATCCAG<br>GCCGAACAGGTGGACGCCGTGACACTGTCCGGCGAGGATATCTACACCGCCGGA<br>AAGACCTACGGCCTGGTGCCAGCTGCTGGCGAGCATTACGCCCCTGAGGACTCC<br>TCCAACAGCTACTACGTGGTGGCAGTCGTGCGCCGGGACTCCTCTCACGCCTTT<br>ACCCTGGATGAGCTGCGGGCAAGAGAAGCTGTCACGCCGGCTTTGGAAGCCCT<br>GCCGGATGGGATGTGCCTGTGGGCGCTCTGATCCAGCGGGGCTTCATCAGACCC<br>AAGGACTGTGATGTGCTGACCGCCGTGTCTGAGTTCTTCAACGCCTCCTGTGTG<br>CCCGTGAACAACCCAAGAACTACCCCTCCAGCCTGTGCGCCCTGTGTGTGGGA<br>GATGAGCAGGGCCGGAACAAATGCGTGGGCAACTCCCAGGAAAGATATTACGGC<br>TACAGAGGCGCCTTCCGGTGTCTGGTGGAAAACGCCGGGGATGTGGCTTTTGTG<br>CGGCACACCACCGTGTTCGACAACACCAATGGCCACAACTCCGAGCCTTGGGCC<br>GCTGAGCTGAGATCCGAGGATTACGAACTGCTGTGTCCCAACGGCGCCAGGGCT<br>GAGGTGTCCCAGTTTGCCGCCTGTAACCTGGCCCAGATCCCTCCCCACGCTGTG<br>ATGGTGCGACCCGACACCAACATCTTCACCGTGTACGGCCTGCTGGACAAGGCC<br>CAGGATCTGTTCGGCGACGACCACAACAAGAACGGGTTCAAGATGTTCGACTCC<br>AGCAACTACCACGGACAGGATCTGCTGTTTAAAGATGCCACCGTGCGGGCCGTG<br>CCAGTGGGCGAAAAGACCACCTACAGAGGATGGCTGGGACTGGACTACGTGGCC<br>GCCCTGGAAGGCATGTCCTCCCAGCAGTGTTCCGAAGCCGCCGCGAAAGAAGCC<br>GCCGCAAAAGAAGCCGCTGCCAAATCGGAAACTCAGGCCAACTCCACCACAGAT<br>GCACTCAACGTGCTGCTGATCATCGTAGATGACCTCCGACCTTCTCTGGGCTGT<br>TACGGCGACAAGCTAGTACGGAGCCCAAACATCGACCAGCTCGCATCGCACTCT<br>CTCCTATTCCAGAACGCATTCGCCCAGCAGGCTGTCTGTGCTCCCTCCCGAGTG<br>TCCTTCCTCACGGGTCGGAGACCCGATACCACGAGGTTATATGACTTCAACTCA<br>TACTGGCGCGTGCATGCCGGTAACTTTTCTACTATACCCCAGTATTTTAAAGAA<br>AATGGCTATGTTACAATGTCCGTTGGCAAGGTATTTCATCCTGGTATTAGCAGC<br>AACCACACAGATGACTCTCCGTATAGCTGGTCATTCCCACCATACCACCCCTCC<br>AGCGAAAAGTACGAAAACAAAGACTTGCCGGGGCCCAGATGGCGAACTGCAC<br>GCAAATCTGCTGTGCCCTGTAGATGTCTTGGACGTGCCCGAAGGTACTCTGCCC<br>GACAAACAGTCCACAGAACAGGCAATCCAACTCCTTGAAAAGATGAAAACGAGC<br>GCGTCCCCCTTCTTCCTCGCCGTGGGCTACCACAAGCCCCACATCCCGTTTAGA<br>TACCCCAAGGAATTTCAGAAACTGTACCCCCTGGAAAACATCACTCTCGCGCCC<br>GACCCCGAAGTGCCAGACGGACTCCCTCCTGTTGCCTACAACCCTTGGATGGAC<br>ATCGACAACGTGAAGATGTGCAGGCCCTGAACATCTCAGTGCCTTACGGCCCC<br>ATTCCAGTTGACTTCCAGAGGAAGATTCGGCAGTCCTACTTCGCCTCCGTTAGT<br>TACCTGGACACCCAAGTGGGTAGACTCCTGAGCGCCTTGGACGATCTCCAGCTC<br>GCAAACAGCACCATCATTGCCTTCACCAGCGACCATGGTTGGGCGCTGGGTGAA<br>CATGGAGAATGGGCTAAATATTCAAATTTCGACGTTGCGACCCACGTCCCATTG<br>ATCTTCTACGTGCCTGGACGAACAGCCTCCTTGCCTGAAGCCGGGGAAAAGTTG<br>TTTCCATATCTGGACCCTTTCGATTCTGCGAGCCAACTCATGGAACCTGGGCGA<br>CAGAGCATGGACCTGGTGGAACTGGTCAGTTTATTTCCAACCCTGGCAGGCCTT<br>GCAGGCCTCCAAGTTCCACCTCGGTGTCCCGTTCCCTCATTCCACGTCGAACTC<br>TGTCGCGAAGGTAAAAACCTCCTCAAGCATTTTCGTTTTCGGGACCTCGAAGAA<br>GACCCATACCTGCCAGGGAATCCAAGGGAACTGATTGCCTACAGCCAGTACCCT<br>AGACCTAGCGACATCCCACAGTGGAACAGCGACAAGCCCTCCCTCAAGGACATT<br>AAAATCATGGGTTATAGTATCCGGACTATTGACTACAGGTATACCGTGTGGGTG<br>GGTTTCAACCCAGACGAATTTCTCGCCAATTTCTCCGACATCCACGGGGCGAA<br>CTGTATTTCGTTGATTCCGATCCACTGCAAGATCATAATATGTACAACGATAGT<br>CAAGGGGGTGACCTCTTCCAGTTGCTAATGCCATGA | |
| MTfpep-<br>I2S | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCGACTCCTCTCACGCCTTCACCCTGGACGAGCTGCGGTACGAA | 145 |

TABLE E2-continued

Polynucleotide Coding Sequences of Fusion Constructs

| Name | Polynucleotide Sequence | SEQ ID NO: |
|---|---|---|
| | GCCGCCGCGAAAGAAGCCGCCGCAAAAGAAGCCGCTGCCAAATCGGAAACTCAG<br>GCCAACTCCACCACAGATGCACTCAACGTGCTGCTGATCATCGTAGATGACCTC<br>CGACCTTCTCTGGGCTGTTACGGCGACAAGCTAGTACGGAGCCCAAACATCGAC<br>CAGCTCGCATCGCACTCTCTCCTATTCCAGAACGCATTCGCCCAGCAGGCTGTC<br>TGTGCTCCCTCCCGAGTGTCCTTCCTCACGGGTCGGAGACCCGATACCACGAGG<br>TTATATGACTTCAACTCATACTGGCGCGTGCATGCCGGTAACTTTTCTACTATA<br>CCCCAGTATTTTAAAGAAAATGGCTATGTTACAATGTCCGTTGGCAAGGTATTT<br>CCCCAGTATTTTAAAGAAAATGGCTATGTTACAATGTCCGTTGGCAAGGTATTT<br>CATCCTGGTATTAGCAGCAACCACACAGATGACTCTCCGTATAGCTGGTCATTC<br>CCACCATACCACCCCTCCAGCGAAAAGTACGAAAACACAAAGACTTGCCGGGGC<br>CCAGATGGCGAACTGCACGCAAATCTGCTGTGCCCTGTAGATGTCTTGGACGTG<br>CCCGAAGGTACTCTGCCCGACAAACAGTCCACAGAACAGGCAATCCAACTCCTT<br>GAAAAGATGAAAACGAGCGCGTCCCCCTTCTTCCTCGCCGTGGGCTACCACAAG<br>CCCCACATCCCGTTTAGATACCCCAAGGAATTTCAGAAACTGTACCCCCTGGAA<br>AACATCACTCTCGCGCCCGACCCCGAAGTGCCAGACGGACTGGGTCCTGTTGCC<br>TACAACCCTTGGATGGACATCAGACAACGTGAAGATGTGCAGGCCCTGAACATC<br>TCAGTGCCTTACGGCCCCATTCCAGTTGACTTCCAGAGGAAGATTCGGCAGTCC<br>TACTTCGCCTCCGTTAGTTACCTGGACACCCAAGTGGGTAGACTCCTGAGCGCC<br>TTGGACGATCTCCAGCTCGCAAACAGCACCATCATTGCCTTCACCAGCGACCAT<br>GGTTGGGCGCTGGGTGAACATGGAGAATGGGCTAAATATTCAAATTTCGACGTT<br>GCGACCCACGTCCCATTGATCTTCTACGTGCCTGGACGAACAGCCTCCTTGCCT<br>GAAGCCGGGGAAAAGTTGTTTCCATATCTGGACCCTTTCGATTCTGCGAGCCAA<br>CTCATGGAACCTGGGCGACAGAGCATGGACCTGGTGGAACTGGTCAGTTTATTT<br>CCAACCCTGGCAGGCCTTGCAGGCCTCCAAGTTCCACCTCGGTGTCCCGTTCCC<br>TCATTCCACGTCGAACTCTGTCGCGAAGGTAAAAACCTCCTCAAGCATTTTCGT<br>TTTCGGGACCTCGAAGAAGACCCATACCTGCCAGGGAATCCAAGGGAACTGATT<br>GCCTACAGCCAGTACCCTAGACCTAGCGACATCCCACAGTGGAACAGCGACAAG<br>CCCTCCCTCAAGGACATTAAAATCATGGGTTATAGTATCCGGACTATTGACTAC<br>AGGTATACCGTGTGGGTGGGTTTCAACCCAGACGAATTTCTCGCCAATTTCTCC<br>GACATCCACGCGGGCGAACTGTATTTCGTTGATTCCGATCCACTGCAAGATCAT<br>AATATGTACAACGATAGTCAAGGGGGTGACCTCTTCCAGTTGCTAATGCCATGA | |
| I2S-<br>MTfpep | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCTCGGAAACTCAGGCCAACTCCACCACAGATGCACTCAACGTG<br>CTGCTGATCATCGTAGATGACCTCCGACCTTCTCTGGGCTGTTACGGCGACAAG<br>CTAGTACGGAGCCCAAACATCGACCAGCTCGCATCGCACTCTCTCCTATTCCAG<br>AACGCATTCGCCCAGCAGGCTGTCTGTGCTCCCTCCCGAGTGTCCTTCCTCACG<br>GGTCGGAGACCCGATACCACGAGGTTATATGACTTCAACTCATACTGGCGCGTG<br>CATGCCGGTAACTTTTCTACTATACCCCAGTATTTTAAAGAAAATGGCTATGTT<br>ACAATGTCCGTTGGCAAGGTATTTCATCCTGGTATTAGCAGCAACCACACAGAT<br>GACTCTCCGTATAGCTGGTCATTCCCACCATACCACCCCTCCAGCGAAAAGTAC<br>GAAAACACAAAGACTTGCCGGGGCCCAGATGGCGAACTGCACGCAAATCTGCTG<br>TGCCCTGTAGATGTCTTGGACGTGCCCGAAGGTACTCTGCCCGACAAACAGTCC<br>ACAGAACAGGCAATCCAACTCCTTGAAAAGATGAAAACGAGCGCGTCCCCCTTC<br>TTCCTCGCCGTGGGCTACCACAAGCCCCACATCCCGTTTAGATACCCCAAGGAA<br>TTTCAGAAACTGTACCCCCTGGAAAACATCACTCTCGCGCCCGACCCCGAAGTG<br>CCAGACGGACTCCCTCCTGTTGCCTACAACCCTTGGATGGACATCAGACAACGT<br>GAAGATGTGCAGGCCCTGAACATCTCAGTGCCTTACGGCCCCATTCCAGTTGAC<br>TTCCAGAGGAAGATTCGGCAGTCCTACTTCGCCTCCGTTAGTTACCTGGACACC<br>CAAGTGGGTAGACTCCTGAGCGCCTTGGACGATCTCCAGCTCGCAAACAGCACC<br>ATCATTGCCTTCACCAGCGACCATGGTTGGGCGCTGGGTGAACATGGAGAATGG<br>GCTAAATATTCAAATTTCGACGTTGCGACCCACGTCCCATTGATCTTCTACGTG<br>CCTGGACGAACAGCCTCCTTGCCTGAAGCCGGGGAAAAGTTGTTTCCATATCTG<br>GACCCTTTCGATTCTGCGAGCCAACTCATGGAACCTGGGCGACAGAGCATGGAC<br>CTGGTGGAACTGGTCAGTTTATTTCCAACCCTGGCAGGCCTTGCAGGCCTCCAA<br>GTTCCACCTCGGTGTCCCGTTCCCTCATTCCACGTCGAACTCTGTCGCGAAGGT<br>AAAAACCTCCTCAAGCATTTTCGTTTTCGGGACCTCGAAGAAGACCCATACCTG<br>CCAGGGAATCCAAGGGAACTGATTGCCTACAGCCAGTACCCTAGACCTAGCGAC<br>ATCCCACAGTGGAACAGCGACAAGCCCTCCCTCAAGGACATTAAAATCATGGGT<br>TATAGTATCCGGACTATTGACTACAGGTATACCGTGTGGGTGGGTTTCAACCCA<br>GACGAATTTCTCGCCAATTTCTCCGACATCCACGCGGGCGAACTGTATTTCGTT<br>GATTCCGATCCACTGCAAGATCATAATATGTACAACGATAGTCAAGGGGGTGAC<br>CTCTTCCAGTTGCTAATGCCAGAGGCCGCTGCTAAAGAGGCTGCCGCCAAAGAA<br>GCCGCCGCTAAGGACTCCTCTCACGCCTTCACCCTGGACGAGCTGCGGTACTAA | 146 |
| I2S-<br>MTfpep<br>(without<br>propep of<br>I2S) | ATGGAATGGAGCTGGGTCTTTCTCTTCTTCCTGTCAGTAACGACTGGTGTCCAC<br>TCCGACTACAAGGACGACGACGACAAAGAGCAGAAGCTGATCTCCGAAGAGGAC<br>CTGCACCACCATCATCACCATCACCACCATCACGGAGGCGGTGGAGAGAACCTG<br>TACTTTCAGGGCACAGATGCACTCAACGTGCTGCTGATCATCGTAGATGACCTC<br>CGACCTTCTCTGGGCTGTTACGGCGACAAGCTAGTACGGAGCCCAAACATCGAC<br>CAGCTCGCATCGCACTCTCTCCTATTCCAGAACGCATTCGCCCAGCAGGCTGTC<br>TGTGCTCCCTCCCGAGTGTCCTTCCTCACGGGTCGGAGACCCGATACCACGAGG<br>TTATATGACTTCAACTCATACTGGCGCGTGCATGCCGGTAACTTTTCTACTATA | 147 |

TABLE E2-continued

Polynucleotide Coding Sequences of Fusion Constructs

| Name | Polynucleotide Sequence | SEQ ID NO: |
|------|------------------------|------------|
| | CCCCAGTATTTTAAAGAAAATGGCTATGTTACAATGTCCGTTGGCAAGGTATTT<br>CATCCTGGTATTAGCAGCAACCACACAGATGACTCTCCGTATAGCTGGTCATTC<br>CCACCATACCACCCCTCCAGCGAAAAGTACGAAAACACAAAGACTTGCCGGGGC<br>CCAGATGGCGAACTGCACGCAAATCTGCTGTGCCCTGTAGATGTCTTGGACGTG<br>CCCGAAGGTACTCTGCCCGACAAACAGTCCACAGAACAGGCAATCCAACTCCTT<br>GAAAAGATGAAAACGAGCGCGTCCCCCTTCTTCCTCGCCGTGGGCTACCACAAG<br>CCCCACATCCCGTTTAGATACCCCAAGGAATTTCAGAAACTGTACCCCCTGGAA<br>AACATCACTCTCGCGCCCGACCCCGAAGTGCCAGACGGACTCCCTCCTGTTGCC<br>TACAACCCTTGGATGGACATCAGACAACGTGAAGATGTGCAGGCCCTGAACATC<br>TCAGTGCCTTACGGCCCCATTCCAGTTGACTTCCAGAGGAAGATTCGGCAGTCC<br>TACTTCGCCTCCGTTAGTTACCTGGACACCCAAGTGGGTAGACTCCTGAGCGCC<br>TTGGACGATCTCCAGCTCGCAAACAGCACCATCATTGCCTTCACCAGCGACCAT<br>GGTTGGGCGCTGGGTGAACATGGAGAATGGGCTAAATATTCAAATTTCGACGTT<br>GCGACCCACGTCCCATTGATCTTCTACGTGCCTGGACGAACAGCCTCCTTGCCT<br>GAAGCCGGGGAAAAGTTGTTTCCATATCTGGACCCTTTCGATTCTGCGAGCCAA<br>CTCATGGAACCTGGGCGACAGAGCATGGACCTGGTGGAACTGGTCAGTTTATTT<br>CCAACCCTGGCAGGCCTTGCAGGCCTCCAAGTTCCACCTCGGTGTCCCGTTCCC<br>TCATTCCACGTCGAACTCTGTCGCGAAGGTAAAAACCTCCTCAAGCATTTTCGT<br>TTTCGGGACCTCGAAGAAGACCCATACCTGCCAGGGAATCCAAGGGAACTGATT<br>GCCTACAGCCAGTACCCTAGACCTAGCGACATCCCACAGTGGAACAGCGACAAG<br>CCCTCCCTCAAGGACATTAAAATCATGGGTTATAGTATCCGGACTATTGACTAC<br>AGGTATACCGTGTGGGTGGGTTTCAACCCAGACGAATTTCTCGCCAATTTCTCC<br>GACATCCACGCGGGCGAACTGTATTTCGTTGATTCCGATCCACTGCAAGATCAT<br>AATATGTACAACGATAGTCAAGGGGGTGACCTCTTCCAGTTGCTAATGCCAGAG<br>GCCGCTGCTAAAGAGGCTGCCGCCAAAGAAGCCGCCGCTAAGGACTCCTCTCAC<br>GCCTTCACCCTGGACGAGCTGCGGTACTAA | |

Figure 3:
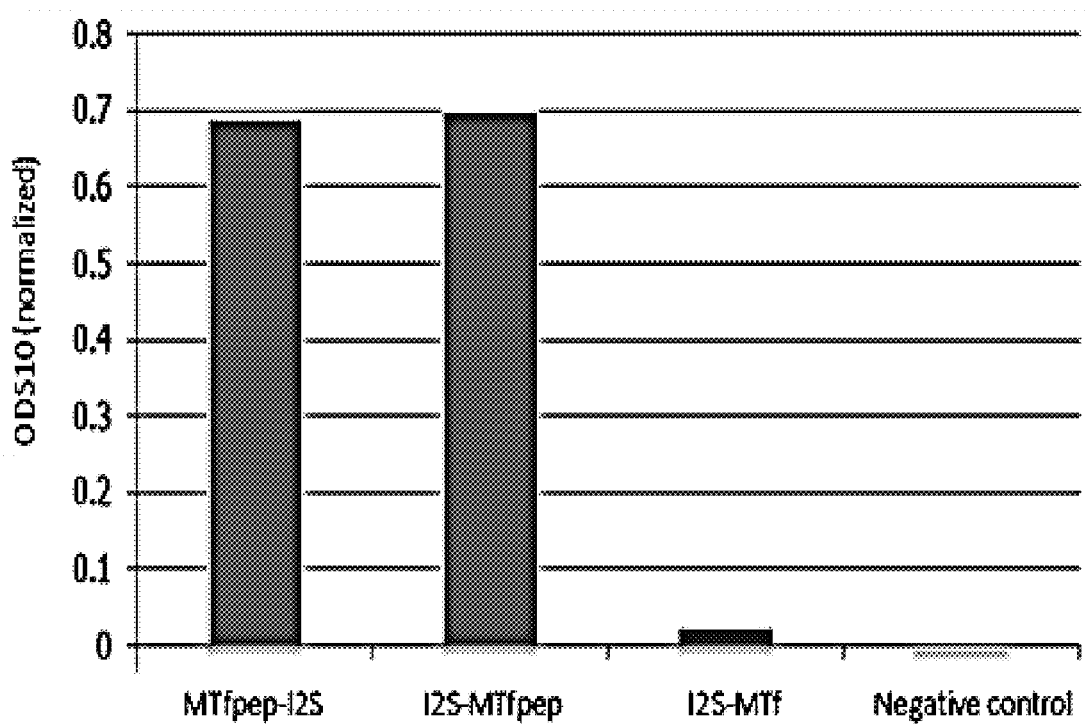
FIG. 3 shows the enzyme activity evaluation of MTfpep-I2S and I2S-MTfpep (with I2S propeptide) fusion proteins as measured by their ability to hydrolyze the substrate PNCS relative to I2S-MTf fusion and negative control (TZM-MTf fusion). 1 ug of each sample was used in the enzyme activity assay, and data presented are normalized to substrate blank.
Figure 4:
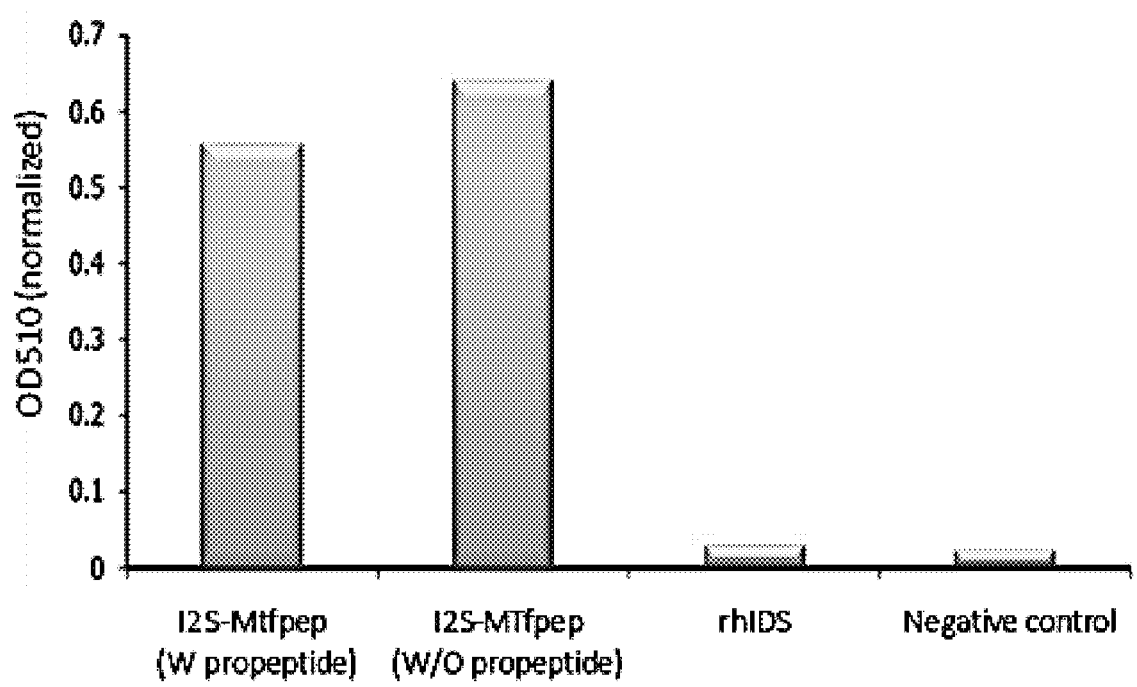
FIG. 4 shows a comparison of the enzyme activity of I2S-MTfpep (with I2S propeptide) and I2S-MTfpep (without I2S propeptide) fusion proteins as measured by their ability to hydrolyze the substrate PNCS. 1 ug of each sample was used in the enzyme activity assay, and data presented are normalized to substrate blank.

Recombinant proteins were prepared and tested for enzymatic activity against the substrate 4-Nitrocatechol Sulfate (PNCS) relative to recombinant human IDS and a negative control (trastuzumab-MTf fusion). The results are shown in FIGS. 2-4. One g of each sample was used in the enzyme activity assay, and the data presented are normalized to substrate blank.

FIG. 2 shows the enzyme activity evaluation of I2S-MTf and MTf-I2S fusion proteins as measured by their ability to hydrolyze the substrate 4-Nitrocatechol Sulfate (PNCS) relative to recombinant human IDS and negative control (TZM-MTf fusion). These data show that the I2S-MTf and MTf-I2S fusion proteins not only had significant enzymatic activity, but also had increased enzymatic activity relative to wild-type (non-fusion) human IDS.

FIG. 3 shows the enzyme activity evaluation of MTfpep-I2S and I2S-MTfpep (with I2S propeptide) fusion proteins as measured by their ability to hydrolyze the substrate PNCS relative to I2S-MTf fusion and negative control (TZM-MTf fusion). These data show that the MTfpep-I2S and I2S-MTfpep fusion proteins not only had significant enzymatic activity, but also had increased enzymatic activity relative to the significantly active I2S-MTf fusion protein (from FIG. 2), and thus increased enzymatic activity relative to wild-type (non-fusion) human IDS.

FIG. 4 shows a comparison of the enzyme activity of I2S-MTfpep (with I2S propeptide) and I2S-MTfpep (without I2S propeptide) fusion proteins as measured by their ability to hydrolyze the substrate PNCS. These data show that the MTfpep-I2S and I2S-MTfpep fusion proteins not only had significant enzymatic activity, but also had increased enzymatic activity relatively to wild-type (non-fusion) human IDS.

Example 2

In Vivo Distribution of I2S-MTf and MTfpep-I2S Fusions in the Brain

The brain biodistribution of the I2S-MTf and MTfpep-I2S fusion proteins in mice was evaluated by quantitative confocal microscopy imaging. Therapeutic dose equivalents of I2S-MTf and MTfpep-I2S were administered in 100 μL volume to mice via tail vein injection. Prior to euthanasia, mice were injected (i.v.) with Tomato Lectin-FITC (40 μg) for 10 min to stain the brain vasculature. Blood was cleared by intracardiac perfusion of 10 ml heparinised saline at a rate of 1 ml per minute. Brains were excised and frozen in OCT and stored at −80° C. Brains were mounted in Tissue Tek and sectioned with a cryostat at −20° C. Sections were mounted on Superfrost Plus microscope slides, fixed in cold Acetone/MeOH (1:1) for 10 minutes at room temperature, and washed with PBS. Glass coverslips were mounted on sections using Prolong Gold antifade reagent with DAPI (molecular probes, P36931). Three-dimensional (3D) confocal microscopy and quantitative analysis was performed.

Figure 5:
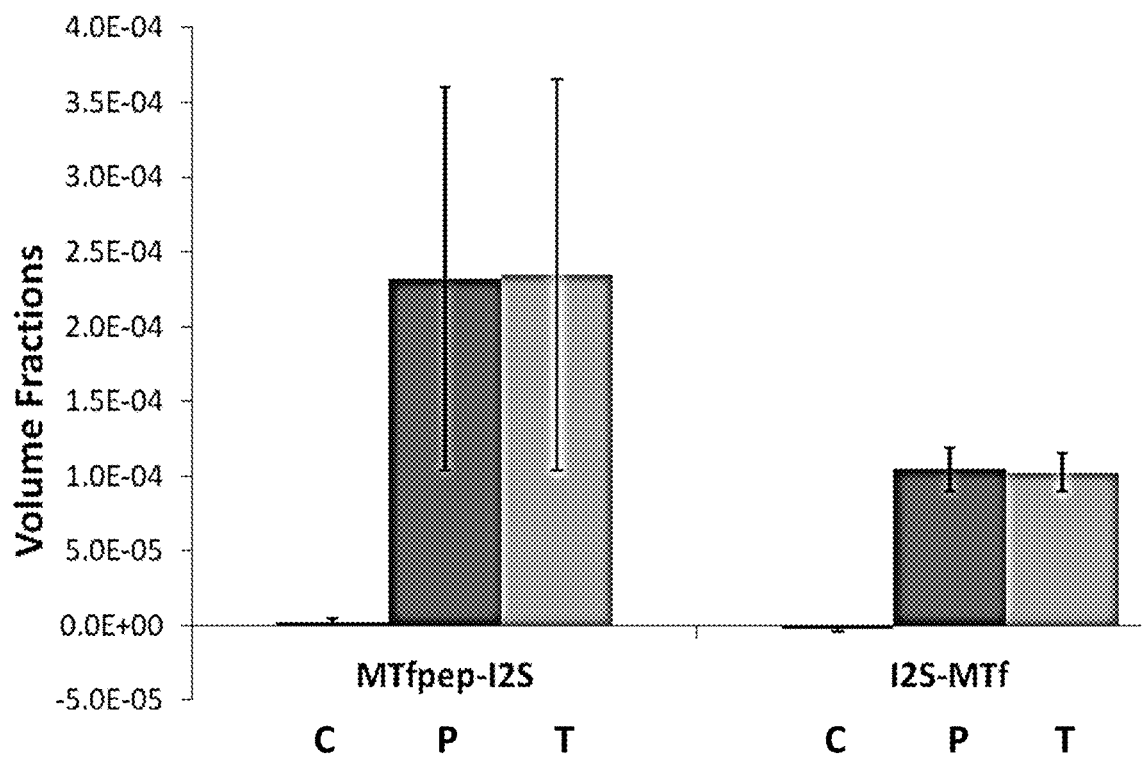
FIG. 5 shows quantification of the relative distribution of MTfpep-I2S (with propeptide) and I2S-MTf fusion proteins between capillaries (C) and parenchyma (P) in the brain, relative to the total (T) signal. Quantitative confocal microscopy imaging shows that both the MTfpep-I2S and I2S-MTf fusion proteins were strongly associated with parenchymal tissues of the CNS.

FIG. 5 shows quantification of the relative distribution of MTfpep-I2S (with propeptide) and I2S-MTf fusion proteins between capillaries (C) and parenchyma (P) in the brain, relative to the total (T) signal. The significant staining of parenchymal tissues relative to capillaries confirms that the MTfpep-I2S and I2S-MTf fusion proteins were both able to cross the blood brain barrier (BBB) and accumulate in tissues of the central nervous system.

In summary, the data from Examples 1 and 2 show that the MTfpep-I2S (with propeptide) and I2S-MTf fusion proteins are not only able to cross the BBB and accumulate in tissues of the CNS, but also have significantly increased enzymatic activity relative to wild-type (non-fusion) recombinant human IDS.

Example 3

In Vivo Activity of I2S-MTf and MTfpep-I2S Fusions in Mouse Model of MPS II

The therapeutic efficacy of the I2S-MTf and MTfpep-I2S fusion proteins is evaluated in a mouse model of Hunter Syndrome or Mucopolysaccharidosis type II (MPS II) relative to Idursulfase (Elaprase®), which is indicated for the treatment of Hunter Syndrome. These studies are designed to evaluate the effect of intravenous (IV) and intraperitoneal (IP) administration of the fusion proteins on brain pathology in a knock-out mouse model of Mucopolysaccharidosis II (MPSII).

Hunter Syndrome.

As noted above, Hunter Syndrome is an X-linked recessive disease caused by insufficient levels of the lysosomal enzyme iduronate 2-sulfatase (IDS). This enzyme cleaves the terminal 2-O-sulfate moieties from the glycosaminoglycans (GAG) dermatan-sulfate and heparan-sulfate. Due to the missing or defective IDS enzyme activity in patients with Hunter syndrome, GAG accumulate progressively in the lysosomes of a variety of cell types. This leads to cellular engorgement, organomegaly, tissue destruction, and organ system dysfunction.

Mouse Model.

IDS-KO mice have little or no tissue IDS activity and exhibit many of the cellular and clinical effects observed in Hunter's syndrome including increased tissue vacuolization, GAG levels, and urinary excretion of GAG. Due to the X-linked recessive nature of Hunter syndrome, all pharmacology studies are performed in male mice. Animal breeding is performed as described by Garcia et al, 2007 (3). Briefly, carrier females are bred with wild type male mice of the C57Bl/6 background strain, producing heterogenous females and hemizygous male knock-out mice, as well as wild-type (WT) males and females. IDS-KO male mice are alternatively obtained by breeding carrier females with IDS-KO male mice. The genotype of all mice used in these experiments is confirmed by polymerase chain reaction of DNA obtained from tail snip. All IDS-KO mice are hemizygous IKO (−/0) male and between 12-13 weeks old at the beginning of treatment initiation (mice younger than 12 weeks are not used in this study). A group of untreated WT littermate (+/0) males are used as controls.

Idursulfase (Elaprase®).

Idursulfase is a drug used to treat Hunter syndrome (also called MPS-II) (see Garcia et al., Mol Genet Metab. 91:183-90, 2007). It is a purified form of the lysosomal enzyme iduronate-2-sulfatase and is produced by recombinant DNA technology in a human cell line Study Design.

The study design is outlined in Table E3 below.

TABLE E3

| Group | Animal | Mice/Group | Dose level (mg/kg) | Dose volume (mL/kg) | Treatment regimen | Sacrifice |
|---|---|---|---|---|---|---|
| Vehicle (control) | WT | 5 | 0 | 5-6 | IV, once per week for 6 wks | 24 h after last injection |
| Vehicle (control) | IDS-KO | 5 | 0 | 5-6 | IV, once per week for 6 wks | 24 h after last injection |
| IDS (Elaprase) (high dose) | IDS-KO | 5 | 6 mg/kg | 5-6 | IV, bi-weekly for 6 wks | 24 h after last injection |
| hMTf | IDS-KO | 3-5 | Molar equivalent to hMTf-IDS dose | 5-6 | IV, once per week for 6 wks | 24 h after last injection |
| IDS-hMTf | IDS-KO | 5 | Activity equivalent to IDS (high dose) | 5-6 | IV, once per week for 6 wks | 24 h after last injection |
| hMTfpep-IDS | IDS-KO | 5 | Activity equivalent to IDS (high dose) | 5-6 | IV, once per week for 6 wks | 24 h after last injection |

All test articles and vehicle controls are administered by two slow bolus (one IV and one IP injection), to be performed once a week for a total of 6 weeks.

Body weights are determined at randomization on the first day of treatment and weekly thereafter. Clinical observations are performed daily. The animals are sacrificed approximately 24 hours after the last treatment.

Selected organs (brain, liver, kidney and heart) are collected and their weights recorded. The brains are preserved for histopathology and immunostaining analysis. The other tissues are divided with one half or one paired organ and preserved for histopathology and immunostaining in a manner similar to the brain. The other half or paired organ is frozen in liquid nitrogen and stored at −80° C. until assayed for GAG.

Study End Points:

The primary endpoints are as follows:

Histological evaluation: Hematoxylin and eosin staining of brain sections. This method is used to evaluate whether treatment has an effect on reducing the number/size of cellular storage vacuoles observed in IDS-KO mice; and Immunohistochemical evaluation of lysosomal associated membrane protein-1 (LAMP-1) in brain sections: This method is used to determine if treatment has effect on reducing the elevated LAMP-1 immunoreactivity that is observed in IDS-KO mice.

If feasible, qualitative or semi-qualitative methods are also employed for analysis of the end points 1-2 (such as scoring, area measurements, section scans, etc.). The histopathologist performing this analysis is blinded with regard to slide allocation to the study groups. Lysosome surface area is quantified by scanning areas stained for LAMP1 (IHC) and compared between experimental groups.

The secondary endpoints are as follows:

GAG levels in selected tissues (liver, kidney, and heart);

H&E staining of selected tissues and detection of cellular storage vacuoles; and Immunohistochemical evaluation of LAMP-1 levels in selected organs/tissues.

Histopathology (H&E Stain).

Tissues are collected and fixed in 10% neutral buffered formalin, then processed and embedded in paraffin. 5 μm paraffin sections are prepared and stained with hematoxylin and eosin (H&E) using standard procedures.

Immunohistochemistry (LAMP-1).

Deparaffinized slides are incubated overnight with rat anti-LAMP-1 IgG (Santa CruzBiotechnology) as the primary antibody or rat IgG2a as a control antibody (AbDSerotec, Raleigh, N.C.). Following overnight incubation at 2-8° C., biotinylated rabbit anti-rat IgG (H&L)mouse adsorbed (Vector Laboratories) is added. Following 30 minutes of incubation at 37° C., samples are washed and then treated with avidin-biotin-peroxidase complex (Vector Laboratories) for 30 minutes. Labeled protein is localized by incubation with 3,39-diaminobenzidine. The area of LAMP-1-positive cells is analyzed with Image-Pro Plus software (Media Cybernetics, Inc., Bethesda, Md.).

GAG Measurements.

Tissue extracts are prepared by homogenizing tissue in a lysis buffer (10 mM Tris, 5 mM EDTA, 0.1% Igepal CA-630, 2 mM Pefabloc SC) using a glass grinder (Kontes Glass Company, Vineland, N.J.) or a motorized tissue homogenizer (PowerGen Model 125, Omni International, Warrenton, Va.). Homogenates re then subjected to 5 freeze-thaw cycles using an ethanol/dry ice bath and a 37° C. water bath. Tissue debris is pelleted twice by room temperature centrifugation at 2000 g for 12 minutes, and supernatants are collected and assayed for total protein concentration (mg/mL) using the bicinchonic acid (BCA) assay (Pierce, Rockford, Ill.).

GAG concentration in urine and tissue extracts is quantified by acolorimetric assay using 1,9-dimethylmethylene blue (DMB) dye and a standard curve (1.56-25 μg/mL) prepared from dermatan sulfate (MP Biomedicals, Aurora, Ohio). Urine samples are run at dilutions of 1/10, 1/20, and 1/40. To avoid assay interference from protein, tissue extract samples are diluted to protein concentrations of <200 μg/mL. GAG concentrations in urine is adjusted for creatinine concentrations measured with a commercially available kit (Sigma, St. Louis, Mo., part no. 555A) to compensate for differences in kidney function and expressed as μg GAG/mg creatinine. GAG levels in tissue extracts are adjusted for protein concentration (μg GAG/mg protein) or gram tissue.

The invention claimed is:

1. A pharmaceutical composition comprising a p97 (melanotransferrin) fusion protein comprising: (i) an iduronate-2-sulfatase (IDS) polypeptide fused to the C-terminus of a p97 polypeptide fragment and an optional heterologous peptide linker (L) in between, wherein the p97 polypeptide fragment consists of the amino acid sequence having at least 80% sequence identity to DSSHAFTLDELR (SEQ ID NO:14) and having transport activity; and (ii) a pharmaceutically acceptable carrier.

2. The pharmaceutical composition of claim 1 which is sterile and non-pyrogenic.

3. The pharmaceutical composition of claim 1 wherein the pharmaceutically acceptable carrier is in the form of a liquid, semi-liquid or a solid.

4. The pharmaceutical composition of claim 1 wherein the pharmaceutically acceptable carrier is a saline solution.

5. A pharmaceutical composition comprising a p97 (melanotransferrin) fusion protein comprising: (i) an iduronate-2-sulfatase (IDS) polypeptide fused to the N-terminus of a p97 polypeptide fragment and an optional heterologous peptide linker (L) in between, wherein the p97 polypeptide fragment consists of the amino acid sequence having at least 80% sequence identity to DSSHAFTLDELR (SEQ ID NO:14) and having transport activity; and (ii) a pharmaceutically acceptable carrier.

6. The pharmaceutical composition of claim 5 which is sterile and non-pyrogenic.

7. The pharmaceutical composition of claim 5 wherein the pharmaceutically acceptable carrier is in the form of a liquid, semi-liquid or a solid.

8. The pharmaceutical composition of claim 5 wherein the pharmaceutically acceptable carrier is a saline solution.

9. A method for the treatment of a lysosomal storage disease in a subject in need thereof comprising administering to the subject the pharmaceutical composition of claim 1.

10. A method according to claim 9 wherein the lysosomal storage disease is Hunter Syndrome (MPSII).

11. A method for the treatment of a lysosomal storage disease in a subject in need thereof comprising administering to the subject the pharmaceutical composition of claim 5.

12. A method according to claim 11 wherein the lysosomal storage disease is Hunter Syndrome (MPSII).

* * * * *

SEQUENCE LISTING

```
<160> NUMBER OF SEQ ID NOS: 149

<210> SEQ ID NO 1
<211> LENGTH: 738
<212> TYPE: PRT
<213> ORGANISM: Homo sapiens

<400> SEQUENCE: 1

Met Arg Gly Pro Ser Gly Ala Leu Trp Leu Leu Leu Ala Leu Arg Thr
1               5                   10                  15

Val Leu Gly Gly Met Glu Val Arg Trp Cys Ala Thr Ser Asp Pro Glu
            20                  25                  30

Gln His Lys Cys Gly Asn Met Ser Glu Ala Phe Arg Glu Ala Gly Ile
        35                  40                  45

Gln Pro Ser Leu Leu Cys Val Arg Gly Thr Ser Ala Asp His Cys Val
    50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
            100                 105                 110

Val Arg Arg Ser Ser His Val Thr Ile Asp Thr Leu Lys Gly Val Lys
        115                 120                 125

Ser Cys His Thr Gly Ile Asn Arg Thr Val Gly Trp Asn Val Pro Val
    130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
            180                 185                 190

Ser Ser Gly Glu Gly Val Cys Asp Lys Ser Pro Leu Glu Arg Tyr Tyr
        195                 200                 205
```

```
Asp Tyr Ser Gly Ala Phe Arg Cys Leu Ala Glu Ala Gly Asp Val
    210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
                260                 265                 270

Leu Ala Arg Val Pro Ala His Val Val Arg Ala Asp Thr Asp
            275                 280                 285

Gly Gly Leu Ile Phe Arg Leu Leu Asn Glu Gly Gln Arg Leu Phe Ser
290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
                340                 345                 350

Lys Gly Leu Leu Cys Asp Pro Asn Arg Leu Pro Pro Tyr Leu Arg Trp
            355                 360                 365

Cys Val Leu Ser Thr Pro Glu Ile Gln Lys Cys Gly Asp Met Ala Val
            370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
                420                 425                 430

Gly Leu Val Pro Ala Ala Gly Glu His Tyr Ala Pro Glu Asp Ser Ser
            435                 440                 445

Asn Ser Tyr Tyr Val Val Ala Val Val Arg Arg Asp Ser Ser His Ala
    450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
                500                 505                 510

Phe Phe Asn Ala Ser Cys Val Pro Val Asn Asn Pro Lys Asn Tyr Pro
            515                 520                 525

Ser Ser Leu Cys Ala Leu Cys Val Gly Asp Glu Gln Gly Arg Asn Lys
530                 535                 540

Cys Val Gly Asn Ser Gln Glu Arg Tyr Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
                580                 585                 590

Glu Leu Arg Ser Glu Asp Tyr Glu Leu Leu Cys Pro Asn Gly Ala Arg
            595                 600                 605

Ala Glu Val Ser Gln Phe Ala Ala Cys Asn Leu Ala Gln Ile Pro Pro
610                 615                 620

His Ala Val Met Val Arg Pro Asp Thr Asn Ile Phe Thr Val Tyr Gly
```

```
                625                 630                 635                 640
Leu Leu Asp Lys Ala Gln Asp Leu Phe Gly Asp Asp His Asn Lys Asn
                    645                 650                 655
Gly Phe Lys Met Phe Asp Ser Ser Asn Tyr His Gly Gln Asp Leu Leu
                    660                 665                 670
Phe Lys Asp Ala Thr Val Arg Ala Val Pro Val Gly Glu Lys Thr Thr
                    675                 680                 685
Tyr Arg Gly Trp Leu Gly Leu Asp Tyr Val Ala Ala Leu Glu Gly Met
                    690                 695                 700
Ser Ser Gln Gln Cys Ser Gly Ala Ala Ala Pro Ala Pro Gly Ala Pro
705                 710                 715                 720
Leu Leu Pro Leu Leu Leu Pro Ala Leu Ala Ala Arg Leu Leu Pro Pro
                    725                 730                 735
Ala Leu

<210> SEQ ID NO 2
<211> LENGTH: 692
<212> TYPE: PRT
<213> ORGANISM: Homo sapiens

<400> SEQUENCE: 2

Gly Met Glu Val Arg Trp Cys Ala Thr Ser Asp Pro Glu Gln His Lys
1               5                   10                  15
Cys Gly Asn Met Ser Glu Ala Phe Arg Glu Ala Gly Ile Gln Pro Ser
                20                  25                  30
Leu Leu Cys Val Arg Gly Thr Ser Ala Asp His Cys Val Gln Leu Ile
            35                  40                  45
Ala Ala Gln Glu Ala Asp Ala Ile Thr Leu Asp Gly Gly Ala Ile Tyr
        50                  55                  60
Glu Ala Gly Lys Glu His Gly Leu Lys Pro Val Val Gly Glu Val Tyr
65                  70                  75                  80
Asp Gln Glu Val Gly Thr Ser Tyr Tyr Ala Val Ala Val Val Arg Arg
                85                  90                  95
Ser Ser His Val Thr Ile Asp Thr Leu Lys Gly Val Lys Ser Cys His
                100                 105                 110
Thr Gly Ile Asn Arg Thr Val Gly Trp Asn Val Pro Val Gly Tyr Leu
            115                 120                 125
Val Glu Ser Gly Arg Leu Ser Val Met Gly Cys Asp Val Leu Lys Ala
        130                 135                 140
Val Ser Asp Tyr Phe Gly Gly Ser Cys Val Pro Gly Ala Gly Glu Thr
145                 150                 155                 160
Ser Tyr Ser Glu Ser Leu Cys Arg Leu Cys Arg Gly Asp Ser Ser Gly
                165                 170                 175
Glu Gly Val Cys Asp Lys Ser Pro Leu Glu Arg Tyr Tyr Asp Tyr Ser
                180                 185                 190
Gly Ala Phe Arg Cys Leu Ala Glu Gly Ala Gly Asp Val Ala Phe Val
            195                 200                 205
Lys His Ser Thr Val Leu Glu Asn Thr Asp Gly Lys Thr Leu Pro Ser
        210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
                245                 250                 255
Val Pro Ala His Ala Val Val Val Arg Ala Asp Thr Asp Gly Gly Leu
```

```
            260             265             270
Ile Phe Arg Leu Leu Asn Glu Gly Gln Arg Leu Phe Ser His Glu Gly
        275             280             285
Ser Ser Phe Gln Met Phe Ser Ser Glu Ala Tyr Gly Gln Lys Asp Leu
        290             295             300
Leu Phe Lys Asp Ser Thr Ser Glu Leu Val Pro Ile Ala Thr Gln Thr
305             310             315             320
Tyr Glu Ala Trp Leu Gly His Glu Tyr Leu His Ala Met Lys Gly Leu
                325             330             335
Leu Cys Asp Pro Asn Arg Leu Pro Pro Tyr Leu Arg Trp Cys Val Leu
            340             345             350
Ser Thr Pro Glu Ile Gln Lys Cys Gly Asp Met Ala Val Ala Phe Arg
        355             360             365
Arg Gln Arg Leu Lys Pro Glu Ile Gln Cys Val Ser Ala Lys Ser Pro
        370             375             380
Gln His Cys Met Glu Arg Ile Gln Ala Glu Gln Val Asp Ala Val Thr
385             390             395             400
Leu Ser Gly Glu Asp Ile Tyr Thr Ala Gly Lys Thr Tyr Gly Leu Val
                405             410             415
Pro Ala Ala Gly Glu His Tyr Ala Pro Glu Asp Ser Ser Asn Ser Tyr
            420             425             430
Tyr Val Val Ala Val Val Arg Arg Asp Ser Ser His Ala Phe Thr Leu
        435             440             445
Asp Glu Leu Arg Gly Lys Arg Ser Cys His Ala Gly Phe Gly Ser Pro
        450             455             460
Ala Gly Trp Asp Val Pro Val Gly Ala Leu Ile Gln Arg Gly Phe Ile
465             470             475             480
Arg Pro Lys Asp Cys Asp Val Leu Thr Ala Val Ser Glu Phe Phe Asn
                485             490             495
Ala Ser Cys Val Pro Val Asn Asn Pro Lys Asn Tyr Pro Ser Ser Leu
            500             505             510
Cys Ala Leu Cys Val Gly Asp Glu Gln Gly Arg Asn Lys Cys Val Gly
        515             520             525
Asn Ser Gln Glu Arg Tyr Tyr Gly Tyr Arg Gly Ala Phe Arg Cys Leu
        530             535             540
Val Glu Asn Ala Gly Asp Val Ala Phe Val Arg His Thr Thr Val Phe
545             550             555             560
Asp Asn Thr Asn Gly His Asn Ser Glu Pro Trp Ala Ala Glu Leu Arg
                565             570             575
Ser Glu Asp Tyr Glu Leu Leu Cys Pro Asn Gly Ala Arg Ala Glu Val
            580             585             590
Ser Gln Phe Ala Ala Cys Asn Leu Ala Gln Ile Pro Pro His Ala Val
        595             600             605
Met Val Arg Pro Asp Thr Asn Ile Phe Thr Val Tyr Gly Leu Leu Asp
        610             615             620
Lys Ala Gln Asp Leu Phe Gly Asp Asp His Asn Lys Asn Gly Phe Lys
625             630             635             640
Met Phe Asp Ser Ser Asn Tyr His Gly Gln Asp Leu Leu Phe Lys Asp
                645             650             655
Ala Thr Val Arg Ala Val Pro Val Gly Glu Lys Thr Thr Tyr Arg Gly
            660             665             670
Trp Leu Gly Leu Asp Tyr Val Ala Ala Leu Glu Gly Met Ser Ser Gln
        675             680             685
```

Gln Cys Ser Gly
    690

<210> SEQ ID NO 3
<211> LENGTH: 11
<212> TYPE: PRT
<213> ORGANISM: Homo sapiens

<400> SEQUENCE: 3

Trp Cys Ala Thr Ser Asp Pro Glu Gln His Lys
1               5                   10

<210> SEQ ID NO 4
<211> LENGTH: 11
<212> TYPE: PRT
<213> ORGANISM: Homo sapiens

<400> SEQUENCE: 4

Arg Ser Ser His Val Thr Ile Asp Thr Leu Lys
1               5                   10

<210> SEQ ID NO 5
<211> LENGTH: 13
<212> TYPE: PRT
<213> ORGANISM: Homo sapiens

<400> SEQUENCE: 5

Ser Ser His Val Thr Ile Asp Thr Leu Lys Gly Val Lys
1               5                   10

<210> SEQ ID NO 6
<211> LENGTH: 14
<212> TYPE: PRT
<213> ORGANISM: Homo sapiens

<400> SEQUENCE: 6

Leu Cys Arg Gly Asp Ser Ser Gly Glu Gly Val Cys Asp Lys
1               5                   10

<210> SEQ ID NO 7
<211> LENGTH: 16
<212> TYPE: PRT
<213> ORGANISM: Homo sapiens

<400> SEQUENCE: 7

Gly Asp Ser Ser Gly Glu Gly Val Cys Asp Lys Ser Pro Leu Glu Arg
1               5                   10                  15

<210> SEQ ID NO 8
<211> LENGTH: 9
<212> TYPE: PRT
<213> ORGANISM: Homo sapiens

<400> SEQUENCE: 8

Tyr Tyr Asp Tyr Ser Gly Ala Phe Arg
1               5

<210> SEQ ID NO 9
<211> LENGTH: 7
<212> TYPE: PRT
<213> ORGANISM: Homo sapiens

<400> SEQUENCE: 9

Ala Asp Val Thr Glu Trp Arg

-continued

```
<210> SEQ ID NO 10
<211> LENGTH: 9
<212> TYPE: PRT
<213> ORGANISM: Homo sapiens

<400> SEQUENCE: 10

Val Pro Ala His Ala Val Val Val Arg
1               5

<210> SEQ ID NO 11
<211> LENGTH: 10
<212> TYPE: PRT
<213> ORGANISM: Homo sapiens

<400> SEQUENCE: 11

Ala Asp Thr Asp Gly Gly Leu Ile Phe Arg
1               5                   10

<210> SEQ ID NO 12
<211> LENGTH: 9
<212> TYPE: PRT
<213> ORGANISM: Homo sapiens

<400> SEQUENCE: 12

Cys Gly Asp Met Ala Val Ala Phe Arg
1               5

<210> SEQ ID NO 13
<211> LENGTH: 11
<212> TYPE: PRT
<213> ORGANISM: Homo sapiens

<400> SEQUENCE: 13

Leu Lys Pro Glu Ile Gln Cys Val Ser Ala Lys
1               5                   10

<210> SEQ ID NO 14
<211> LENGTH: 12
<212> TYPE: PRT
<213> ORGANISM: Homo sapiens

<400> SEQUENCE: 14

Asp Ser Ser His Ala Phe Thr Leu Asp Glu Leu Arg
1               5                   10

<210> SEQ ID NO 15
<211> LENGTH: 13
<212> TYPE: PRT
<213> ORGANISM: Homo sapiens

<400> SEQUENCE: 15

Ser Glu Asp Tyr Glu Leu Leu Cys Pro Asn Gly Ala Arg
1               5                   10

<210> SEQ ID NO 16
<211> LENGTH: 15
<212> TYPE: PRT
<213> ORGANISM: Homo sapiens

<400> SEQUENCE: 16

Ala Gln Asp Leu Phe Gly Asp Asp His Asn Lys Asn Gly Phe Lys
1               5                   10                  15
```

<210> SEQ ID NO 17
<211> LENGTH: 40
<212> TYPE: PRT
<213> ORGANISM: Homo sapiens

<400> SEQUENCE: 17

Phe Ser Ser Glu Ala Tyr Gly Gln Lys Asp Leu Leu Phe Lys Asp Ser
1               5                   10                  15

Thr Ser Glu Leu Val Pro Ile Ala Thr Gln Thr Tyr Glu Ala Trp Leu
            20                  25                  30

Gly His Glu Tyr Leu His Ala Met
        35                  40

<210> SEQ ID NO 18
<211> LENGTH: 221
<212> TYPE: PRT
<213> ORGANISM: Homo sapiens

<400> SEQUENCE: 18

Glu Arg Ile Gln Ala Glu Gln Val Asp Ala Val Thr Leu Ser Gly Glu
1               5                   10                  15

Asp Ile Tyr Thr Ala Gly Lys Thr Tyr Gly Leu Val Pro Ala Ala Gly
            20                  25                  30

Glu His Tyr Ala Pro Glu Asp Ser Ser Asn Ser Tyr Tyr Val Val Ala
        35                  40                  45

Val Val Arg Arg Asp Ser Ser His Ala Phe Thr Leu Asp Glu Leu Arg
    50                  55                  60

Gly Lys Arg Ser Cys His Ala Gly Phe Gly Ser Pro Ala Gly Trp Asp
65                  70                  75                  80

Val Pro Val Gly Ala Leu Ile Gln Arg Gly Phe Ile Arg Pro Lys Asp
                85                  90                  95

Cys Asp Val Leu Thr Ala Val Ser Glu Phe Phe Asn Ala Ser Cys Val
            100                 105                 110

Pro Val Asn Asn Pro Lys Asn Tyr Pro Ser Ser Leu Cys Ala Leu Cys
        115                 120                 125

Val Gly Asp Glu Gln Gly Arg Asn Lys Cys Val Gly Asn Ser Gln Glu
    130                 135                 140

Arg Tyr Tyr Gly Tyr Arg Gly Ala Phe Arg Cys Leu Val Glu Asn Ala
145                 150                 155                 160

Gly Asp Val Ala Phe Val Arg His Thr Thr Val Phe Asp Asn Thr Asn
                165                 170                 175

Gly His Asn Ser Glu Pro Trp Ala Ala Glu Leu Arg Ser Glu Asp Tyr
            180                 185                 190

Glu Leu Leu Cys Pro Asn Gly Ala Arg Ala Glu Val Ser Gln Phe Ala
        195                 200                 205

Ala Cys Asn Leu Ala Gln Ile Pro Pro His Ala Val Met
    210                 215                 220

<210> SEQ ID NO 19
<211> LENGTH: 32
<212> TYPE: PRT
<213> ORGANISM: Homo sapiens

<400> SEQUENCE: 19

Val Arg Pro Asp Thr Asn Ile Phe Thr Val Tyr Gly Leu Leu Asp Lys
1               5                   10                  15

Ala Gln Asp Leu Phe Gly Asp Asp His Asn Lys Asn Gly Phe Lys Met

<210> SEQ ID NO 20
<211> LENGTH: 564
<212> TYPE: PRT
<213> ORGANISM: Homo sapiens

<400> SEQUENCE: 20

```
Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365
```

```
Arg Gln Arg Leu Lys Pro Glu Ile Gln Cys Val Ser Ala Lys Ser Pro
370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Arg Arg Asp Ser Ser His Ala Phe Thr Leu
        435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
530                 535                 540

Val Glu Asn Ala Gly Asp Val Ala Phe Val Arg His Thr Thr Val Phe
545                 550                 555                 560

Asp Asn Thr Asn

<210> SEQ ID NO 21
<211> LENGTH: 22
<212> TYPE: PRT
<213> ORGANISM: Homo sapiens

<400> SEQUENCE: 21

Gly His Asn Ser Glu Pro Trp Ala Ala Glu Leu Arg Ser Glu Asp Tyr
1               5                   10                  15

Glu Leu Leu Cys Pro Asn
            20

<210> SEQ ID NO 22
<211> LENGTH: 51
<212> TYPE: PRT
<213> ORGANISM: Homo sapiens

<400> SEQUENCE: 22

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp His
        35                  40                  45

Asn Lys Asn
    50

<210> SEQ ID NO 23
<211> LENGTH: 53
<212> TYPE: PRT
<213> ORGANISM: Homo sapiens

<400> SEQUENCE: 23
```

```
Gly Phe Lys Met Phe Asp Ser Ser Asn Tyr His Gly Gln Asp Leu Leu
1               5                   10                  15

Phe Lys Asp Ala Thr Val Arg Ala Val Pro Val Gly Glu Lys Thr Thr
            20                  25                  30

Tyr Arg Gly Trp Leu Gly Leu Asp Tyr Val Ala Ala Leu Glu Gly Met
        35                  40                  45

Ser Ser Gln Gln Cys
    50

<210> SEQ ID NO 24
<211> LENGTH: 586
<212> TYPE: PRT
<213> ORGANISM: Homo sapiens

<400> SEQUENCE: 24

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
```

```
            305                 310                 315                 320
Tyr Glu Ala Trp Leu Gly His Glu Tyr Leu His Ala Met Lys Gly Leu
                325                 330                 335

Leu Cys Asp Pro Asn Arg Leu Pro Tyr Leu Arg Trp Cys Val Leu
                340                 345                 350

Ser Thr Pro Glu Ile Gln Lys Cys Gly Asp Met Ala Val Ala Phe Arg
                355                 360                 365

Arg Gln Arg Leu Lys Pro Glu Ile Gln Cys Val Ser Ala Lys Ser Pro
                370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
                420                 425                 430

Tyr Val Val Ala Val Val Arg Arg Asp Ser Ser His Ala Phe Thr Leu
                435                 440                 445

Asp Glu Leu Arg Gly Lys Arg Ser Cys His Ala Gly Phe Gly Ser Pro
                450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
                500                 505                 510

Cys Ala Leu Cys Val Gly Asp Glu Gln Gly Arg Asn Lys Cys Val Gly
                515                 520                 525

Asn Ser Gln Glu Arg Tyr Tyr Gly Tyr Arg Gly Ala Phe Arg Cys Leu
                530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn
                580                 585

<210> SEQ ID NO 25
<211> LENGTH: 637
<212> TYPE: PRT
<213> ORGANISM: Homo sapiens

<400> SEQUENCE: 25

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
                35                  40                  45

Ala Ala Gln Glu Ala Asp Ala Ile Thr Leu Asp Gly Gly Ala Ile Tyr
                50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95
```

```
Ser Ser His Val Thr Ile Asp Thr Leu Lys Gly Val Lys Ser Cys His
            100                 105                 110
Thr Gly Ile Asn Arg Thr Val Gly Trp Asn Val Pro Val Gly Tyr Leu
        115                 120                 125
Val Glu Ser Gly Arg Leu Ser Val Met Gly Cys Asp Val Leu Lys Ala
    130                 135                 140
Val Ser Asp Tyr Phe Gly Gly Ser Cys Val Pro Gly Ala Gly Glu Thr
145                 150                 155                 160
Ser Tyr Ser Glu Ser Leu Cys Arg Leu Cys Arg Gly Asp Ser Ser Gly
            165                 170                 175
Glu Gly Val Cys Asp Lys Ser Pro Leu Glu Arg Tyr Tyr Asp Tyr Ser
        180                 185                 190
Gly Ala Phe Arg Cys Leu Ala Glu Gly Ala Gly Asp Val Ala Phe Val
    195                 200                 205
Lys His Ser Thr Val Leu Glu Asn Thr Asp Gly Lys Thr Leu Pro Ser
210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
            245                 250                 255
Val Pro Ala His Ala Val Val Arg Ala Asp Thr Asp Gly Gly Leu
        260                 265                 270
Ile Phe Arg Leu Leu Asn Glu Gly Gln Arg Leu Phe Ser His Glu Gly
    275                 280                 285
Ser Ser Phe Gln Met Phe Ser Ser Glu Ala Tyr Gly Gln Lys Asp Leu
290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
            325                 330                 335
Leu Cys Asp Pro Asn Arg Leu Pro Pro Tyr Leu Arg Trp Cys Val Leu
        340                 345                 350
Ser Thr Pro Glu Ile Gln Lys Cys Gly Asp Met Ala Val Ala Phe Arg
    355                 360                 365
Arg Gln Arg Leu Lys Pro Glu Ile Gln Cys Val Ser Ala Lys Ser Pro
370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Thr Tyr Gly Leu Val
            405                 410                 415
Pro Ala Ala Gly Glu His Tyr Ala Pro Glu Asp Ser Ser Asn Ser Tyr
        420                 425                 430
Tyr Val Val Ala Val Val Arg Arg Asp Ser Ser His Ala Phe Thr Leu
    435                 440                 445
Asp Glu Leu Arg Gly Lys Arg Ser Cys His Ala Gly Phe Gly Ser Pro
450                 455                 460
Ala Gly Trp Asp Val Pro Val Gly Ala Leu Ile Gln Arg Gly Phe Ile
465                 470                 475                 480
Arg Pro Lys Asp Cys Asp Val Leu Thr Ala Val Ser Glu Phe Phe Asn
            485                 490                 495
Ala Ser Cys Val Pro Val Asn Asn Pro Lys Asn Tyr Pro Ser Ser Leu
        500                 505                 510
Cys Ala Leu Cys Val Gly Asp Glu Gln Gly Arg Asn Lys Cys Val Gly
```

```
                515                 520                 525
Asn Ser Gln Glu Arg Tyr Tyr Gly Tyr Arg Gly Ala Phe Arg Cys Leu
530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
                580                 585                 590

Ser Gln Phe Ala Ala Cys Asn Leu Ala Gln Ile Pro Pro His Ala Val
                595                 600                 605

Met Val Arg Pro Asp Thr Asn Ile Phe Thr Val Tyr Gly Leu Leu Asp
610                 615                 620

Lys Ala Gln Asp Leu Phe Gly Asp Asp His Asn Lys Asn
625                 630                 635

<210> SEQ ID NO 26
<211> LENGTH: 73
<212> TYPE: PRT
<213> ORGANISM: Homo sapiens

<400> SEQUENCE: 26

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
                20                  25                  30

Ala Cys Asn Leu Ala Gln Ile Pro Pro His Ala Val Met Val Arg Pro
            35                  40                  45

Asp Thr Asn Ile Phe Thr Val Tyr Gly Leu Leu Asp Lys Ala Gln Asp
        50                  55                  60

Leu Phe Gly Asp Asp His Asn Lys Asn
65                  70

<210> SEQ ID NO 27
<211> LENGTH: 126
<212> TYPE: PRT
<213> ORGANISM: Homo sapiens

<400> SEQUENCE: 27

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
                20                  25                  30

Ala Cys Asn Leu Ala Gln Ile Pro Pro His Ala Val Met Val Arg Pro
            35                  40                  45

Asp Thr Asn Ile Phe Thr Val Tyr Gly Leu Leu Asp Lys Ala Gln Asp
        50                  55                  60

Leu Phe Gly Asp Asp His Asn Lys Asn Gly Phe Lys Met Phe Asp Ser
65                  70                  75                  80

Ser Asn Tyr His Gly Gln Asp Leu Leu Phe Lys Asp Ala Thr Val Arg
                85                  90                  95

Ala Val Pro Val Gly Glu Lys Thr Thr Tyr Arg Gly Trp Leu Gly Leu
                100                 105                 110

Asp Tyr Val Ala Ala Leu Glu Gly Met Ser Ser Gln Gln Cys
                115                 120                 125
```

-continued

```
<210> SEQ ID NO 28
<211> LENGTH: 104
<212> TYPE: PRT
<213> ORGANISM: Homo sapiens

<400> SEQUENCE: 28

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn Gly Phe Lys Met Phe Asp Ser Ser Asn Tyr His Gly Gln
    50                  55                  60

Asp Leu Leu Phe Lys Asp Ala Thr Val Arg Ala Val Pro Val Gly Glu
65                  70                  75                  80

Lys Thr Thr Tyr Arg Gly Trp Leu Gly Leu Asp Tyr Val Ala Ala Leu
                85                  90                  95

Glu Gly Met Ser Ser Gln Gln Cys
            100

<210> SEQ ID NO 29
<211> LENGTH: 1272
<212> TYPE: PRT
<213> ORGANISM: Artificial Sequence
<220> FEATURE:
<223> OTHER INFORMATION: p97 fusion protein

<400> SEQUENCE: 29

Met Pro Pro Arg Thr Gly Arg Gly Leu Leu Trp Leu Gly Leu Val
1               5                   10                  15

Leu Ser Ser Val Cys Val Ala Leu Gly His His His His His His
            20                  25                  30

His His His Glu Asn Leu Tyr Phe Gln Ser Glu Thr Gln Ala Asn Ser
        35                  40                  45

Thr Thr Asp Ala Leu Asn Val Leu Leu Ile Ile Val Asp Asp Leu Arg
    50                  55                  60

Pro Ser Leu Gly Cys Tyr Gly Asp Lys Leu Val Arg Ser Pro Asn Ile
65                  70                  75                  80

Asp Gln Leu Ala Ser His Ser Leu Leu Phe Gln Asn Ala Phe Ala Gln
                85                  90                  95

Gln Ala Val Cys Ala Pro Ser Arg Val Ser Phe Leu Thr Gly Arg Arg
            100                 105                 110

Pro Asp Thr Thr Arg Leu Tyr Asp Phe Asn Ser Tyr Trp Arg Val His
        115                 120                 125

Ala Gly Asn Phe Ser Thr Ile Pro Gln Tyr Phe Lys Glu Asn Gly Tyr
    130                 135                 140

Val Thr Met Ser Val Gly Lys Val Phe His Pro Gly Ile Ser Ser Asn
145                 150                 155                 160

His Thr Asp Asp Ser Pro Tyr Ser Trp Ser Phe Pro Pro Tyr His Pro
                165                 170                 175

Ser Ser Glu Lys Tyr Glu Asn Thr Lys Thr Cys Arg Gly Pro Asp Gly
            180                 185                 190

Glu Leu His Ala Asn Leu Leu Cys Pro Val Asp Val Leu Asp Val Pro
        195                 200                 205

Glu Gly Thr Leu Pro Asp Lys Gln Ser Thr Glu Gln Ala Ile Gln Leu
    210                 215                 220
```

```
Leu Glu Lys Met Lys Thr Ser Ala Ser Pro Phe Phe Leu Ala Val Gly
225                 230                 235                 240

Tyr His Lys Pro His Ile Pro Phe Arg Tyr Pro Lys Glu Phe Gln Lys
                245                 250                 255

Leu Tyr Pro Leu Glu Asn Ile Thr Leu Ala Pro Asp Pro Glu Val Pro
            260                 265                 270

Asp Gly Leu Pro Pro Val Ala Tyr Asn Pro Trp Met Asp Ile Arg Gln
        275                 280                 285

Arg Glu Asp Val Gln Ala Leu Asn Ile Ser Val Pro Tyr Gly Pro Ile
    290                 295                 300

Pro Val Asp Phe Gln Arg Lys Ile Arg Gln Ser Tyr Phe Ala Ser Val
305                 310                 315                 320

Ser Tyr Leu Asp Thr Gln Val Gly Arg Leu Leu Ser Ala Leu Asp Asp
                325                 330                 335

Leu Gln Leu Ala Asn Ser Thr Ile Ile Ala Phe Thr Ser Asp His Gly
            340                 345                 350

Trp Ala Leu Gly Glu His Gly Glu Trp Ala Lys Tyr Ser Asn Phe Asp
        355                 360                 365

Val Ala Thr His Val Pro Leu Ile Phe Tyr Val Pro Gly Arg Thr Ala
    370                 375                 380

Ser Leu Pro Glu Ala Gly Glu Lys Leu Phe Pro Tyr Leu Asp Pro Phe
385                 390                 395                 400

Asp Ser Ala Ser Gln Leu Met Glu Pro Gly Arg Gln Ser Met Asp Leu
                405                 410                 415

Val Glu Leu Val Ser Leu Phe Pro Thr Leu Ala Gly Leu Ala Gly Leu
            420                 425                 430

Gln Val Pro Pro Arg Cys Pro Val Pro Ser Phe His Val Glu Leu Cys
        435                 440                 445

Arg Glu Gly Lys Asn Leu Leu Lys His Phe Arg Phe Arg Asp Leu Glu
    450                 455                 460

Glu Asp Pro Tyr Leu Pro Gly Asn Pro Arg Glu Leu Ile Ala Tyr Ser
465                 470                 475                 480

Gln Tyr Pro Arg Pro Ser Asp Ile Pro Gln Trp Asn Ser Asp Lys Pro
                485                 490                 495

Ser Leu Lys Asp Ile Lys Ile Met Gly Tyr Ser Ile Arg Thr Ile Asp
            500                 505                 510

Tyr Arg Tyr Thr Val Trp Val Gly Phe Asn Pro Asp Glu Phe Leu Ala
        515                 520                 525

Asn Phe Ser Asp Ile His Ala Gly Glu Leu Tyr Phe Val Asp Ser Asp
    530                 535                 540

Pro Leu Gln Asp His Asn Met Tyr Asn Asp Ser Gln Gly Gly Asp Leu
545                 550                 555                 560

Phe Gln Leu Leu Met Pro Glu Ala Ala Lys Glu Ala Ala Lys
                565                 570                 575

Glu Ala Ala Ala Lys Gly Met Glu Val Arg Trp Cys Ala Thr Ser Asp
                580                 585                 590

Pro Glu Gln His Lys Cys Gly Asn Met Ser Glu Ala Phe Arg Glu Ala
            595                 600                 605

Gly Ile Gln Pro Ser Leu Leu Cys Val Arg Gly Thr Ser Ala Asp His
        610                 615                 620

Cys Val Gln Leu Ile Ala Ala Gln Glu Ala Asp Ala Ile Thr Leu Asp
625                 630                 635                 640
```

```
Gly Gly Ala Ile Tyr Glu Ala Gly Lys Glu His Gly Leu Lys Pro Val
            645                 650                 655
Val Gly Glu Val Tyr Asp Gln Glu Val Gly Thr Ser Tyr Tyr Ala Val
            660                 665                 670
Ala Val Val Arg Arg Ser Ser His Val Thr Ile Asp Thr Leu Lys Gly
            675                 680                 685
Val Lys Ser Cys His Thr Gly Ile Asn Arg Thr Val Gly Trp Asn Val
            690                 695                 700
Pro Val Gly Tyr Leu Val Glu Ser Gly Arg Leu Ser Val Met Gly Cys
705                 710                 715                 720
Asp Val Leu Lys Ala Val Ser Asp Tyr Phe Gly Gly Ser Cys Val Pro
            725                 730                 735
Gly Ala Gly Glu Thr Ser Tyr Ser Glu Ser Leu Cys Arg Leu Cys Arg
            740                 745                 750
Gly Asp Ser Ser Gly Glu Gly Val Cys Asp Lys Ser Pro Leu Glu Arg
            755                 760                 765
Tyr Tyr Asp Tyr Ser Gly Ala Phe Arg Cys Leu Ala Glu Gly Ala Gly
            770                 775                 780
Asp Val Ala Phe Val Lys His Ser Thr Val Leu Glu Asn Thr Asp Gly
785                 790                 795                 800
Lys Thr Leu Pro Ser Trp Gly Gln Ala Leu Leu Ser Gln Asp Phe Glu
            805                 810                 815
Leu Leu Cys Arg Asp Gly Ser Arg Ala Asp Val Thr Glu Trp Arg Gln
            820                 825                 830
Cys His Leu Ala Arg Val Pro Ala His Ala Val Val Arg Ala Asp
            835                 840                 845
Thr Asp Gly Gly Leu Ile Phe Arg Leu Leu Asn Glu Gly Gln Arg Leu
850                 855                 860
Phe Ser His Glu Gly Ser Ser Phe Gln Met Phe Ser Ser Glu Ala Tyr
865                 870                 875                 880
Gly Gln Lys Asp Leu Leu Phe Lys Asp Ser Thr Ser Glu Leu Val Pro
            885                 890                 895
Ile Ala Thr Gln Thr Tyr Glu Ala Trp Leu Gly His Glu Tyr Leu His
            900                 905                 910
Ala Met Lys Gly Leu Leu Cys Asp Pro Asn Arg Leu Pro Pro Tyr Leu
            915                 920                 925
Arg Trp Cys Val Leu Ser Thr Pro Glu Ile Gln Lys Cys Gly Asp Met
            930                 935                 940
Ala Val Ala Phe Arg Arg Gln Arg Leu Lys Pro Glu Ile Gln Cys Val
945                 950                 955                 960
Ser Ala Lys Ser Pro Gln His Cys Met Glu Arg Ile Gln Ala Glu Gln
            965                 970                 975
Val Asp Ala Val Thr Leu Ser Gly Glu Asp Ile Tyr Thr Ala Gly Lys
            980                 985                 990
Thr Tyr Gly Leu Val Pro Ala Ala Gly Glu His Tyr Ala Pro Glu Asp
            995                 1000                1005
Ser Ser Asn Ser Tyr Tyr Val Ala Val Val Arg Arg Asp Ser
            1010                1015                1020
Ser His Ala Phe Thr Leu Asp Glu Leu Arg Gly Lys Arg Ser Cys
            1025                1030                1035
His Ala Gly Phe Gly Ser Pro Ala Gly Trp Asp Val Pro Val Gly
            1040                1045                1050
Ala Leu Ile Gln Arg Gly Phe Ile Arg Pro Lys Asp Cys Asp Val
```

-continued

```
              1055                1060                1065

Leu Thr Ala Val Ser Glu Phe Phe Asn Ala Ser Cys Val Pro Val
        1070                1075                1080

Asn Asn Pro Lys Asn Tyr Pro Ser Ser Leu Cys Ala Leu Cys Val
        1085                1090                1095

Gly Asp Glu Gln Gly Arg Asn Lys Cys Val Gly Asn Ser Gln Glu
        1100                1105                1110

Arg Tyr Tyr Gly Tyr Arg Gly Ala Phe Arg Cys Leu Val Glu Asn
        1115                1120                1125

Ala Gly Asp Val Ala Phe Val Arg His Thr Thr Val Phe Asp Asn
        1130                1135                1140

Thr Asn Gly His Asn Ser Glu Pro Trp Ala Ala Glu Leu Arg Ser
        1145                1150                1155

Glu Asp Tyr Glu Leu Leu Cys Pro Asn Gly Ala Arg Ala Glu Val
        1160                1165                1170

Ser Gln Phe Ala Ala Cys Asn Leu Ala Gln Ile Pro Pro His Ala
        1175                1180                1185

Val Met Val Arg Pro Asp Thr Asn Ile Phe Thr Val Tyr Gly Leu
        1190                1195                1200

Leu Asp Lys Ala Gln Asp Leu Phe Gly Asp Asp His Asn Lys Asn
        1205                1210                1215

Gly Phe Lys Met Phe Asp Ser Ser Asn Tyr His Gly Gln Asp Leu
        1220                1225                1230

Leu Phe Lys Asp Ala Thr Val Arg Ala Val Pro Val Gly Glu Lys
        1235                1240                1245

Thr Thr Tyr Arg Gly Trp Leu Gly Leu Asp Tyr Val Ala Ala Leu
        1250                1255                1260

Glu Gly Met Ser Ser Gln Gln Cys Ser
        1265                1270

<210> SEQ ID NO 30
<211> LENGTH: 1266
<212> TYPE: PRT
<213> ORGANISM: Artificial Sequence
<220> FEATURE:
<223> OTHER INFORMATION: p97 fusion protein

<400> SEQUENCE: 30

Met Arg Gly Pro Ser Gly Ala Leu Trp Leu Leu Leu Ala Leu Arg Thr
1               5                   10                  15

Val Leu Gly His His His His His His His His Glu Asn Leu
            20                  25                  30

Tyr Phe Gln Gly Met Glu Val Arg Trp Cys Ala Thr Ser Asp Pro Glu
        35                  40                  45

Gln His Lys Cys Gly Asn Met Ser Glu Ala Phe Arg Glu Ala Gly Ile
    50                  55                  60

Gln Pro Ser Leu Leu Cys Val Arg Gly Thr Ser Ala Asp His Cys Val
65                  70                  75                  80

Gln Leu Ile Ala Ala Gln Glu Ala Asp Ala Ile Thr Leu Asp Gly Gly
                85                  90                  95

Ala Ile Tyr Glu Ala Gly Lys Glu His Gly Leu Lys Pro Val Val Gly
            100                 105                 110

Glu Val Tyr Asp Gln Glu Val Gly Thr Ser Tyr Tyr Ala Val Ala Val
        115                 120                 125

Val Arg Arg Ser Ser His Val Thr Ile Asp Thr Leu Lys Gly Val Lys
```

```
            130                 135                 140
Ser Cys His Thr Gly Ile Asn Arg Thr Val Gly Trp Asn Val Pro Val
145                 150                 155                 160

Gly Tyr Leu Val Glu Ser Gly Arg Leu Ser Val Met Gly Cys Asp Val
                165                 170                 175

Leu Lys Ala Val Ser Asp Tyr Phe Gly Gly Ser Cys Val Pro Gly Ala
                180                 185                 190

Gly Glu Thr Ser Tyr Ser Glu Ser Leu Cys Arg Leu Cys Arg Gly Asp
                195                 200                 205

Ser Ser Gly Glu Gly Val Cys Asp Lys Ser Pro Leu Glu Arg Tyr Tyr
210                 215                 220

Asp Tyr Ser Gly Ala Phe Arg Cys Leu Ala Glu Gly Ala Gly Asp Val
225                 230                 235                 240

Ala Phe Val Lys His Ser Thr Val Leu Glu Asn Thr Asp Gly Lys Thr
                245                 250                 255

Leu Pro Ser Trp Gly Gln Ala Leu Leu Ser Gln Asp Phe Glu Leu Leu
                260                 265                 270

Cys Arg Asp Gly Ser Arg Ala Asp Val Thr Glu Trp Arg Gln Cys His
                275                 280                 285

Leu Ala Arg Val Pro Ala His Ala Val Val Val Arg Ala Asp Thr Asp
                290                 295                 300

Gly Gly Leu Ile Phe Arg Leu Leu Asn Glu Gly Gln Arg Leu Phe Ser
305                 310                 315                 320

His Glu Gly Ser Ser Phe Gln Met Phe Ser Ser Glu Ala Tyr Gly Gln
                325                 330                 335

Lys Asp Leu Leu Phe Lys Asp Ser Thr Ser Glu Leu Val Pro Ile Ala
                340                 345                 350

Thr Gln Thr Tyr Glu Ala Trp Leu Gly His Glu Tyr Leu His Ala Met
                355                 360                 365

Lys Gly Leu Leu Cys Asp Pro Asn Arg Leu Pro Pro Tyr Leu Arg Trp
                370                 375                 380

Cys Val Leu Ser Thr Pro Glu Ile Gln Lys Cys Gly Asp Met Ala Val
385                 390                 395                 400

Ala Phe Arg Arg Gln Arg Leu Lys Pro Glu Ile Gln Cys Val Ser Ala
                405                 410                 415

Lys Ser Pro Gln His Cys Met Glu Arg Ile Gln Ala Glu Gln Val Asp
                420                 425                 430

Ala Val Thr Leu Ser Gly Glu Asp Ile Tyr Thr Ala Gly Lys Thr Tyr
                435                 440                 445

Gly Leu Val Pro Ala Ala Gly Glu His Tyr Ala Pro Glu Asp Ser Ser
                450                 455                 460

Asn Ser Tyr Tyr Val Val Ala Val Val Arg Arg Asp Ser Ser His Ala
465                 470                 475                 480

Phe Thr Leu Asp Glu Leu Arg Gly Lys Arg Ser Cys His Ala Gly Phe
                485                 490                 495

Gly Ser Pro Ala Gly Trp Asp Val Pro Val Gly Ala Leu Ile Gln Arg
                500                 505                 510

Gly Phe Ile Arg Pro Lys Asp Cys Asp Val Leu Thr Ala Val Ser Glu
                515                 520                 525

Phe Phe Asn Ala Ser Cys Val Pro Val Asn Asn Pro Lys Asn Tyr Pro
                530                 535                 540

Ser Ser Leu Cys Ala Leu Cys Val Gly Asp Glu Gln Gly Arg Asn Lys
545                 550                 555                 560
```

```
Cys Val Gly Asn Ser Gln Glu Arg Tyr Tyr Gly Tyr Arg Gly Ala Phe
                565                 570                 575

Arg Cys Leu Val Glu Asn Ala Gly Asp Val Ala Phe Val Arg His Thr
                580                 585                 590

Thr Val Phe Asp Asn Thr Asn Gly His Asn Ser Glu Pro Trp Ala Ala
                595                 600                 605

Glu Leu Arg Ser Glu Asp Tyr Glu Leu Leu Cys Pro Asn Gly Ala Arg
                610                 615                 620

Ala Glu Val Ser Gln Phe Ala Ala Cys Asn Leu Ala Gln Ile Pro Pro
625                 630                 635                 640

His Ala Val Met Val Arg Pro Asp Thr Asn Ile Phe Thr Val Tyr Gly
                645                 650                 655

Leu Leu Asp Lys Ala Gln Asp Leu Phe Gly Asp Asp His Asn Lys Asn
                660                 665                 670

Gly Phe Lys Met Phe Asp Ser Ser Asn Tyr His Gly Gln Asp Leu Leu
                675                 680                 685

Phe Lys Asp Ala Thr Val Arg Ala Val Pro Val Gly Glu Lys Thr Thr
690                 695                 700

Tyr Arg Gly Trp Leu Gly Leu Asp Tyr Val Ala Ala Leu Glu Gly Met
705                 710                 715                 720

Ser Ser Gln Gln Cys Ser Glu Ala Ala Ala Lys Glu Ala Ala Ala Lys
                725                 730                 735

Glu Ala Ala Ala Lys Ser Glu Thr Gln Ala Asn Ser Thr Thr Asp Ala
                740                 745                 750

Leu Asn Val Leu Leu Ile Ile Val Asp Asp Leu Arg Pro Ser Leu Gly
                755                 760                 765

Cys Tyr Gly Asp Lys Leu Val Arg Ser Pro Asn Ile Asp Gln Leu Ala
                770                 775                 780

Ser His Ser Leu Leu Phe Gln Asn Ala Phe Ala Gln Ala Val Cys
785                 790                 795                 800

Ala Pro Ser Arg Val Ser Phe Leu Thr Gly Arg Arg Pro Asp Thr Thr
                805                 810                 815

Arg Leu Tyr Asp Phe Asn Ser Tyr Trp Arg Val His Ala Gly Asn Phe
                820                 825                 830

Ser Thr Ile Pro Gln Tyr Phe Lys Glu Asn Gly Tyr Val Thr Met Ser
                835                 840                 845

Val Gly Lys Val Phe His Pro Gly Ile Ser Ser Asn His Thr Asp Asp
850                 855                 860

Ser Pro Tyr Ser Trp Ser Phe Pro Pro Tyr His Pro Ser Ser Glu Lys
865                 870                 875                 880

Tyr Glu Asn Thr Lys Thr Cys Arg Gly Pro Asp Gly Glu Leu His Ala
                885                 890                 895

Asn Leu Leu Cys Pro Val Asp Val Leu Asp Val Pro Glu Gly Thr Leu
                900                 905                 910

Pro Asp Lys Gln Ser Thr Glu Gln Ala Ile Gln Leu Leu Glu Lys Met
                915                 920                 925

Lys Thr Ser Ala Ser Pro Phe Phe Leu Ala Val Gly Tyr His Lys Pro
                930                 935                 940

His Ile Pro Phe Arg Tyr Pro Lys Glu Phe Gln Lys Leu Tyr Pro Leu
945                 950                 955                 960

Glu Asn Ile Thr Leu Ala Pro Asp Pro Glu Val Pro Asp Gly Leu Pro
                965                 970                 975
```

Pro Val Ala Tyr Asn Pro Trp Met Asp Ile Arg Gln Arg Glu Asp Val
                980                 985                 990

Gln Ala Leu Asn Ile Ser Val Pro Tyr Gly Pro Ile Pro Val Asp Phe
        995                 1000                1005

Gln Arg Lys Ile Arg Gln Ser Tyr Phe Ala Ser Val Ser Tyr Leu
    1010                1015                1020

Asp Thr Gln Val Gly Arg Leu Leu Ser Ala Leu Asp Asp Leu Gln
    1025                1030                1035

Leu Ala Asn Ser Thr Ile Ile Ala Phe Thr Ser Asp His Gly Trp
    1040                1045                1050

Ala Leu Gly Glu His Gly Glu Trp Ala Lys Tyr Ser Asn Phe Asp
    1055                1060                1065

Val Ala Thr His Val Pro Leu Ile Phe Tyr Val Pro Gly Arg Thr
    1070                1075                1080

Ala Ser Leu Pro Glu Ala Gly Glu Lys Leu Phe Pro Tyr Leu Asp
    1085                1090                1095

Pro Phe Asp Ser Ala Ser Gln Leu Met Glu Pro Gly Arg Gln Ser
    1100                1105                1110

Met Asp Leu Val Glu Leu Val Ser Leu Phe Pro Thr Leu Ala Gly
    1115                1120                1125

Leu Ala Gly Leu Gln Val Pro Pro Arg Cys Pro Val Pro Ser Phe
    1130                1135                1140

His Val Glu Leu Cys Arg Glu Gly Lys Asn Leu Leu Lys His Phe
    1145                1150                1155

Arg Phe Arg Asp Leu Glu Glu Asp Pro Tyr Leu Pro Gly Asn Pro
    1160                1165                1170

Arg Glu Leu Ile Ala Tyr Ser Gln Tyr Pro Arg Pro Ser Asp Ile
    1175                1180                1185

Pro Gln Trp Asn Ser Asp Lys Pro Ser Leu Lys Asp Ile Lys Ile
    1190                1195                1200

Met Gly Tyr Ser Ile Arg Thr Ile Asp Tyr Arg Tyr Thr Val Trp
    1205                1210                1215

Val Gly Phe Asn Pro Asp Glu Phe Leu Ala Asn Phe Ser Asp Ile
    1220                1225                1230

His Ala Gly Glu Leu Tyr Phe Val Asp Ser Asp Pro Leu Gln Asp
    1235                1240                1245

His Asn Met Tyr Asn Asp Ser Gln Gly Gly Asp Leu Phe Gln Leu
    1250                1255                1260

Leu Met Pro
    1265

<210> SEQ ID NO 31
<211> LENGTH: 550
<212> TYPE: PRT
<213> ORGANISM: Homo sapiens

<400> SEQUENCE: 31

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

```
Asp Gln Leu Ala Ser His Ser Leu Leu Phe Gln Asn Ala Phe Ala Gln
 65                  70                  75                  80

Gln Ala Val Cys Ala Pro Ser Arg Val Ser Phe Leu Thr Gly Arg Arg
             85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480
```

```
Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
    530                 535                 540

Phe Gln Leu Leu Met Pro
545             550

<210> SEQ ID NO 32
<211> LENGTH: 525
<212> TYPE: PRT
<213> ORGANISM: Homo sapiens

<400> SEQUENCE: 32

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
    195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300
```

```
Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
        340                 345                 350

Phe Pro Tyr Leu Asp Pro Phe Asp Ser Ala Ser Gln Leu Met Glu Pro
    355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro
            515                 520                 525

<210> SEQ ID NO 33
<211> LENGTH: 517
<212> TYPE: PRT
<213> ORGANISM: Homo sapiens

<400> SEQUENCE: 33

Thr Asp Ala Leu Asn Val Leu Leu Ile Ile Val Asp Asp Leu Arg Pro
1               5                   10                  15

Ser Leu Gly Cys Tyr Gly Asp Lys Leu Val Arg Ser Pro Asn Ile Asp
            20                  25                  30

Gln Leu Ala Ser His Ser Leu Leu Phe Gln Asn Ala Phe Ala Gln Gln
        35                  40                  45

Ala Val Cys Ala Pro Ser Arg Val Ser Phe Leu Thr Gly Arg Arg Pro
    50                  55                  60

Asp Thr Thr Arg Leu Tyr Asp Phe Asn Ser Tyr Trp Arg Val His Ala
65                  70                  75                  80

Gly Asn Phe Ser Thr Ile Pro Gln Tyr Phe Lys Glu Asn Gly Tyr Val
                85                  90                  95

Thr Met Ser Val Gly Lys Val Phe His Pro Gly Ile Ser Ser Asn His
            100                 105                 110

Thr Asp Asp Ser Pro Tyr Ser Trp Ser Phe Pro Pro Tyr His Pro Ser
        115                 120                 125

Ser Glu Lys Tyr Glu Asn Thr Lys Thr Cys Arg Gly Pro Asp Gly Glu
    130                 135                 140

Leu His Ala Asn Leu Leu Cys Pro Val Asp Val Leu Asp Val Pro Glu
```

```
            145                 150                 155                 160

Gly Thr Leu Pro Asp Lys Gln Ser Thr Glu Gln Ala Ile Gln Leu Leu
                165                 170                 175

Glu Lys Met Lys Thr Ser Ala Ser Pro Phe Leu Ala Val Gly Tyr
            180                 185                 190

His Lys Pro His Ile Pro Phe Arg Tyr Pro Lys Glu Phe Gln Lys Leu
                195                 200                 205

Tyr Pro Leu Glu Asn Ile Thr Leu Ala Pro Asp Pro Glu Val Pro Asp
            210                 215                 220

Gly Leu Pro Pro Val Ala Tyr Asn Pro Trp Met Asp Ile Arg Gln Arg
225                 230                 235                 240

Glu Asp Val Gln Ala Leu Asn Ile Ser Val Pro Tyr Gly Pro Ile Pro
                245                 250                 255

Val Asp Phe Gln Arg Lys Ile Arg Gln Ser Tyr Phe Ala Ser Val Ser
            260                 265                 270

Tyr Leu Asp Thr Gln Val Gly Arg Leu Leu Ser Ala Leu Asp Asp Leu
                275                 280                 285

Gln Leu Ala Asn Ser Thr Ile Ile Ala Phe Thr Ser Asp His Gly Trp
            290                 295                 300

Ala Leu Gly Glu His Gly Glu Trp Ala Lys Tyr Ser Asn Phe Asp Val
305                 310                 315                 320

Ala Thr His Val Pro Leu Ile Phe Tyr Val Pro Gly Arg Thr Ala Ser
                325                 330                 335

Leu Pro Glu Ala Gly Glu Lys Leu Phe Pro Tyr Leu Asp Pro Phe Asp
            340                 345                 350

Ser Ala Ser Gln Leu Met Glu Pro Gly Arg Gln Ser Met Asp Leu Val
            355                 360                 365

Glu Leu Val Ser Leu Phe Pro Thr Leu Ala Gly Leu Ala Gly Leu Gln
            370                 375                 380

Val Pro Pro Arg Cys Pro Val Pro Ser Phe His Val Glu Leu Cys Arg
385                 390                 395                 400

Glu Gly Lys Asn Leu Leu Lys His Phe Arg Phe Arg Asp Leu Glu Glu
                405                 410                 415

Asp Pro Tyr Leu Pro Gly Asn Pro Arg Glu Leu Ile Ala Tyr Ser Gln
            420                 425                 430

Tyr Pro Arg Pro Ser Asp Ile Pro Gln Trp Asn Ser Asp Lys Pro Ser
            435                 440                 445

Leu Lys Asp Ile Lys Ile Met Gly Tyr Ser Ile Arg Thr Ile Asp Tyr
            450                 455                 460

Arg Tyr Thr Val Trp Val Gly Phe Asn Pro Asp Glu Phe Leu Ala Asn
465                 470                 475                 480

Phe Ser Asp Ile His Ala Gly Glu Leu Tyr Phe Val Asp Ser Asp Pro
                485                 490                 495

Leu Gln Asp His Asn Met Tyr Asn Asp Ser Gln Gly Gly Asp Leu Phe
                500                 505                 510

Gln Leu Leu Met Pro
            515

<210> SEQ ID NO 34
<211> LENGTH: 422
<212> TYPE: PRT
<213> ORGANISM: Homo sapiens

<400> SEQUENCE: 34
```

```
Thr Asp Ala Leu Asn Val Leu Leu Ile Ile Val Asp Asp Leu Arg Pro
1               5                   10                  15

Ser Leu Gly Cys Tyr Gly Asp Lys Leu Val Arg Ser Pro Asn Ile Asp
            20                  25                  30

Gln Leu Ala Ser His Ser Leu Leu Phe Gln Asn Ala Phe Ala Gln Gln
            35                  40                  45

Ala Val Cys Ala Pro Ser Arg Val Ser Phe Leu Thr Gly Arg Arg Pro
50                  55                  60

Asp Thr Thr Arg Leu Tyr Asp Phe Asn Ser Tyr Trp Arg Val His Ala
65                  70                  75                  80

Gly Asn Phe Ser Thr Ile Pro Gln Tyr Phe Lys Glu Asn Gly Tyr Val
            85                  90                  95

Thr Met Ser Val Gly Lys Val Phe His Pro Gly Ile Ser Ser Asn His
            100                 105                 110

Thr Asp Asp Ser Pro Tyr Ser Trp Ser Phe Pro Pro Tyr His Pro Ser
            115                 120                 125

Ser Glu Lys Tyr Glu Asn Thr Lys Thr Cys Arg Gly Pro Asp Gly Glu
            130                 135                 140

Leu His Ala Asn Leu Leu Cys Pro Val Asp Val Leu Asp Val Pro Glu
145                 150                 155                 160

Gly Thr Leu Pro Asp Lys Gln Ser Thr Glu Gln Ala Ile Gln Leu Leu
                165                 170                 175

Glu Lys Met Lys Thr Ser Ala Ser Pro Phe Phe Leu Ala Val Gly Tyr
            180                 185                 190

His Lys Pro His Ile Pro Phe Arg Tyr Pro Lys Glu Phe Gln Lys Leu
            195                 200                 205

Tyr Pro Leu Glu Asn Ile Thr Leu Ala Pro Asp Pro Glu Val Pro Asp
210                 215                 220

Gly Leu Pro Pro Val Ala Tyr Asn Pro Trp Met Asp Ile Arg Gln Arg
225                 230                 235                 240

Glu Asp Val Gln Ala Leu Asn Ile Ser Val Pro Tyr Gly Pro Ile Pro
            245                 250                 255

Val Asp Phe Gln Arg Lys Ile Arg Gln Ser Tyr Phe Ala Ser Val Ser
            260                 265                 270

Tyr Leu Asp Thr Gln Val Gly Arg Leu Leu Ser Ala Leu Asp Asp Leu
            275                 280                 285

Gln Leu Ala Asn Ser Thr Ile Ile Ala Phe Thr Ser Asp His Gly Trp
            290                 295                 300

Ala Leu Gly Glu His Gly Glu Trp Ala Lys Tyr Ser Asn Phe Asp Val
305                 310                 315                 320

Ala Thr His Val Pro Leu Ile Phe Tyr Val Pro Gly Arg Thr Ala Ser
                325                 330                 335

Leu Pro Glu Ala Gly Glu Lys Leu Phe Pro Tyr Leu Asp Pro Phe Asp
            340                 345                 350

Ser Ala Ser Gln Leu Met Glu Pro Gly Arg Gln Ser Met Asp Leu Val
            355                 360                 365

Glu Leu Val Ser Leu Phe Pro Thr Leu Ala Gly Leu Ala Gly Leu Gln
            370                 375                 380

Val Pro Pro Arg Cys Pro Val Pro Ser Phe His Val Glu Leu Cys Arg
385                 390                 395                 400

Glu Gly Lys Asn Leu Leu Lys His Phe Arg Phe Arg Asp Leu Glu Glu
                405                 410                 415

Asp Pro Tyr Leu Pro Gly
```

-continued

```
                420

<210> SEQ ID NO 35
<211> LENGTH: 95
<212> TYPE: PRT
<213> ORGANISM: Homo sapiens

<400> SEQUENCE: 35

Asn Pro Arg Glu Leu Ile Ala Tyr Ser Gln Tyr Pro Arg Pro Ser Asp
1               5                   10                  15

Ile Pro Gln Trp Asn Ser Asp Lys Pro Ser Leu Lys Asp Ile Lys Ile
            20                  25                  30

Met Gly Tyr Ser Ile Arg Thr Ile Asp Tyr Arg Tyr Thr Val Trp Val
        35                  40                  45

Gly Phe Asn Pro Asp Glu Phe Leu Ala Asn Phe Ser Asp Ile His Ala
    50                  55                  60

Gly Glu Leu Tyr Phe Val Asp Ser Asp Pro Leu Gln Asp His Asn Met
65                  70                  75                  80

Tyr Asn Asp Ser Gln Gly Gly Asp Leu Phe Gln Leu Leu Met Pro
                85                  90                  95

<210> SEQ ID NO 36
<211> LENGTH: 5
<212> TYPE: PRT
<213> ORGANISM: Artificial Sequence
<220> FEATURE:
<223> OTHER INFORMATION: rigid peptide linker

<400> SEQUENCE: 36

Glu Ala Ala Ala Lys
1               5

<210> SEQ ID NO 37
<211> LENGTH: 10
<212> TYPE: PRT
<213> ORGANISM: Artificial Sequence
<220> FEATURE:
<223> OTHER INFORMATION: rigid peptide linker

<400> SEQUENCE: 37

Glu Ala Ala Ala Lys Glu Ala Ala Ala Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: rigid peptide linker

<400> SEQUENCE: 38

Glu Ala Ala Ala Lys Glu Ala Ala Ala Lys Glu Ala Ala Ala Lys
1               5                   10                  15

<210> SEQ ID NO 39
<211> LENGTH: 19
<212> TYPE: PRT
<213> ORGANISM: Homo sapiens

<400> SEQUENCE: 39

Met Arg Gly Pro Ser Gly Ala Leu Trp Leu Leu Leu Ala Leu Arg Thr
1               5                   10                  15

Val Leu Gly
```

```
<210> SEQ ID NO 40
<211> LENGTH: 25
<212> TYPE: PRT
<213> ORGANISM: Homo sapiens

<400> SEQUENCE: 40

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 41
<211> LENGTH: 16
<212> TYPE: PRT
<213> ORGANISM: Artificial Sequence
<220> FEATURE:
<223> OTHER INFORMATION: rigid peptide linker

<400> SEQUENCE: 41

Ala Glu Ala Ala Ala Lys Ala Leu Glu Ala Glu Ala Ala Ala Lys Ala
1               5                   10                  15

<210> SEQ ID NO 42
<211> LENGTH: 46
<212> TYPE: PRT
<213> ORGANISM: Artificial Sequence
<220> FEATURE:
<223> OTHER INFORMATION: rigid peptide linker

<400> SEQUENCE: 42

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
            35                  40                  45

<210> SEQ ID NO 43
<211> LENGTH: 5
<212> TYPE: PRT
<213> ORGANISM: Artificial Sequence
<220> FEATURE:
<223> OTHER INFORMATION: rigid peptide linker

<400> SEQUENCE: 43

Pro Ala Pro Ala Pro
1               5

<210> SEQ ID NO 44
<211> LENGTH: 12
<212> TYPE: PRT
<213> ORGANISM: Artificial Sequence
<220> FEATURE:
<223> OTHER INFORMATION: rigid peptide linker

<400> SEQUENCE: 44

Ala Glu Ala Ala Ala Lys Glu Ala Ala Ala Lys Ala
1               5                   10

<210> SEQ ID NO 45
<211> LENGTH: 5
<212> TYPE: PRT
<213> ORGANISM: Artificial Sequence
<220> FEATURE:
```

<223> OTHER INFORMATION: flexible peptide linker

<400> SEQUENCE: 45

Gly Gly Gly Gly Ser
1               5

<210> SEQ ID NO 46
<211> LENGTH: 10
<212> TYPE: PRT
<213> ORGANISM: Artificial Sequence
<220> FEATURE:
<223> OTHER INFORMATION: flexible peptide linker

<400> SEQUENCE: 46

Gly Gly Gly Gly Ser Gly Gly Gly Gly Ser
1               5                   10

<210> SEQ ID NO 47
<211> LENGTH: 15
<212> TYPE: PRT
<213> ORGANISM: Artificial Sequence
<220> FEATURE:
<223> OTHER INFORMATION: flexible peptide linker

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 4
<212> TYPE: PRT
<213> ORGANISM: Artificial Sequence
<220> FEATURE:
<223> OTHER INFORMATION: flexible peptide linker

<400> SEQUENCE: 48

Gly Gly Gly Gly
1

<210> SEQ ID NO 49
<211> LENGTH: 5
<212> TYPE: PRT
<213> ORGANISM: Artificial Sequence
<220> FEATURE:
<223> OTHER INFORMATION: flexible peptide linker

<400> SEQUENCE: 49

Gly Gly Gly Gly Gly
1               5

<210> SEQ ID NO 50
<211> LENGTH: 6
<212> TYPE: PRT
<213> ORGANISM: Artificial Sequence
<220> FEATURE:
<223> OTHER INFORMATION: flexible peptide linker

<400> SEQUENCE: 50

Gly Gly Gly Gly Gly Gly
1               5

<210> SEQ ID NO 51
<211> LENGTH: 7
<212> TYPE: PRT
<213> ORGANISM: Artificial Sequence
<220> FEATURE:
<223> OTHER INFORMATION: flexible peptide linker

```
<400> SEQUENCE: 51

Gly Gly Gly Gly Gly Gly Gly
1               5

<210> SEQ ID NO 52
<211> LENGTH: 8
<212> TYPE: PRT
<213> ORGANISM: Artificial Sequence
<220> FEATURE:
<223> OTHER INFORMATION: flexible peptide linker

<400> SEQUENCE: 52

Gly Gly Gly Gly Gly Gly Gly Gly
1               5

<210> SEQ ID NO 53
<211> LENGTH: 9
<212> TYPE: PRT
<213> ORGANISM: Artificial Sequence
<220> FEATURE:
<223> OTHER INFORMATION: flexible peptide linker

<400> SEQUENCE: 53

Gly Gly Gly Gly Gly Gly Gly Gly Gly
1               5

<210> SEQ ID NO 54
<211> LENGTH: 10
<212> TYPE: PRT
<213> ORGANISM: Artificial Sequence
<220> FEATURE:
<223> OTHER INFORMATION: flexible peptide linker

<400> SEQUENCE: 54

Gly Gly Gly Gly Gly Gly Gly Gly Gly Gly
1               5                   10

<210> SEQ ID NO 55
<211> LENGTH: 4
<212> TYPE: PRT
<213> ORGANISM: Artificial Sequence
<220> FEATURE:
<223> OTHER INFORMATION: Peptide linker

<400> SEQUENCE: 55

Gly Ser Gly Ser
1

<210> SEQ ID NO 56
<211> LENGTH: 4
<212> TYPE: PRT
<213> ORGANISM: Artificial Sequence
<220> FEATURE:
<223> OTHER INFORMATION: Peptide linker

<400> SEQUENCE: 56

Gly Gly Ser Gly
1

<210> SEQ ID NO 57
<211> LENGTH: 4
<212> TYPE: PRT
<213> ORGANISM: Artificial Sequence
<220> FEATURE:
<223> OTHER INFORMATION: Peptide linker
```

```
<400> SEQUENCE: 57

Gly Gly Gly Ser
1

<210> SEQ ID NO 58
<211> LENGTH: 4
<212> TYPE: PRT
<213> ORGANISM: Artificial Sequence
<220> FEATURE:
<223> OTHER INFORMATION: Peptide linker

<400> SEQUENCE: 58

Gly Asn Gly Asn
1

<210> SEQ ID NO 59
<211> LENGTH: 4
<212> TYPE: PRT
<213> ORGANISM: Artificial Sequence
<220> FEATURE:
<223> OTHER INFORMATION: Peptide linker

<400> SEQUENCE: 59

Gly Gly Asn Gly
1

<210> SEQ ID NO 60
<211> LENGTH: 4
<212> TYPE: PRT
<213> ORGANISM: Artificial Sequence
<220> FEATURE:
<223> OTHER INFORMATION: Peptide linker

<400> SEQUENCE: 60

Gly Gly Gly Asn
1

<210> SEQ ID NO 61
<211> LENGTH: 5
<212> TYPE: PRT
<213> ORGANISM: Artificial Sequence
<220> FEATURE:
<223> OTHER INFORMATION: Peptide linker

<400> SEQUENCE: 61

Gly Gly Gly Gly Asn
1               5

<210> SEQ ID NO 62
<211> LENGTH: 17
<212> TYPE: PRT
<213> ORGANISM: Artificial Sequence
<220> FEATURE:
<223> OTHER INFORMATION: Factor XIa/FVIIa cleavable linker

<400> SEQUENCE: 62

Val Ser Gln Thr Ser Lys Leu Thr Arg Ala Glu Thr Val Phe Pro Asp
1               5                   10                  15

Val

<210> SEQ ID NO 63
<211> LENGTH: 6
<212> TYPE: PRT
<213> ORGANISM: Artificial Sequence
<220> FEATURE:
<223> OTHER INFORMATION: Mtrix metalloprotease-1 cleavable linker
```

```
<400> SEQUENCE: 63

Pro Leu Gly Leu Trp Ala
1               5

<210> SEQ ID NO 64
<211> LENGTH: 6
<212> TYPE: PRT
<213> ORGANISM: Artificial Sequence
<220> FEATURE:
<223> OTHER INFORMATION: HIV protease cleavable linker

<400> SEQUENCE: 64

Arg Val Leu Ala Glu Ala
1               5

<210> SEQ ID NO 65
<211> LENGTH: 10
<212> TYPE: PRT
<213> ORGANISM: Artificial Sequence
<220> FEATURE:
<223> OTHER INFORMATION: Hepatitis C virus NS3 protease cleavable linker

<400> SEQUENCE: 65

Glu Asp Val Val Cys Cys Ser Met Ser Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Factor Xa cleavable linker

<400> SEQUENCE: 66

Gly Gly Ile Glu Gly Arg Gly Ser
1               5

<210> SEQ ID NO 67
<211> LENGTH: 10
<212> TYPE: PRT
<213> ORGANISM: Artificial Sequence
<220> FEATURE:
<223> OTHER INFORMATION: Furin cleavable linker

<400> SEQUENCE: 67

Thr Arg His Arg Gln Pro Arg Gly Trp Glu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Furin cleavable linker

<400> SEQUENCE: 68

Ala Gly Asn Arg Val Arg Arg Ser Val Gly
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Furin cleavable linker
```

```
<400> SEQUENCE: 69

Arg Arg Arg Arg Arg Arg Arg Arg
1               5

<210> SEQ ID NO 70
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 70

Gly Phe Leu Gly
1

<210> SEQ ID NO 71
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 71

Gly Arg Gly Asp
1

<210> SEQ ID NO 72
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 72

Gly Arg Gly Asp Asn Pro
1               5

<210> SEQ ID NO 73
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 73

Gly Arg Gly Asp Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 74

Gly Arg Gly Asp Ser Pro Lys
1               5

<210> SEQ ID NO 75
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 75
```

```
Ala Ala Pro Val
1

<210> SEQ ID NO 76
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 76

Ala Ala Pro Leu
1

<210> SEQ ID NO 77
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 77

Ala Ala Pro Phe
1

<210> SEQ ID NO 78
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 78

Ala Ala Pro Ala
1

<210> SEQ ID NO 79
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 79

Ala Tyr Leu Val
1

<210> SEQ ID NO 80
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 80

Gly Pro Xaa Gly Pro Xaa
1               5

<210> SEQ ID NO 81
```

```
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid

<400> SEQUENCE: 81

Leu Gly Pro Xaa
1

<210> SEQ ID NO 82
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 82

Gly Pro Ile Gly Pro Xaa
1               5

<210> SEQ ID NO 83
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 83

Ala Pro Gly Leu Xaa
1               5

<210> SEQ ID NO 84
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 84

Pro Leu Gly Pro Asp Arg Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 85
```

```
Pro Leu Gly Leu Leu Gly Xaa
1               5
```

<210> SEQ ID NO 86
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 86

```
Pro Gln Gly Ile Ala Gly Trp
1               5
```

<210> SEQ ID NO 87
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 87

```
Pro Leu Gly Cys His
1               5
```

<210> SEQ ID NO 88
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 88

```
Pro Leu Gly Leu Tyr Ala
1               5
```

<210> SEQ ID NO 89
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 89

```
Pro Leu Ala Leu Trp Ala Arg
1               5
```

<210> SEQ ID NO 90
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 90

```
Pro Leu Ala Tyr Trp Ala Arg
1               5
```

<210> SEQ ID NO 91
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 91

Pro Tyr Ala Tyr Tyr Met Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Gelatinase cleavable linker

<400> SEQUENCE: 92

Pro Leu Gly Met Tyr Ser Arg
1               5

<210> SEQ ID NO 93
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 93

Gly Asp Lys Pro
1

<210> SEQ ID NO 94
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 94

Gly Ser Asp Lys Pro
1               5

<210> SEQ ID NO 95
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 95

Ala Leu Ala Leu
1

<210> SEQ ID NO 96
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 96

Gly Phe Leu Gly
1

<210> SEQ ID NO 97
<211> LENGTH: 22
<212> TYPE: PRT
<213> ORGANISM: Homo sapiens

<400> SEQUENCE: 97

Met Asp Met Arg Ala Pro Ala Gly Ile Phe Gly Phe Leu Leu Val Leu
1               5                   10                  15

```
Phe Pro Gly Tyr Arg Ser
        20

<210> SEQ ID NO 98
<211> LENGTH: 18
<212> TYPE: PRT
<213> ORGANISM: Homo sapiens

<400> SEQUENCE: 98

Met Lys Trp Val Thr Phe Ile Ser Leu Leu Phe Leu Phe Ser Ser Ala
1               5                   10                  15

Tyr Ser

<210> SEQ ID NO 99
<211> LENGTH: 19
<212> TYPE: PRT
<213> ORGANISM: Homo sapiens

<400> SEQUENCE: 99

Met Asp Trp Thr Trp Arg Val Phe Cys Leu Leu Ala Val Thr Pro Gly
1               5                   10                  15

Ala His Pro

<210> SEQ ID NO 100
<211> LENGTH: 19
<212> TYPE: PRT
<213> ORGANISM: Homo sapiens

<400> SEQUENCE: 100

Met Ala Trp Ser Pro Leu Phe Leu Thr Leu Ile Thr His Cys Ala Gly
1               5                   10                  15

Ser Trp Ala

<210> SEQ ID NO 101
<211> LENGTH: 19
<212> TYPE: PRT
<213> ORGANISM: Homo sapiens

<400> SEQUENCE: 101

Met Thr Arg Leu Thr Val Leu Ala Leu Leu Ala Gly Leu Leu Ala Ser
1               5                   10                  15

Ser Arg Ala

<210> SEQ ID NO 102
<211> LENGTH: 20
<212> TYPE: PRT
<213> ORGANISM: Homo sapiens

<400> SEQUENCE: 102

Met Ala Arg Pro Leu Cys Thr Leu Leu Leu Leu Met Ala Thr Leu Ala
1               5                   10                  15

Gly Ala Leu Ala
        20

<210> SEQ ID NO 103
<211> LENGTH: 15
<212> TYPE: PRT
<213> ORGANISM: Homo sapiens

<400> SEQUENCE: 103

Met Arg Ser Leu Val Phe Val Leu Leu Ile Gly Ala Ala Phe Ala
1               5                   10                  15
```

<210> SEQ ID NO 104
<211> LENGTH: 22
<212> TYPE: PRT
<213> ORGANISM: Homo sapiens

<400> SEQUENCE: 104

Met Ser Arg Leu Phe Val Phe Ile Leu Ile Ala Leu Phe Leu Ser Ala
1               5                   10                  15

Ile Ile Asp Val Met Ser
            20

<210> SEQ ID NO 105
<211> LENGTH: 21
<212> TYPE: PRT
<213> ORGANISM: Homo sapiens

<400> SEQUENCE: 105

Met Gly Met Arg Met Met Phe Ile Met Phe Met Leu Val Val Leu Ala
1               5                   10                  15

Thr Thr Val Val Ser
            20

<210> SEQ ID NO 106
<211> LENGTH: 18
<212> TYPE: PRT
<213> ORGANISM: Homo sapiens

<400> SEQUENCE: 106

Met Arg Ala Phe Leu Phe Leu Thr Ala Cys Ile Ser Leu Pro Gly Val
1               5                   10                  15

Phe Gly

<210> SEQ ID NO 107
<211> LENGTH: 18
<212> TYPE: PRT
<213> ORGANISM: Homo sapiens

<400> SEQUENCE: 107

Met Lys Phe Gln Ser Thr Leu Leu Leu Ala Ala Ala Gly Ser Ala
1               5                   10                  15

Leu Ala

<210> SEQ ID NO 108
<211> LENGTH: 24
<212> TYPE: PRT
<213> ORGANISM: Homo sapiens

<400> SEQUENCE: 108

Met Ala Ser Ser Leu Tyr Ser Phe Leu Leu Ala Leu Ser Ile Val Tyr
1               5                   10                  15

Ile Phe Val Ala Pro Thr His Ser
            20

<210> SEQ ID NO 109
<211> LENGTH: 26
<212> TYPE: PRT
<213> ORGANISM: Homo sapiens

<400> SEQUENCE: 109

Met Lys Thr His Tyr Ser Ser Ala Ile Leu Pro Ile Leu Thr Leu Phe
1               5                   10                  15

```
Val Phe Leu Ser Ile Asn Pro Ser His Gly
            20                  25

<210> SEQ ID NO 110
<211> LENGTH: 36
<212> TYPE: PRT
<213> ORGANISM: Homo sapiens

<400> SEQUENCE: 110

Met Glu Ser Val Ser Ser Leu Phe Asn Ile Phe Ser Thr Ile Met Val
1               5                   10                  15

Asn Tyr Lys Ser Leu Val Leu Ala Leu Leu Ser Val Ser Asn Leu Lys
            20                  25                  30

Tyr Ala Arg Gly
        35

<210> SEQ ID NO 111
<211> LENGTH: 21
<212> TYPE: PRT
<213> ORGANISM: Homo sapiens

<400> SEQUENCE: 111

Met Lys Ala Ala Gln Ile Leu Thr Ala Ser Ile Val Ser Leu Leu Pro
1               5                   10                  15

Ile Tyr Thr Ser Ala
            20

<210> SEQ ID NO 112
<211> LENGTH: 19
<212> TYPE: PRT
<213> ORGANISM: Homo sapiens

<400> SEQUENCE: 112

Met Ile Lys Leu Lys Phe Gly Val Phe Phe Thr Val Leu Leu Ser Ser
1               5                   10                  15

Ala Tyr Ala

<210> SEQ ID NO 113
<211> LENGTH: 5
<212> TYPE: PRT
<213> ORGANISM: Artificial Sequence
<220> FEATURE:
<223> OTHER INFORMATION: Purification tag

<400> SEQUENCE: 113

His His His His His
1               5

<210> SEQ ID NO 114
<211> LENGTH: 6
<212> TYPE: PRT
<213> ORGANISM: Artificial Sequence
<220> FEATURE:
<223> OTHER INFORMATION: Purification tag

<400> SEQUENCE: 114

His His His His His His
1               5

<210> SEQ ID NO 115
<211> LENGTH: 7
<212> TYPE: PRT
<213> ORGANISM: Artificial Sequence
```

```
<220> FEATURE:
<223> OTHER INFORMATION: Purification tag

<400> SEQUENCE: 115

His His His His His His His
1               5

<210> SEQ ID NO 116
<211> LENGTH: 8
<212> TYPE: PRT
<213> ORGANISM: Artificial Sequence
<220> FEATURE:
<223> OTHER INFORMATION: Purification tag

<400> SEQUENCE: 116

His His His His His His His His
1               5

<210> SEQ ID NO 117
<211> LENGTH: 9
<212> TYPE: PRT
<213> ORGANISM: Artificial Sequence
<220> FEATURE:
<223> OTHER INFORMATION: Purification tag

<400> SEQUENCE: 117

His His His His His His His His His
1               5

<210> SEQ ID NO 118
<211> LENGTH: 10
<212> TYPE: PRT
<213> ORGANISM: Artificial Sequence
<220> FEATURE:
<223> OTHER INFORMATION: Purification tag

<400> SEQUENCE: 118

His His His His His His His His His His
1               5                   10

<210> SEQ ID NO 119
<211> LENGTH: 15
<212> TYPE: PRT
<213> ORGANISM: Artificial Sequence
<220> FEATURE:
<223> OTHER INFORMATION: Purification tag - AviTag

<400> SEQUENCE: 119

Gly Leu Asn Asp Ile Phe Glu Ala Gln Lys Ile Glu Trp His Glu
1               5                   10                  15

<210> SEQ ID NO 120
<211> LENGTH: 26
<212> TYPE: PRT
<213> ORGANISM: Artificial Sequence
<220> FEATURE:
<223> OTHER INFORMATION: Purification tag - Calmodulin-tag

<400> SEQUENCE: 120

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 121
<211> LENGTH: 6
```

```
<212> TYPE: PRT
<213> ORGANISM: Artificial Sequence
<220> FEATURE:
<223> OTHER INFORMATION: Purification tag - Polyglutamate tag

<400> SEQUENCE: 121

Glu Glu Glu Glu Glu Glu
1               5

<210> SEQ ID NO 122
<211> LENGTH: 8
<212> TYPE: PRT
<213> ORGANISM: Artificial Sequence
<220> FEATURE:
<223> OTHER INFORMATION: Purification tag - FLAG-tag

<400> SEQUENCE: 122

Asp Tyr Lys Asp Asp Asp Asp Lys
1               5

<210> SEQ ID NO 123
<211> LENGTH: 9
<212> TYPE: PRT
<213> ORGANISM: Artificial Sequence
<220> FEATURE:
<223> OTHER INFORMATION: Purificiation tag - HA-tag

<400> SEQUENCE: 123

Tyr Pro Tyr Asp Val Pro Asp Tyr Ala
1               5

<210> SEQ ID NO 124
<211> LENGTH: 10
<212> TYPE: PRT
<213> ORGANISM: Artificial Sequence
<220> FEATURE:
<223> OTHER INFORMATION: Purification tag - MYC-tag

<400> SEQUENCE: 124

Glu Gln Lys Leu Ile Ser Glu Glu Asp Leu
1               5                   10

<210> SEQ ID NO 125
<211> LENGTH: 15
<212> TYPE: PRT
<213> ORGANISM: Artificial Sequence
<220> FEATURE:
<223> OTHER INFORMATION: Purification tag - S-tag

<400> SEQUENCE: 125

Lys Glu Thr Ala Ala Ala Lys Phe Glu Arg Gln His Met Asp Ser
1               5                   10                  15

<210> SEQ ID NO 126
<211> LENGTH: 38
<212> TYPE: PRT
<213> ORGANISM: Artificial Sequence
<220> FEATURE:
<223> OTHER INFORMATION: Purification tag - SPB-tag

<400> SEQUENCE: 126

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
```

```
                        35

<210> SEQ ID NO 127
<211> LENGTH: 13
<212> TYPE: PRT
<213> ORGANISM: Artificial Sequence
<220> FEATURE:
<223> OTHER INFORMATION: Purification tag - Softag 1

<400> SEQUENCE: 127

Ser Leu Ala Glu Leu Leu Asn Ala Gly Leu Gly Gly Ser
1               5                   10

<210> SEQ ID NO 128
<211> LENGTH: 8
<212> TYPE: PRT
<213> ORGANISM: Artificial Sequence
<220> FEATURE:
<223> OTHER INFORMATION: Purification tag - Softag 3

<400> SEQUENCE: 128

Thr Gln Asp Pro Ser Arg Val Gly
1               5

<210> SEQ ID NO 129
<211> LENGTH: 14
<212> TYPE: PRT
<213> ORGANISM: Artificial Sequence
<220> FEATURE:
<223> OTHER INFORMATION: Purification tag - V5 tag

<400> SEQUENCE: 129

Gly Lys Pro Ile Pro Asn Pro Leu Leu Gly Leu Asp Ser Thr
1               5                   10

<210> SEQ ID NO 130
<211> LENGTH: 8
<212> TYPE: PRT
<213> ORGANISM: Artificial Sequence
<220> FEATURE:
<223> OTHER INFORMATION: Purification tag -  Xpress tag

<400> SEQUENCE: 130

Asp Leu Tyr Asp Asp Asp Asp Lys
1               5

<210> SEQ ID NO 131
<211> LENGTH: 6
<212> TYPE: PRT
<213> ORGANISM: Homo sapiens

<400> SEQUENCE: 131

Leu Val Pro Arg Gly Ser
1               5

<210> SEQ ID NO 132
<211> LENGTH: 5
<212> TYPE: PRT
<213> ORGANISM: Homo sapiens

<400> SEQUENCE: 132

Asp Asp Asp Asp Lys
1               5

<210> SEQ ID NO 133
<211> LENGTH: 4
```

```
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Glu or Asp

<400> SEQUENCE: 133

Ile Xaa Gly Arg
1

<210> SEQ ID NO 134
<211> LENGTH: 5
<212> TYPE: PRT
<213> ORGANISM: Homo sapiens

<400> SEQUENCE: 134

Asp Asp Asp Asp Lys
1               5

<210> SEQ ID NO 135
<211> LENGTH: 7
<212> TYPE: PRT
<213> ORGANISM: Homo sapiens

<400> SEQUENCE: 135

Glu Asn Leu Tyr Phe Gln Gly
1               5

<210> SEQ ID NO 136
<211> LENGTH: 8
<212> TYPE: PRT
<213> ORGANISM: Homo sapiens

<400> SEQUENCE: 136

Leu Glu Val Leu Phe Gln Gly Pro
1               5

<210> SEQ ID NO 137
<211> LENGTH: 100
<212> TYPE: PRT
<213> ORGANISM: Homo sapiens

<400> SEQUENCE: 137

Gly Ser Leu Gln Asp Ser Glu Val Asn Gln Glu Ala Lys Pro Glu Val
1               5                   10                  15

Lys Pro Glu Val Lys Pro Glu Thr His Ile Asn Leu Lys Val Ser Asp
            20                  25                  30

Gly Ser Ser Glu Ile Phe Phe Lys Ile Lys Lys Thr Thr Pro Leu Arg
        35                  40                  45

Arg Leu Met Glu Ala Phe Ala Lys Arg Gln Gly Lys Glu Met Asp Ser
    50                  55                  60

Leu Thr Phe Leu Tyr Asp Gly Ile Glu Ile Gln Ala Asp Gln Thr Pro
65                  70                  75                  80

Glu Asp Leu Asp Met Glu Asp Asn Asp Ile Ile Glu Ala His Arg Glu
                85                  90                  95

Gln Ile Gly Gly
            100

<210> SEQ ID NO 138
<211> LENGTH: 1289
<212> TYPE: PRT
<213> ORGANISM: Artificial Sequence
```

<220> FEATURE:
<223> OTHER INFORMATION: p97 fusion protein

<400> SEQUENCE: 138

```
Met Glu Trp Ser Trp Val Phe Leu Phe Phe Leu Ser Val Thr Thr Gly
1               5                   10                  15

Val His Ser Asp Tyr Lys Asp Asp Asp Lys Glu Gln Lys Leu Ile
            20                  25                  30

Ser Glu Glu Asp Leu His His His His His His His His Gly
35                  40                  45

Gly Gly Gly Glu Asn Leu Tyr Phe Gln Gly Ser Glu Thr Gln Ala Asn
        50                  55                  60

Ser Thr Thr Asp Ala Leu Asn Val Leu Leu Ile Ile Val Asp Asp Leu
65                  70                  75                  80

Arg Pro Ser Leu Gly Cys Tyr Gly Asp Lys Leu Val Arg Ser Pro Asn
                85                  90                  95

Ile Asp Gln Leu Ala Ser His Ser Leu Leu Phe Gln Asn Ala Phe Ala
            100                 105                 110

Gln Gln Ala Val Cys Ala Pro Ser Arg Val Ser Phe Leu Thr Gly Arg
        115                 120                 125

Arg Pro Asp Thr Thr Arg Leu Tyr Asp Phe Asn Ser Tyr Trp Arg Val
130                 135                 140

His Ala Gly Asn Phe Ser Thr Ile Pro Gln Tyr Phe Lys Glu Asn Gly
145                 150                 155                 160

Tyr Val Thr Met Ser Val Gly Lys Val Phe His Pro Gly Ile Ser Ser
                165                 170                 175

Asn His Thr Asp Asp Ser Pro Tyr Ser Trp Ser Phe Pro Pro Tyr His
            180                 185                 190

Pro Ser Ser Glu Lys Tyr Glu Asn Thr Lys Thr Cys Arg Gly Pro Asp
        195                 200                 205

Gly Glu Leu His Ala Asn Leu Leu Cys Pro Val Asp Val Leu Asp Val
210                 215                 220

Pro Glu Gly Thr Leu Pro Asp Lys Gln Ser Thr Glu Gln Ala Ile Gln
225                 230                 235                 240

Leu Leu Glu Lys Met Lys Thr Ser Ala Ser Pro Phe Phe Leu Ala Val
                245                 250                 255

Gly Tyr His Lys Pro His Ile Pro Phe Arg Tyr Pro Lys Glu Phe Gln
            260                 265                 270

Lys Leu Tyr Pro Leu Glu Asn Ile Thr Leu Ala Pro Asp Pro Glu Val
        275                 280                 285

Pro Asp Gly Leu Pro Pro Val Ala Tyr Asn Pro Trp Met Asp Ile Arg
290                 295                 300

Gln Arg Glu Asp Val Gln Ala Leu Asn Ile Ser Val Pro Tyr Gly Pro
305                 310                 315                 320

Ile Pro Val Asp Phe Gln Arg Lys Ile Arg Gln Ser Tyr Phe Ala Ser
                325                 330                 335

Val Ser Tyr Leu Asp Thr Gln Val Gly Arg Leu Leu Ser Ala Leu Asp
            340                 345                 350

Asp Leu Gln Leu Ala Asn Ser Thr Ile Ile Ala Phe Thr Ser Asp His
        355                 360                 365

Gly Trp Ala Leu Gly Glu His Gly Glu Trp Ala Lys Tyr Ser Asn Phe
370                 375                 380

Asp Val Ala Thr His Val Pro Leu Ile Phe Tyr Val Pro Gly Arg Thr
385                 390                 395                 400
```

```
Ala Ser Leu Pro Glu Ala Gly Lys Leu Phe Pro Tyr Leu Asp Pro
            405                 410                 415

Phe Asp Ser Ala Ser Gln Leu Met Glu Pro Gly Arg Gln Ser Met Asp
            420                 425                 430

Leu Val Glu Leu Val Ser Leu Phe Pro Thr Leu Ala Gly Leu Ala Gly
            435                 440                 445

Leu Gln Val Pro Pro Arg Cys Pro Val Pro Ser Phe His Val Glu Leu
            450                 455                 460

Cys Arg Glu Gly Lys Asn Leu Leu Lys His Phe Arg Phe Arg Asp Leu
465                 470                 475                 480

Glu Glu Asp Pro Tyr Leu Pro Gly Asn Pro Arg Glu Leu Ile Ala Tyr
                485                 490                 495

Ser Gln Tyr Pro Arg Pro Ser Asp Ile Pro Gln Trp Asn Ser Asp Lys
            500                 505                 510

Pro Ser Leu Lys Asp Ile Lys Ile Met Gly Tyr Ser Ile Arg Thr Ile
            515                 520                 525

Asp Tyr Arg Tyr Thr Val Trp Val Gly Phe Asn Pro Asp Glu Phe Leu
            530                 535                 540

Ala Asn Phe Ser Asp Ile His Ala Gly Glu Leu Tyr Phe Val Asp Ser
545                 550                 555                 560

Asp Pro Leu Gln Asp His Asn Met Tyr Asn Asp Ser Gln Gly Gly Asp
                565                 570                 575

Leu Phe Gln Leu Leu Met Pro Glu Ala Ala Lys Glu Ala Ala Ala
            580                 585                 590

Lys Glu Ala Ala Ala Lys Gly Met Glu Val Arg Trp Cys Ala Thr Ser
            595                 600                 605

Asp Pro Glu Gln His Lys Cys Gly Asn Met Ser Glu Ala Phe Arg Glu
610                 615                 620

Ala Gly Ile Gln Pro Ser Leu Leu Cys Val Arg Gly Thr Ser Ala Asp
625                 630                 635                 640

His Cys Val Gln Leu Ile Ala Ala Gln Glu Ala Asp Ala Ile Thr Leu
            645                 650                 655

Asp Gly Gly Ala Ile Tyr Glu Ala Gly Lys Glu His Gly Leu Lys Pro
            660                 665                 670

Val Val Gly Glu Val Tyr Asp Gln Glu Val Gly Thr Ser Tyr Tyr Ala
            675                 680                 685

Val Ala Val Val Arg Arg Ser Ser His Val Thr Ile Asp Thr Leu Lys
            690                 695                 700

Gly Val Lys Ser Cys His Thr Gly Ile Asn Arg Thr Val Gly Trp Asn
705                 710                 715                 720

Val Pro Val Gly Tyr Leu Val Glu Ser Gly Arg Leu Ser Val Met Gly
                725                 730                 735

Cys Asp Val Leu Lys Ala Val Ser Asp Tyr Phe Gly Gly Ser Cys Val
            740                 745                 750

Pro Gly Ala Gly Glu Thr Ser Tyr Ser Glu Ser Leu Cys Arg Leu Cys
            755                 760                 765

Arg Gly Asp Ser Ser Gly Glu Gly Val Cys Asp Lys Ser Pro Leu Glu
770                 775                 780

Arg Tyr Tyr Asp Tyr Ser Gly Ala Phe Arg Cys Leu Ala Glu Gly Ala
785                 790                 795                 800

Gly Asp Val Ala Phe Val Lys His Ser Thr Val Leu Glu Asn Thr Asp
                805                 810                 815
```

```
Gly Lys Thr Leu Pro Ser Trp Gly Gln Ala Leu Leu Ser Gln Asp Phe
                820                 825                 830

Glu Leu Leu Cys Arg Asp Gly Ser Arg Ala Asp Val Thr Glu Trp Arg
            835                 840                 845

Gln Cys His Leu Ala Arg Val Pro Ala His Ala Val Val Arg Ala
850                 855                 860

Asp Thr Asp Gly Gly Leu Ile Phe Arg Leu Leu Asn Glu Gly Gln Arg
865                 870                 875                 880

Leu Phe Ser His Glu Gly Ser Ser Phe Gln Met Phe Ser Glu Ala
                885                 890                 895

Tyr Gly Gln Lys Asp Leu Leu Phe Lys Asp Ser Thr Ser Glu Leu Val
                900                 905                 910

Pro Ile Ala Thr Gln Thr Tyr Glu Ala Trp Leu Gly His Glu Tyr Leu
                915                 920                 925

His Ala Met Lys Gly Leu Leu Cys Asp Pro Asn Arg Leu Pro Pro Tyr
            930                 935                 940

Leu Arg Trp Cys Val Leu Ser Thr Pro Glu Ile Gln Lys Cys Gly Asp
945                 950                 955                 960

Met Ala Val Ala Phe Arg Arg Gln Arg Leu Lys Pro Glu Ile Gln Cys
                965                 970                 975

Val Ser Ala Lys Ser Pro Gln His Cys Met Glu Arg Ile Gln Ala Glu
                980                 985                 990

Gln Val Asp Ala Val Thr Leu Ser  Gly Glu Asp Ile Tyr  Thr Ala Gly
                995                 1000                1005

Lys Thr Tyr Gly Leu Val Pro  Ala Ala Gly Glu His  Tyr Ala Pro
            1010                1015                1020

Glu Asp Ser Ser Asn Ser Tyr  Tyr Val Val Ala Val  Val Arg Arg
            1025                1030                1035

Asp Ser Ser His Ala Phe Thr  Leu Asp Glu Leu Arg  Gly Lys Arg
            1040                1045                1050

Ser Cys His Ala Gly Phe Gly  Ser Pro Ala Gly Trp  Asp Val Pro
            1055                1060                1065

Val Gly Ala Leu Ile Gln Arg  Gly Phe Ile Arg Pro  Lys Asp Cys
            1070                1075                1080

Asp Val Leu Thr Ala Val Ser  Glu Phe Phe Asn Ala  Ser Cys Val
            1085                1090                1095

Pro Val Asn Asn Pro Lys Asn  Tyr Pro Ser Ser Leu  Cys Ala Leu
            1100                1105                1110

Cys Val Gly Asp Glu Gln Gly  Arg Asn Lys Cys Val  Gly Asn Ser
            1115                1120                1125

Gln Glu Arg Tyr Tyr Gly Tyr  Arg Gly Ala Phe Arg  Cys Leu Val
            1130                1135                1140

Glu Asn Ala Gly Asp Val Ala  Phe Val Arg His Thr  Thr Val Phe
            1145                1150                1155

Asp Asn Thr Asn Gly His Asn  Ser Glu Pro Trp Ala  Ala Glu Leu
            1160                1165                1170

Arg Ser Glu Asp Tyr Glu Leu  Leu Cys Pro Asn Gly  Ala Arg Ala
            1175                1180                1185

Glu Val Ser Gln Phe Ala Ala  Cys Asn Leu Ala Gln  Ile Pro Pro
            1190                1195                1200

His Ala Val Met Val Arg Pro  Asp Thr Asn Ile Phe  Thr Val Tyr
            1205                1210                1215

Gly Leu Leu Asp Lys Ala Gln  Asp Leu Phe Gly Asp  Asp His Asn
```

```
                    1220                1225                1230
Lys Asn Gly Phe Lys Met Phe Asp Ser Ser Asn Tyr His Gly Gln
            1235                1240                1245
Asp Leu Leu Phe Lys Asp Ala Thr Val Arg Ala Val Pro Val Gly
        1250                1255                1260
Glu Lys Thr Thr Tyr Arg Gly Trp Leu Gly Leu Asp Tyr Val Ala
    1265                1270                1275
Ala Leu Glu Gly Met Ser Ser Gln Gln Cys Ser
        1280                1285

<210> SEQ ID NO 139
<211> LENGTH: 1289
<212> TYPE: PRT
<213> ORGANISM: Artificial Sequence
<220> FEATURE:
<223> OTHER INFORMATION: p97 fusion protein

<400> SEQUENCE: 139

Met Glu Trp Ser Trp Val Phe Leu Phe Phe Leu Ser Val Thr Thr Gly
1               5                   10                  15
Val His Ser Asp Tyr Lys Asp Asp Asp Asp Lys Glu Gln Lys Leu Ile
            20                  25                  30
Ser Glu Glu Asp Leu His His His His His His His His Gly
        35                  40                  45
Gly Gly Gly Glu Asn Leu Tyr Phe Gln Gly Gly Met Glu Val Arg Trp
    50                  55                  60
Cys Ala Thr Ser Asp Pro Glu Gln His Lys Cys Gly Asn Met Ser Glu
65                  70                  75                  80
Ala Phe Arg Glu Ala Gly Ile Gln Pro Ser Leu Leu Cys Val Arg Gly
                85                  90                  95
Thr Ser Ala Asp His Cys Val Gln Leu Ile Ala Ala Gln Glu Ala Asp
            100                 105                 110
Ala Ile Thr Leu Asp Gly Gly Ala Ile Tyr Glu Ala Gly Lys Glu His
        115                 120                 125
Gly Leu Lys Pro Val Val Gly Glu Val Tyr Asp Gln Glu Val Gly Thr
    130                 135                 140
Ser Tyr Tyr Ala Val Ala Val Val Arg Arg Ser Ser His Val Thr Ile
145                 150                 155                 160
Asp Thr Leu Lys Gly Val Lys Ser Cys His Thr Gly Ile Asn Arg Thr
                165                 170                 175
Val Gly Trp Asn Val Pro Val Gly Tyr Leu Val Glu Ser Gly Arg Leu
            180                 185                 190
Ser Val Met Gly Cys Asp Val Leu Lys Ala Val Ser Asp Tyr Phe Gly
        195                 200                 205
Gly Ser Cys Val Pro Gly Ala Gly Glu Thr Ser Tyr Ser Glu Ser Leu
    210                 215                 220
Cys Arg Leu Cys Arg Gly Asp Ser Ser Gly Glu Gly Val Cys Asp Lys
225                 230                 235                 240
Ser Pro Leu Glu Arg Tyr Tyr Asp Tyr Ser Gly Ala Phe Arg Cys Leu
                245                 250                 255
Ala Glu Gly Ala Gly Asp Val Ala Phe Val Lys His Ser Thr Val Leu
            260                 265                 270
Glu Asn Thr Asp Gly Lys Thr Leu Pro Ser Trp Gly Gln Ala Leu Leu
        275                 280                 285
Ser Gln Asp Phe Glu Leu Leu Cys Arg Asp Gly Ser Arg Ala Asp Val
```

```
                290             295             300
Thr Glu Trp Arg Gln Cys His Leu Ala Arg Val Pro Ala His Ala Val
305                 310             315                 320

Val Val Arg Ala Asp Thr Asp Gly Gly Leu Ile Phe Arg Leu Leu Asn
                325             330             335

Glu Gly Gln Arg Leu Phe Ser His Glu Gly Ser Ser Phe Gln Met Phe
                340             345             350

Ser Ser Glu Ala Tyr Gly Gln Lys Asp Leu Leu Phe Lys Asp Ser Thr
        355             360             365

Ser Glu Leu Val Pro Ile Ala Thr Gln Thr Tyr Glu Ala Trp Leu Gly
        370             375             380

His Glu Tyr Leu His Ala Met Lys Gly Leu Leu Cys Asp Pro Asn Arg
385             390             395             400

Leu Pro Pro Tyr Leu Arg Trp Cys Val Leu Ser Thr Pro Glu Ile Gln
                405             410             415

Lys Cys Gly Asp Met Ala Val Ala Phe Arg Arg Gln Arg Leu Lys Pro
                420             425             430

Glu Ile Gln Cys Val Ser Ala Lys Ser Pro Gln His Cys Met Glu Arg
            435             440             445

Ile Gln Ala Glu Gln Val Asp Ala Val Thr Leu Ser Gly Glu Asp Ile
450             455             460

Tyr Thr Ala Gly Lys Thr Tyr Gly Leu Val Pro Ala Ala Gly Glu His
465             470             475             480

Tyr Ala Pro Glu Asp Ser Ser Asn Ser Tyr Tyr Val Ala Val Val
            485             490             495

Arg Arg Asp Ser Ser His Ala Phe Thr Leu Asp Glu Leu Arg Gly Lys
            500             505             510

Arg Ser Cys His Ala Gly Phe Gly Ser Pro Ala Gly Trp Asp Val Pro
            515             520             525

Val Gly Ala Leu Ile Gln Arg Gly Phe Ile Arg Pro Lys Asp Cys Asp
            530             535             540

Val Leu Thr Ala Val Ser Glu Phe Phe Asn Ala Ser Cys Val Pro Val
545             550             555             560

Asn Asn Pro Lys Asn Tyr Pro Ser Ser Leu Cys Ala Leu Cys Val Gly
                565             570             575

Asp Glu Gln Gly Arg Asn Lys Cys Val Gly Asn Ser Gln Glu Arg Tyr
            580             585             590

Tyr Gly Tyr Arg Gly Ala Phe Arg Cys Leu Val Glu Asn Ala Gly Asp
        595             600             605

Val Ala Phe Val Arg His Thr Thr Val Phe Asp Asn Thr Asn Gly His
610             615             620

Asn Ser Glu Pro Trp Ala Glu Leu Arg Ser Glu Asp Tyr Glu Leu
625             630             635             640

Leu Cys Pro Asn Gly Ala Arg Ala Glu Val Ser Gln Phe Ala Ala Cys
                645             650             655

Asn Leu Ala Gln Ile Pro Pro His Ala Val Met Val Arg Pro Asp Thr
                660             665             670

Asn Ile Phe Thr Val Tyr Gly Leu Leu Asp Lys Ala Gln Asp Leu Phe
            675             680             685

Gly Asp Asp His Asn Lys Asn Gly Phe Lys Met Phe Asp Ser Ser Asn
            690             695             700

Tyr His Gly Gln Asp Leu Leu Phe Lys Asp Ala Thr Val Arg Ala Val
705             710             715             720
```

-continued

```
Pro Val Gly Glu Lys Thr Thr Tyr Arg Gly Trp Leu Gly Leu Asp Tyr
                725                 730                 735

Val Ala Ala Leu Glu Gly Met Ser Ser Gln Gln Cys Ser Glu Ala Ala
            740                 745                 750

Ala Lys Glu Ala Ala Lys Glu Ala Ala Lys Ser Glu Thr Gln
        755                 760                 765

Ala Asn Ser Thr Thr Asp Ala Leu Asn Val Leu Ile Ile Val Asp
    770                 775                 780

Asp Leu Arg Pro Ser Leu Gly Cys Tyr Gly Asp Lys Leu Val Arg Ser
785                 790                 795                 800

Pro Asn Ile Asp Gln Leu Ala Ser His Ser Leu Leu Phe Gln Asn Ala
                805                 810                 815

Phe Ala Gln Gln Ala Val Cys Ala Pro Ser Arg Val Ser Phe Leu Thr
                820                 825                 830

Gly Arg Arg Pro Asp Thr Thr Arg Leu Tyr Asp Phe Asn Ser Tyr Trp
                835                 840                 845

Arg Val His Ala Gly Asn Phe Ser Thr Ile Pro Gln Tyr Phe Lys Glu
    850                 855                 860

Asn Gly Tyr Val Thr Met Ser Val Gly Lys Val Phe His Pro Gly Ile
865                 870                 875                 880

Ser Ser Asn His Thr Asp Asp Ser Pro Tyr Ser Trp Ser Phe Pro Pro
                885                 890                 895

Tyr His Pro Ser Ser Glu Lys Tyr Glu Asn Thr Lys Thr Cys Arg Gly
                900                 905                 910

Pro Asp Gly Glu Leu His Ala Asn Leu Leu Cys Pro Val Asp Val Leu
            915                 920                 925

Asp Val Pro Glu Gly Thr Leu Pro Asp Lys Gln Ser Thr Glu Gln Ala
        930                 935                 940

Ile Gln Leu Leu Glu Lys Met Lys Thr Ser Ala Ser Pro Phe Phe Leu
945                 950                 955                 960

Ala Val Gly Tyr His Lys Pro His Ile Pro Phe Arg Tyr Pro Lys Glu
                965                 970                 975

Phe Gln Lys Leu Tyr Pro Leu Glu Asn Ile Thr Leu Ala Pro Asp Pro
            980                 985                 990

Glu Val Pro Asp Gly Leu Pro Pro Val Ala Tyr Asn Pro Trp Met Asp
        995                 1000                1005

Ile Arg Gln Arg Glu Asp Val Gln Ala Leu Asn Ile Ser Val Pro
    1010                1015                1020

Tyr Gly Pro Ile Pro Val Asp Phe Gln Arg Lys Ile Arg Gln Ser
    1025                1030                1035

Tyr Phe Ala Ser Val Ser Tyr Leu Asp Thr Gln Val Gly Arg Leu
    1040                1045                1050

Leu Ser Ala Leu Asp Asp Leu Gln Leu Ala Asn Ser Thr Ile Ile
    1055                1060                1065

Ala Phe Thr Ser Asp His Gly Trp Ala Leu Gly Glu His Gly Glu
    1070                1075                1080

Trp Ala Lys Tyr Ser Asn Phe Asp Val Ala Thr His Val Pro Leu
    1085                1090                1095

Ile Phe Tyr Val Pro Gly Arg Thr Ala Ser Leu Pro Glu Ala Gly
    1100                1105                1110

Glu Lys Leu Phe Pro Tyr Leu Asp Pro Phe Asp Ser Ala Ser Gln
    1115                1120                1125
```

-continued

```
Leu Met Glu Pro Gly Arg Gln Ser Met Asp Leu Val Glu Leu Val
    1130                1135                1140

Ser Leu Phe Pro Thr Leu Ala Gly Leu Ala Gly Leu Gln Val Pro
1145                1150                1155

Pro Arg Cys Pro Val Pro Ser Phe His Val Glu Leu Cys Arg Glu
    1160                1165                1170

Gly Lys Asn Leu Leu Lys His Phe Arg Phe Arg Asp Leu Glu Glu
    1175                1180                1185

Asp Pro Tyr Leu Pro Gly Asn Pro Arg Glu Leu Ile Ala Tyr Ser
    1190                1195                1200

Gln Tyr Pro Arg Pro Ser Ile Pro Gln Trp Asn Ser Asp Lys
    1205                1210                1215

Pro Ser Leu Lys Asp Ile Lys Ile Met Gly Tyr Ser Ile Arg Thr
    1220                1225                1230

Ile Asp Tyr Arg Tyr Thr Val Trp Val Gly Phe Asn Pro Asp Glu
    1235                1240                1245

Phe Leu Ala Asn Phe Ser Asp Ile His Ala Gly Glu Leu Tyr Phe
    1250                1255                1260

Val Asp Ser Asp Pro Leu Gln Asp His Asn Met Tyr Asn Asp Ser
    1265                1270                1275

Gln Gly Gly Asp Leu Phe Gln Leu Leu Met Pro
    1280                1285

<210> SEQ ID NO 140
<211> LENGTH: 611
<212> TYPE: PRT
<213> ORGANISM: Artificial Sequence
<220> FEATURE:
<223> OTHER INFORMATION: p97 fusion protein

<400> SEQUENCE: 140

Met Glu Trp Ser Trp Val Phe Leu Phe Phe Leu Ser Val Thr Thr Gly
1               5                   10                  15

Val His Ser Asp Tyr Lys Asp Asp Asp Lys Glu Gln Lys Leu Ile
                20                  25                  30

Ser Glu Glu Asp Leu His His His His His His His His Gly
            35                  40                  45

Gly Gly Gly Glu Asn Leu Tyr Phe Gln Gly Asp Ser Ser His Ala Phe
    50                  55                  60

Thr Leu Asp Glu Leu Arg Tyr Glu Ala Ala Lys Glu Ala Ala
65              70                  75                  80

Lys Glu Ala Ala Ala Lys Ser Glu Thr Gln Ala Asn Ser Thr Thr Asp
                85                  90                  95

Ala Leu Asn Val Leu Leu Ile Ile Val Asp Asp Leu Arg Pro Ser Leu
                100                 105                 110

Gly Cys Tyr Gly Asp Lys Leu Val Arg Ser Pro Asn Ile Asp Gln Leu
            115                 120                 125

Ala Ser His Ser Leu Leu Phe Gln Asn Ala Phe Ala Gln Gln Ala Val
        130                 135                 140

Cys Ala Pro Ser Arg Val Ser Phe Leu Thr Gly Arg Arg Pro Asp Thr
145                 150                 155                 160

Thr Arg Leu Tyr Asp Phe Asn Ser Tyr Trp Arg Val His Ala Gly Asn
                165                 170                 175

Phe Ser Thr Ile Pro Gln Tyr Phe Lys Glu Asn Gly Tyr Val Thr Met
                180                 185                 190
```

```
Ser Val Gly Lys Val Phe His Pro Gly Ile Ser Ser Asn His Thr Asp
        195                 200                 205

Asp Ser Pro Tyr Ser Trp Ser Phe Pro Pro Tyr His Pro Ser Ser Glu
    210                 215                 220

Lys Tyr Glu Asn Thr Lys Thr Cys Arg Gly Pro Asp Gly Glu Leu His
225                 230                 235                 240

Ala Asn Leu Leu Cys Pro Val Asp Val Leu Asp Val Pro Glu Gly Thr
                245                 250                 255

Leu Pro Asp Lys Gln Ser Thr Glu Gln Ala Ile Gln Leu Leu Glu Lys
            260                 265                 270

Met Lys Thr Ser Ala Ser Pro Phe Phe Leu Ala Val Gly Tyr His Lys
        275                 280                 285

Pro His Ile Pro Phe Arg Tyr Pro Lys Glu Phe Gln Lys Leu Tyr Pro
    290                 295                 300

Leu Glu Asn Ile Thr Leu Ala Pro Asp Pro Glu Val Pro Asp Gly Leu
305                 310                 315                 320

Pro Pro Val Ala Tyr Asn Pro Trp Met Asp Ile Arg Gln Arg Glu Asp
                325                 330                 335

Val Gln Ala Leu Asn Ile Ser Val Pro Tyr Gly Pro Ile Pro Val Asp
            340                 345                 350

Phe Gln Arg Lys Ile Arg Gln Ser Tyr Phe Ala Ser Val Ser Tyr Leu
        355                 360                 365

Asp Thr Gln Val Gly Arg Leu Leu Ser Ala Leu Asp Asp Leu Gln Leu
    370                 375                 380

Ala Asn Ser Thr Ile Ile Ala Phe Thr Ser Asp His Gly Trp Ala Leu
385                 390                 395                 400

Gly Glu His Gly Glu Trp Ala Lys Tyr Ser Asn Phe Asp Val Ala Thr
                405                 410                 415

His Val Pro Leu Ile Phe Tyr Val Pro Gly Arg Thr Ala Ser Leu Pro
            420                 425                 430

Glu Ala Gly Glu Lys Leu Phe Pro Tyr Leu Asp Pro Phe Asp Ser Ala
        435                 440                 445

Ser Gln Leu Met Glu Pro Gly Arg Gln Ser Met Asp Leu Val Glu Leu
    450                 455                 460

Val Ser Leu Phe Pro Thr Leu Ala Gly Leu Ala Gly Leu Gln Val Pro
465                 470                 475                 480

Pro Arg Cys Pro Val Pro Ser Phe His Val Glu Leu Cys Arg Glu Gly
                485                 490                 495

Lys Asn Leu Leu Lys His Phe Arg Phe Arg Asp Leu Glu Glu Asp Pro
            500                 505                 510

Tyr Leu Pro Gly Asn Pro Arg Glu Leu Ile Ala Tyr Ser Gln Tyr Pro
        515                 520                 525

Arg Pro Ser Asp Ile Pro Gln Trp Asn Ser Asp Lys Pro Ser Leu Lys
    530                 535                 540

Asp Ile Lys Ile Met Gly Tyr Ser Ile Arg Thr Ile Asp Tyr Arg Tyr
545                 550                 555                 560

Thr Val Trp Val Gly Phe Asn Pro Asp Glu Phe Leu Ala Asn Phe Ser
                565                 570                 575

Asp Ile His Ala Gly Glu Leu Tyr Phe Val Asp Ser Asp Pro Leu Gln
            580                 585                 590

Asp His Asn Met Tyr Asn Asp Ser Gln Gly Gly Asp Leu Phe Gln Leu
        595                 600                 605

Leu Met Pro
```

```
<210> SEQ ID NO 141
<211> LENGTH: 611
<212> TYPE: PRT
<213> ORGANISM: Artificial Sequence
<220> FEATURE:
<223> OTHER INFORMATION: p97 fusion protein

<400> SEQUENCE: 141
```

Met Glu Trp Ser Trp Val Phe Leu Phe Phe Leu Ser Val Thr Thr Gly
1               5                   10                  15

Val His Ser Asp Tyr Lys Asp Asp Asp Lys Glu Gln Lys Leu Ile
        20                  25                  30

Ser Glu Glu Asp Leu His His His His His His His His Gly
        35                  40                  45

Gly Gly Gly Glu Asn Leu Tyr Phe Gln Gly Ser Glu Thr Gln Ala Asn
    50                  55                  60

Ser Thr Thr Asp Ala Leu Asn Val Leu Leu Ile Ile Val Asp Asp Leu
65                  70                  75                  80

Arg Pro Ser Leu Gly Cys Tyr Gly Asp Lys Leu Val Arg Ser Pro Asn
                85                  90                  95

Ile Asp Gln Leu Ala Ser His Ser Leu Leu Phe Gln Asn Ala Phe Ala
            100                 105                 110

Gln Gln Ala Val Cys Ala Pro Ser Arg Val Ser Phe Leu Thr Gly Arg
        115                 120                 125

Arg Pro Asp Thr Thr Arg Leu Tyr Asp Phe Asn Ser Tyr Trp Arg Val
    130                 135                 140

His Ala Gly Asn Phe Ser Thr Ile Pro Gln Tyr Phe Lys Glu Asn Gly
145                 150                 155                 160

Tyr Val Thr Met Ser Val Gly Lys Val Phe His Pro Gly Ile Ser Ser
                165                 170                 175

Asn His Thr Asp Asp Ser Pro Tyr Ser Trp Ser Phe Pro Pro Tyr His
            180                 185                 190

Pro Ser Ser Glu Lys Tyr Glu Asn Thr Lys Thr Cys Arg Gly Pro Asp
        195                 200                 205

Gly Glu Leu His Ala Asn Leu Leu Cys Pro Val Asp Val Leu Asp Val
    210                 215                 220

Pro Glu Gly Thr Leu Pro Asp Lys Gln Ser Thr Glu Gln Ala Ile Gln
225                 230                 235                 240

Leu Leu Glu Lys Met Lys Thr Ser Ala Ser Pro Phe Phe Leu Ala Val
                245                 250                 255

Gly Tyr His Lys Pro His Ile Pro Phe Arg Tyr Pro Lys Glu Phe Gln
            260                 265                 270

Lys Leu Tyr Pro Leu Glu Asn Ile Thr Leu Ala Pro Asp Pro Glu Val
        275                 280                 285

Pro Asp Gly Leu Pro Pro Val Ala Tyr Asn Pro Trp Met Asp Ile Arg
    290                 295                 300

Gln Arg Glu Asp Val Gln Ala Leu Asn Ile Ser Val Pro Tyr Gly Pro
305                 310                 315                 320

Ile Pro Val Asp Phe Gln Arg Lys Ile Arg Gln Ser Tyr Phe Ala Ser
                325                 330                 335

Val Ser Tyr Leu Asp Thr Gln Val Gly Arg Leu Leu Ser Ala Leu Asp
            340                 345                 350

Asp Leu Gln Leu Ala Asn Ser Thr Ile Ile Ala Phe Thr Ser Asp His

```
                    355                 360                 365
Gly Trp Ala Leu Gly Glu His Gly Glu Trp Ala Lys Tyr Ser Asn Phe
370                 375                 380

Asp Val Ala Thr His Val Pro Leu Ile Phe Tyr Val Pro Gly Arg Thr
385                 390                 395                 400

Ala Ser Leu Pro Glu Ala Gly Glu Lys Leu Phe Pro Tyr Leu Asp Pro
                405                 410                 415

Phe Asp Ser Ala Ser Gln Leu Met Glu Pro Gly Arg Gln Ser Met Asp
                420                 425                 430

Leu Val Glu Leu Val Ser Leu Phe Pro Thr Leu Ala Gly Leu Ala Gly
            435                 440                 445

Leu Gln Val Pro Pro Arg Cys Pro Val Pro Ser Phe His Val Glu Leu
450                 455                 460

Cys Arg Glu Gly Lys Asn Leu Leu Lys His Phe Arg Phe Arg Asp Leu
465                 470                 475                 480

Glu Glu Asp Pro Tyr Leu Pro Gly Asn Pro Arg Glu Leu Ile Ala Tyr
                485                 490                 495

Ser Gln Tyr Pro Arg Pro Ser Asp Ile Pro Gln Trp Asn Ser Asp Lys
                500                 505                 510

Pro Ser Leu Lys Asp Ile Lys Ile Met Gly Tyr Ser Ile Arg Thr Ile
            515                 520                 525

Asp Tyr Arg Tyr Thr Val Trp Val Gly Phe Asn Pro Asp Glu Phe Leu
530                 535                 540

Ala Asn Phe Ser Asp Ile His Ala Gly Glu Leu Tyr Phe Val Asp Ser
545                 550                 555                 560

Asp Pro Leu Gln Asp His Asn Met Tyr Asn Asp Ser Gln Gly Gly Asp
                565                 570                 575

Leu Phe Gln Leu Leu Met Pro Glu Ala Ala Ala Lys Glu Ala Ala Ala
                580                 585                 590

Lys Glu Ala Ala Ala Lys Asp Ser Ser His Ala Phe Thr Leu Asp Glu
            595                 600                 605

Leu Arg Tyr
    610

<210> SEQ ID NO 142
<211> LENGTH: 603
<212> TYPE: PRT
<213> ORGANISM: Artificial Sequence
<220> FEATURE:
<223> OTHER INFORMATION: p97 fusion protein

<400> SEQUENCE: 142

Met Glu Trp Ser Trp Val Phe Leu Phe Phe Leu Ser Val Thr Thr Gly
1               5                   10                  15

Val His Ser Asp Tyr Lys Asp Asp Asp Lys Glu Gln Lys Leu Ile
            20                  25                  30

Ser Glu Glu Asp Leu His His His His His His His His Gly
        35                  40                  45

Gly Gly Gly Glu Asn Leu Tyr Phe Gln Gly Thr Asp Ala Leu Asn Val
    50                  55                  60

Leu Leu Ile Ile Val Asp Asp Leu Arg Pro Ser Leu Gly Cys Tyr Gly
65                  70                  75                  80

Asp Lys Leu Val Arg Ser Pro Asn Ile Asp Gln Leu Ala Ser His Ser
                85                  90                  95

Leu Leu Phe Gln Asn Ala Phe Ala Gln Gln Ala Val Cys Ala Pro Ser
```

```
                100             105             110
Arg Val Ser Phe Leu Thr Gly Arg Arg Pro Asp Thr Thr Arg Leu Tyr
            115             120             125

Asp Phe Asn Ser Tyr Trp Arg Val His Ala Gly Asn Phe Ser Thr Ile
            130             135             140

Pro Gln Tyr Phe Lys Glu Asn Gly Tyr Val Thr Met Ser Val Gly Lys
145             150             155             160

Val Phe His Pro Gly Ile Ser Ser Asn His Thr Asp Asp Ser Pro Tyr
                165             170             175

Ser Trp Ser Phe Pro Pro Tyr His Pro Ser Ser Glu Lys Tyr Glu Asn
            180             185             190

Thr Lys Thr Cys Arg Gly Pro Asp Gly Glu Leu His Ala Asn Leu Leu
            195             200             205

Cys Pro Val Asp Val Leu Asp Val Pro Glu Gly Thr Leu Pro Asp Lys
        210             215             220

Gln Ser Thr Glu Gln Ala Ile Gln Leu Leu Glu Lys Met Lys Thr Ser
225             230             235             240

Ala Ser Pro Phe Phe Leu Ala Val Gly Tyr His Lys Pro His Ile Pro
                245             250             255

Phe Arg Tyr Pro Lys Glu Phe Gln Lys Leu Tyr Pro Leu Glu Asn Ile
            260             265             270

Thr Leu Ala Pro Asp Pro Glu Val Pro Asp Gly Leu Pro Pro Val Ala
            275             280             285

Tyr Asn Pro Trp Met Asp Ile Arg Gln Arg Glu Asp Val Gln Ala Leu
        290             295             300

Asn Ile Ser Val Pro Tyr Gly Pro Ile Pro Val Asp Phe Gln Arg Lys
305             310             315             320

Ile Arg Gln Ser Tyr Phe Ala Ser Val Ser Tyr Leu Asp Thr Gln Val
                325             330             335

Gly Arg Leu Leu Ser Ala Leu Asp Asp Leu Gln Leu Ala Asn Ser Thr
            340             345             350

Ile Ile Ala Phe Thr Ser Asp His Gly Trp Ala Leu Gly Glu His Gly
            355             360             365

Glu Trp Ala Lys Tyr Ser Asn Phe Asp Val Ala Thr His Val Pro Leu
        370             375             380

Ile Phe Tyr Val Pro Gly Arg Thr Ala Ser Leu Pro Glu Ala Gly Glu
385             390             395             400

Lys Leu Phe Pro Tyr Leu Asp Pro Phe Asp Ser Ala Ser Gln Leu Met
                405             410             415

Glu Pro Gly Arg Gln Ser Met Asp Leu Val Glu Leu Val Ser Leu Phe
            420             425             430

Pro Thr Leu Ala Gly Leu Ala Gly Leu Gln Val Pro Pro Arg Cys Pro
            435             440             445

Val Pro Ser Phe His Val Glu Leu Cys Arg Glu Gly Lys Asn Leu Leu
        450             455             460

Lys His Phe Arg Phe Arg Asp Leu Glu Glu Asp Pro Tyr Leu Pro Gly
465             470             475             480

Asn Pro Arg Glu Leu Ile Ala Tyr Ser Gln Tyr Pro Arg Pro Ser Asp
                485             490             495

Ile Pro Gln Trp Asn Ser Asp Lys Pro Ser Leu Lys Asp Ile Lys Ile
            500             505             510

Met Gly Tyr Ser Ile Arg Thr Ile Asp Tyr Arg Tyr Thr Val Trp Val
            515             520             525
```

```
Gly Phe Asn Pro Asp Glu Phe Leu Ala Asn Phe Ser Asp Ile His Ala
            530                 535                 540

Gly Glu Leu Tyr Phe Val Asp Ser Asp Pro Leu Gln Asp His Asn Met
545                 550                 555                 560

Tyr Asn Asp Ser Gln Gly Gly Asp Leu Phe Gln Leu Leu Met Pro Glu
                565                 570                 575

Ala Ala Ala Lys Glu Ala Ala Ala Lys Glu Ala Ala Ala Lys Asp Ser
                580                 585                 590

Ser His Ala Phe Thr Leu Asp Glu Leu Arg Tyr
                595                 600

<210> SEQ ID NO 143
<211> LENGTH: 3870
<212> TYPE: DNA
<213> ORGANISM: Artificial Sequence
<220> FEATURE:
<223> OTHER INFORMATION: Polynucleotide coding for p97 fusion protein

<400> SEQUENCE: 143
atggaatgga gctgggtctt tctcttcttc ctgtcagtaa cgactggtgt ccactccgac      60
tacaaggacg acgacgacaa agagcagaag ctgatctccg aagaggacct gcaccaccat     120
catcaccatc accaccatca cggaggcggt ggagagaacc tgtactttca gggctcggaa     180
actcaggcca actccaccac agatgcactc aacgtgctgc tgatcatcgt agatgacctc     240
cgaccttctc tgggctgtta cggcgacaag ctagtacgga gcccaaacat cgaccagctc     300
gcatcgcact ctctcctatt ccagaacgca ttcgcccagc aggctgtctg tgctccctcc     360
cgagtgtcct tcctcacggg tcggagaccc gataccacga ggttatatga cttcaactca     420
tactggcgcg tgcatgccgg taactttttct actataccc agtatttaa agaaaatggc     480 tatgttacaa tgtccgttgg caaggtattt catcctggta ttagcagcaa ccacacagat     540
gactctccgt atagctggtc attcccacca taccaccct ccagcgaaaa gtacgaaaac     600
acaaagactt gccggggccc agatggcgaa ctgcacgcaa atctgctgtg ccctgtagat     660
gtcttggacg tgcccgaagg tactctgccc gacaaacagt ccacagaaca ggcaatccaa     720
ctccttgaaa agatgaaaac gagcgcgtcc cccttcttcc tcgccgtggg ctaccacaag     780
ccccacatcc cgtttagata ccccaaggaa tttcagaaac tgtaccccct ggaaaacatc     840
actctcgcgc ccgaccccga agtgccagac ggactccctc tgttgccta caaccttgg     900 atggacatca gcaacgtgaa agatgtgcag gccctgaaca tctcagtgcc ttacggcccc     960
attccagttg acttccagag gaagattcgg cagtcctact cgcctccgt tagttacctg    1020 gacacccaag tgggtagact cctgagcgcc ttggacgatc tccagctcgc aaacagcacc    1080
atcattgcct tcaccagcga ccatggttgg gcgctgggtg aacatggaga atgggctaaa    1140
tattcaaatt tcgacgttgc gacccacgtc ccattgatct tctacgtgcc tggacgaaca    1200
gcctccttgc ctgaagccgg ggaaaagttg tttccatatc tggaccctt cgattctgcg    1260 agccaactca tggaacctgg gcgacagagc atggaactgg tggaactggt cagtttattt    1320 ccaacctgg caggccttgc aggcctccaa gttccacctc ggtgtcccgt ccctcattc    1380 cacgtcgaac tctgtcgcga aggtaaaaac ctcctcaagc attttcgttt cgggacctc    1440 gaagaagacc ataccgtgcc agggaatcca agggaactga ttgcctacag ccagtaccct    1500
agacctagcg acatcccaca gtggaacagc gacaagccct ccctcaagga cattaaaatc    1560
atgggttata gtatccggac tattgactac aggtataccg tgtgggtggg tttcaaccca    1620
```

-continued

```
gacgaatttc tcgccaattt ctccgacatc cacgcgggcg aactgtattt cgttgattcc   1680
gatccactgc aagatcataa tatgtacaac gatagtcaag ggggtgacct cttccagttg   1740
ctaatgccag aagccgccgc gaaagaagcc gccgcaaaag aagccgctgc caaaggcatg   1800
gaagtgcgtt ggtgcgccac ctctgacccc gagcagcaca agtgcggcaa catgtccgag   1860
gccttcagag aggccggcat ccagccttct ctgctgtgtg tgcggggcac ctctgccgac   1920
cattgcgtgc agctgatcgc cgcccaggaa gccgacgcta tcacactgga tggcggcgct   1980
atctacgagg ctggcaaaga gcacggcctg aagcccgtcg tgggcgaggt gtacgatcag   2040
gaagtgggca cctcctacta cgccgtggct gtcgtgcgga gatcctccca cgtgaccatc   2100
gacaccctga agggcgtgaa gtcctgccac accggcatca acagaaccgt gggctggaac   2160
gtgcccgtgg gctacctggt ggaatccggc agactgtccg tgatgggctg cgacgtgctg   2220
aaggccgtgt ccgattactt cggcggctct tgtgtgcctg gcgctggcga catcctac    2280 tccgagtccc tgtgcagact gtgcagggcc gactcttctg gcgagggcgt gtgcgacaag   2340
tcccctctgg aacggtacta cgactactcc ggcgccttca gatgcctggc tgaaggtgct   2400
ggcgacgtgg ccttcgtgaa gcactccacc gtgctggaaa acaccgacgg caagaccctg   2460
ccttcttggg gccaggcact gctgtcccag gacttcgagc tgctgtgccg ggatggctcc   2520
agagccgatg tgacagagtg gcggcagtgc cacctggcca gagtgcctgc tcatgctgtg   2580
gtcgtgcgcg ccgatacaga tggcggcctg atcttccggc tgctgaacga gggccagcgg   2640
ctgttctctc acgagggctc cagcttccag atgttctcca gcgaggccta cggccagaag   2700
gacctgctgt tcaaggactc cacctccgag ctggtgccta tcgccaccca gacctatgag   2760
gcttggctgg ccacgagta cctgcacgct atgaagggac tgctgtgcga ccccaaccgg   2820
ctgcctcctt atctgaggtg gtgcgtgctg tccacccccg agatccagaa atgcggcgat   2880
atggccgtgg cctttcggcg gcagagactg aagcctgaga tccagtgcgt gtccgccaag   2940
agccctcagc actgcatgga acggatccag gccgaacagg tggacgccgt gacactgtcc   3000
ggcgaggata tctacaccgc cggaaagacc tacggcctgg tgccagctgc tggcgagcat   3060
tacgcccctg aggactcctc caacagctac tacgtggtgg cagtcgtgcg ccgggactcc   3120
tctcacgcct ttaccctgga tgagctgcgg ggcaagagaa gctgtcacgc cggctttgga   3180
agccctgccg gatgggatgt gcctgtgggc gctctgatcc agcggggctt catcagaccc   3240
aaggactgtg atgtgctgac cgccgtgtct gagttcttca acgcctcctg tgtgcccgtg   3300
aacaacccca gaactacccc ctccagcctg tgcgccctgt gtgtgggaga tgagcagggc   3360
cggaacaaat gcgtgggcaa ctcccaggaa agatattacg ctacagagg cgccttccgg   3420 tgtctggtgg aaaacgccgg ggatgtgct tttgtgcggc acaccaccgt gttcgacaac   3480
accaatggcc acaactccga gccttgggcc gctgagctga gatccgagga ttacgaactg   3540
ctgtgtccca acgcgccag ggctgaggtg tcccagtttg ccgcctgtaa cctgccccag   3600
atccctcccc acgctgtgat ggtgcgaccc gacaccaaca tcttcaccgt gtacggcctg   3660
ctggacaagg cccaggatct gttcggcgac gaccacaaca agaacgggtt caagatgttc   3720
gactccagca actaccacgg acaggatctg ctgttaaag atgccaccgt gcgggccgtg   3780
ccagtgggcg aaaagaccac ctacagagga tggctgggac tggactacgt ggccgccctg   3840
gaaggcatgt cctcccagca gtgttcctga                                   3870
```

<210> SEQ ID NO 144

<211> LENGTH: 3870
<212> TYPE: DNA
<213> ORGANISM: Artificial Sequence
<220> FEATURE:
<223> OTHER INFORMATION: Polynucleotide coding for p97 fusion protein

<400> SEQUENCE: 144

| | | | | | |
|---|---|---|---|---|---|
| atggaatgga | gctgggtctt | tctcttcttc | ctgtcagtaa | cgactggtgt | ccactccgac | 60 |
| tacaaggacg | acgacgacaa | agagcagaag | ctgatctccg | aagaggacct | gcaccaccat | 120 |
| catcaccatc | accaccatca | cggaggcggt | ggagagaacc | tgtactttca | gggcggcatg | 180 |
| gaagtgcgtt | ggtgcgccac | ctctgacccc | gagcagcaca | agtgcggcaa | catgtccgag | 240 |
| gccttcagag | aggccggcat | ccagccttct | ctgctgtgtg | tgcggggcac | ctctgccgac | 300 |
| cattgcgtgc | agctgatcgc | cgcccaggaa | gccgacgcta | tcacactgga | tgcggcgct | 360 |
| atctacgagg | ctggcaaaga | gcacggcctg | aagcccgtcg | tgggcgaggt | gtacgatcag | 420 |
| gaagtgggca | cctcctacta | cgccgtggct | gtcgtgcgga | gatcctccca | cgtgaccatc | 480 |
| gacaccctga | agggcgtgaa | gtcctgccac | accggcatca | cagaaccgt | gggctggaac | 540 |
| gtgcccgtgg | gctacctggt | ggaatccggc | agactgtccg | tgatgggctg | cgacgtgctg | 600 |
| aaggccgtgt | ccgattactt | cggcggctct | tgtgtgcctg | gcgctggcga | gacatcctac | 660 |
| tccgagtccc | tgtgcagact | gtgcaggggc | gactcttctg | gcgagggcgt | gtgcgacaag | 720 |
| tccctctgg | aacggtacta | cgactactcc | ggcgccttca | gatgcctggc | tgaaggtgct | 780 |
| ggcgacgtgg | ccttcgtgaa | gcactccacc | gtgctggaaa | acaccgacgg | caagaccctg | 840 |
| ccttcttggg | gccaggcact | gctgtcccag | gacttcgagc | tgctgtgccg | ggatggctcc | 900 |
| agagccgatg | tgacagagtg | gcggcagtgc | cacctggcca | gagtgcctgc | tcatgctgtg | 960 |
| gtcgtgcgcg | ccgatacaga | tggcggcctg | atcttccgc | tgctgaacga | gggccagcgg | 1020 |
| ctgttctctc | acgagggctc | cagcttccag | atgttctcca | gcgaggccta | cggccagaag | 1080 |
| gacctgctgt | tcaaggactc | cacctccgag | ctggtgccta | cgccacccca | gacctatgag | 1140 |
| gcttggctgg | ccacgagta | cctgcacgct | atgaagggac | tgctgtgcga | ccccaaccgg | 1200 |
| ctgcctcctt | atctgaggtg | gtgcgtgctg | tccaccccg | agatccagaa | atgcggcgat | 1260 |
| atggccgtgg | cctttcggcg | gcagagactg | aagcctgaga | tccagtgcgt | gtccgccaag | 1320 |
| agccctcagc | actgcatgga | acggatccag | gccgaacagg | tggacgccgt | gacactgtcc | 1380 |
| ggcgaggata | tctacaccgc | cggaaagacc | tacggcctgg | tgccagctgc | tggcgagcat | 1440 |
| tacgccctg | aggactcctc | caacagctac | tacgtggtgg | cagtcgtgcg | ccggactcc | 1500 |
| tctcacgcct | tacccctgga | tgagctgcgg | ggcaagagaa | gctgtcacgc | cggctttgga | 1560 |
| agccctgccg | atgggatgt | gcctgtgggc | gctctgatcc | agcggggctt | catcagaccc | 1620 |
| aaggactgtg | atgtgctgac | cgccgtgtct | gagttcttca | acgcctcctg | tgtgcccgtg | 1680 |
| aacaacccca | gaactaccc | ctccagcctg | tgcgccctgt | gtgtgggaga | tgagcagggc | 1740 |
| cggaacaaat | gcgtgggcaa | ctcccaggaa | agatattacg | gctacagagg | cgccttccgg | 1800 |
| tgtctggtgg | aaaacgccgg | ggatgtggct | tttgtgcggc | acaccaccgt | gttcgacaac | 1860 |
| accaatggcc | acaactccga | gccttgggcc | gctgagctga | gatccgagga | ttacgaactg | 1920 |
| ctgtgtccca | acggcgccag | ggctgaggtg | tcccagtttg | ccgcctgtaa | cctggcccag | 1980 |
| atccctcccc | acgctgtgat | ggtgcgaccc | gacaccaaca | tcttcaccgt | gtacggcctg | 2040 |
| ctggacaagg | cccaggatct | gttcggcgac | gaccacaaca | gaacgggtt | caagatgttc | 2100 |
| gactccagca | actaccacgg | acaggatctg | ctgtttaaag | atgccaccgt | gcgggccgtg | 2160 |

```
ccagtgggcg aaaagaccac ctacagagga tggctgggac tggactacgt ggccgccctg    2220
gaaggcatgt cctcccagca gtgttccgaa gccgccgcga agaagccgc cgcaaaagaa    2280 gccgctgcca atcggaaac tcaggccaac tccaccacag atgcactcaa cgtgctgctg    2340
atcatcgtag atgacctccg accttctctg ggctgttacg gcgacaagct agtacggagc    2400
ccaaacatcg accagctcgc atcgcactct ctcctattcc agaacgcatt cgcccagcag    2460
gctgtctgtg ctccctcccg agtgtccttc ctcacgggtc ggagacccga taccacgagg    2520
ttatatgact tcaactcata ctggcgcgtg catgccggta acttttctac tatacccag    2580 tattttaaag aaaatggcta tgttacaatg tccgttggca aggtatttca tcctggtatt    2640
agcagcaacc acacagatga ctctccgtat agctggtcat tcccaccata ccacccctcc    2700
agcgaaaagt acgaaaacac aaagacttgc cggggcccag atggcgaact gcacgcaaat    2760
ctgctgtgcc ctgtagatgt cttggacgtg cccgaaggta ctctgcccga caaacagtcc    2820
acagaacagg caatccaact ccttgaaaag atgaaaacga gcgcgtcccc cttcttcctc    2880
gccgtgggct accacaagcc ccacatcccg tttagatacc caaggaatt tcagaaactg    2940 tacccctgg aaaacatcac tctcgcgccc gaccccgaag tgccagacgg actccctcct    3000
gttgcctaca acccttggat ggacatcaga caacgtgaag atgtgcaggc cctgaacatc    3060
tcagtgcctt acgccccat tccagttgac ttccagagga agattcggca gtcctacttc    3120
gcctccgtta gttacctgga cacccaagtg ggtagactcc tgagcgcctt ggacgatctc    3180
cagctcgcaa acagcaccat cattgccttc accagcgacc atggttgggc gctgggtgaa    3240
catggagaat gggctaaata ttcaaatttc gacgttgcga cccacgtccc attgatcttc    3300
tacgtgcctg gacgaacagc ctccttgcct gaagccgggg aaaagttgtt tccatatctg    3360
gaccctttcg attctgcgag ccaactcatg gaacctgggc gacagagcat ggacctggtg    3420
gaactggtca gtttatttcc aaccctggca ggccttgcag gcctccaagt tccacctcgg    3480
tgtcccgttc cctcattcca cgtcgaactc tgtcgcgaag gtaaaaacct cctcaagcat    3540
tttcgttttc gggacctcga agaagaccca tacctgccag gaatccaag ggaactgatt    3600 gcctacagcc agtaccctag acctagcgac atccacagt ggaacagcga caagccctcc    3660
ctcaaggaca ttaaaatcat gggttatagt atccggacta ttgactacag gtataccgtg    3720
tgggtgggtt caacccaga cgaatttctc gccaatttct ccgacatcca cgcgggcgaa    3780
ctgtatttcg ttgattccga tccactgcaa gatcataata tgtacaacga tagtcaaggg    3840
ggtgacctct tccagttgct aatgccatga                                      3870
```

<210> SEQ ID NO 145
<211> LENGTH: 1836
<212> TYPE: DNA
<213> ORGANISM: Artificial Sequence
<220> FEATURE:
<223> OTHER INFORMATION: Polynucleotide coding for p97 fusion protein

<400> SEQUENCE: 145

```
atggaatgga gctgggtctt tctcttcttc ctgtcagtaa cgactggtgt ccactccgac     60
tacaaggacg acgacgacaa agagcagaag ctgatctccg aagaggacct gcaccaccat    120
catcaccatc accaccatca cggaggcggt ggagagaacc tgtactttca gggcgactcc    180
tctcacgcct tcaccctgga cgagctgcgg tacgaagccg ccgcgaaaga agccgccgca    240
aaagaagccg ctgccaaatc ggaaactcag gccaactcca ccacagatgc actcaacgtg    300
```

```
ctgctgatca tcgtagatga cctccgacct tctctgggct gttacggcga caagctagta    360
cggagcccaa acatcgacca gctcgcatcg cactctctcc tattccagaa cgcattcgcc    420
cagcaggctg tctgtgctcc ctcccgagtg tccttcctca cgggtcggag acccgatacc    480
acgaggttat atgacttcaa ctcatactgg cgcgtgcatg ccgtaacttt ttctactata    540
ccccagtatt ttaaagaaaa tggctatgtt acaatgtccg ttggcaaggt atttcatcct    600
ggtattagca gcaaccacac agatgactct ccgtatagct ggtcattccc accataccac    660
ccctccagcg aaaagtacga aaacacaaag acttgccggg gcccagatgg cgaactgcac    720
gcaaatctgc tgtgccctgt agatgtcttg gacgtgcccg aaggtactct gcccgacaaa    780
cagtccacag aacaggcaat ccaactcctt gaaaagatga aaacgagcgc gtccccttc     840
ttcctcgccg tgggctacca caagcccac atcccgttta gatacccaa ggaatttcag      900
aaactgtacc cctggaaaa catcactctc gcgcccgacc ccgaagtgcc agacggactc     960
cctcctgttg cctacaaccc ttggatggac atcagacaac gtgaagatgt gcaggccctg   1020
aacatctcag tgccttacgg ccccattcca gttgacttcc agaggaagat tcggcagtcc   1080
tacttcgcct ccgttagtta cctggacacc caagtgggta gactcctgag cgccttggac   1140
gatctccagc tcgcaaacag caccatcatt gccttcacca cgaccatgg ttgggcgctg    1200
ggtgaacatg gagaatgggc taaatattca aatttcgacg ttgcgaccca cgtcccattg   1260
atcttctacg tgcctggacg aacagcctcc ttgcctgaag ccggggaaaa gttgtttcca   1320
tatctggacc ctttcgattc tgcgagccaa ctcatggaac tgggcgaca gagcatggac    1380
ctggtggaac tggtcagttt atttccaacc ctggcaggcc ttgcaggcct ccaagttcca   1440
cctcggtgtc ccgttccctc attccacgtc gaactctgtc gcgaaggtaa aaacctcctc   1500
aagcattttc gttttcggga cctcgaagaa gacccatacc tgccagggaa tccaagggaa   1560
ctgattgcct acagccagta ccctagacct agcgacatcc acagtggaa cagcgacaag    1620
ccctcccctca aggacattaa aatcatgggt tatagtatcc ggactattga ctacaggtat   1680
accgtgtggg tgggtttcaa cccagacgaa tttctcgcca atttctccga catccacgcg   1740
ggcgaactgt atttcgttga ttccgatcca ctgcaagatc ataatatgta caacgatagt   1800
caagggggtg acctcttcca gttgctaatg ccatga                              1836
```

<210> SEQ ID NO 146
<211> LENGTH: 1836
<212> TYPE: DNA
<213> ORGANISM: Artificial Sequence
<220> FEATURE:
<223> OTHER INFORMATION: Polynucleotide coding for p97 fusion protein

<400> SEQUENCE: 146

```
atggaatgga gctgggtctt tctcttcttc ctgtcagtaa cgactggtgt ccactccgac     60
tacaaggacg acgacgacaa agagcagaag ctgatctccg aagaggacct gcaccaccat   120
catcaccatc accaccatca cggaggcggt ggagagaacc tgtactttca gggctcggaa   180
actcaggcca actccaccac agatgcactc aacgtgctgc tgatcatcgt agatgaccttc 240
cgaccttctc tgggctgtta cggcgacaag ctagtacgga gcccaaacat cgaccagctc   300
gcatcgcact ctcctctatt ccagaacgca ttcgcccagc aggctgtctg tgctccctcc   360
cgagtgtcct cctcacggg tcggagaccc gataccacga ggttatatga cttcaactca    420
tactggcgcg tgcatgccgg taacttttct actataccc agtattttaa agaaaatggc   480
tatgttacaa tgtccgttgg caaggtattt catcctggta ttagcagcaa ccacacagat   540
```

```
gactctccgt atagctggtc attcccacca taccacccct ccagcgaaaa gtacgaaaac      600
acaaagactt gccggggccc agatggcgaa ctgcacgcaa atctgctgtg ccctgtagat      660
gtcttggacg tgcccgaagg tactctgccc gacaaacagt ccacagaaca ggcaatccaa      720
ctccttgaaa agatgaaaac gagcgcgtcc cccttcttcc tcgccgtggg ctaccacaag      780
ccccacatcc cgtttagata ccccaaggaa tttcagaaac tgtaccccct ggaaaacatc      840
actctcgcgc ccgaccccga agtgccgacg ggactccctc ctgttgccta caaccccttgg     900 atggacatca gacaacgtga agatgtgcag gccctgaaca tctcagtgcc ttacggcccc      960
attccagttg acttccagag gaagattcgg cagtcctact tcgcctccgt tagttacctg     1020
gacacccaag tgggtagact cctgagcgcc ttggacgatc tccagctcgc aaacagcacc     1080
atcattgcct tcaccagcga ccatggttgg gcgctgggtg aacatggaga atgggctaaa     1140
tattcaaatt tcgacgttgc gacccacgtc ccattgatct tctacgtgcc tggacgaaca     1200
gcctccttgc ctgaagccgg ggaaaagttg tttccatatc tggacccttt cgattctgcg     1260
agccaactca tggaacctgg gcgacagagc atggacctgg tggaactggt cagtttattt     1320
ccaaccctgg caggccttgc aggcctccaa gttccacctc ggtgtcccgt tccctcattc     1380
cacgtcgaac tctgtcgcga aggtaaaaac ctcctcaagc attttcgttt tcgggacctc     1440
gaagaagacc catacctgcc agggaatcca agggaactga ttgcctacag ccagtaccct     1500
agacctagcg acatcccaca gtggaacagc gacaagccct ccctcaagga cattaaaatc     1560
atgggttata gtatccggac tattgactac aggtataccg tgtgggtggg tttcaaccca     1620
gacgaatttc tcgccaattt ctccgacatc cacgcgggcg aactgtattt cgttgattcc     1680
gatccactgc aagatcataa tatgtacaac gatagtcaag ggggtgacct cttccagttg     1740
ctaatgccag aggccgctgc taagaggct gccgccaaag aagccgccgc taaggactcc     1800
tctcacgcct tcaccctgga cgagctgcgg tactaa                                1836

<210> SEQ ID NO 147
<211> LENGTH: 1812
<212> TYPE: DNA
<213> ORGANISM: Artificial Sequence
<220> FEATURE:
<223> OTHER INFORMATION: Polynucleotide coding for p97 fusion protein

<400> SEQUENCE: 147
atggaatgga gctgggtctt tctcttcttc ctgtcagtaa cgactggtgt ccactccgac       60
tacaaggacg acgacgacaa agagcagaag ctgatctccg aagaggacct gcaccaccat      120
catcaccatc accaccatca cggaggcggt ggagagaacc tgtactttca gggcacagat      180
gcactcaacg tgctgctgat catcgtagat gacctccgac cttctctggg ctgttacggc      240
gacaagctag tacggagccc aaacatcgac cagctcgcat cgcactctct cctattccag      300
aacgcattcg cccagcaggc tgtctgtgct ccctcccgag tgtccttcct cacgggtcgg      360
agacccgata ccacgaggtt atatgacttc aactcatact ggcgcgtgca tgccggtaac      420
ttttctacta tacccccagta tttttaaagaa aatggctatg ttacaatgtc cgttggcaag      480
gtatttcatc ctggtattag cagcaaccac acagatgact ctccgtatag ctggtcattc      540
ccaccatacc accccctccag cgaaaagtac gaaaacacaa agacttgccg ggcccagat      600 ggcgaactgc acgcaaatct gctgtgccct gtagatgtct tggacgtgcc cgaaggtact      660
ctgcccgaca aacagtccac agaacaggca atccaactcc ttgaaaagat gaaaacgagc      720
```

```
gcgtccccct tcttcctcgc cgtgggctac cacaagcccc acatcccgtt tagataccccc    780 aaggaatttc agaaactgta cccccctggaa aacatcactc tcgcgcccga ccccgaagtg    840
ccagacggac tccctcctgt tgcctacaac ccttggatgg acatcagaca acgtgaagat    900
gtgcaggccc tgaacatctc agtgccttac ggccccattc cagttgactt ccagaggaag    960
attcggcagt cctacttcgc ctccgttagt tacctggaca cccaagtggg tagactcctg   1020
agcgccttgg acgatctcca gctcgcaaac agcaccatca ttgccttcac cagcgaccat   1080
ggttgggcgc tgggtgaaca tggagaatgg gctaaatatt caaatttcga cgttgcgacc   1140
cacgtcccat tgatcttcta cgtgcctgga cgaacagcct ccttgcctga agccggggaa   1200
aagttgtttc catatctgga ccctttcgat tctgcgagcc aactcatgga acctgggcga   1260
cagagcatgg acctggtgga actggtcagt ttatttccaa ccctggcagg ccttgcaggc   1320
ctccaagttc cacctcggtg tcccgttccc tcattccacg tcgaactctg tcgcgaaggt   1380
aaaaacctcc tcaagcattt tcgttttcgg gacctcgaag aagacccata cctgccaggg   1440
aatccaaggg aactgattgc ctacagccag taccctagac ctagcgacat cccacagtgg   1500
aacagcgaca agccctccct caaggacatt aaaatcatgg gttatagtat ccggactatt   1560
gactacaggt ataccgtgtg ggtgggtttc aacccagacg aatttctcgc caatttctcc   1620
gacatccacg cgggcgaact gtatttcgtt gattccgatc cactgcaaga tcataatatg   1680
tacaacgata gtcaaggggg tgacctcttc cagttgctaa tgccagaggc cgctgctaaa   1740
gaggctgccg ccaaagaagc cgccgctaag gactcctctc acgccttcac cctggacgag   1800
ctgcggtact aa                                                        1812

<210> SEQ ID NO 148
<211> LENGTH: 13
<212> TYPE: PRT
<213> ORGANISM: Homo sapiens

<400> SEQUENCE: 148

Asp Ser Ser His Ala Phe Thr Leu Asp Glu Leu Arg Tyr
1               5                   10

<210> SEQ ID NO 149
<211> LENGTH: 19
<212> TYPE: PRT
<213> ORGANISM: Homo sapiens

<400> SEQUENCE: 149

Met Glu Trp Ser Trp Val Phe Leu Phe Phe Leu Ser Val Thr Thr Gly
1               5                   10                  15

Val His Ser
```